United States Patent
Lovenberg et al.

(10) Patent No.: US 7,034,118 B2
(45) Date of Patent: Apr. 25, 2006

(54) CORTICOTROPIN-RELEASING FACTOR₂ RECEPTORS

(75) Inventors: Timothy W Lovenberg, Carlsbad, CA (US); Tilman Oltersdorf, Cardiff, CA (US); Chen Wang Liaw, San Diego, CA (US); Dimitri E Grigoriadis, Carlsbad, CA (US); Derek T Chalmers, Solana Beach, CA (US); Errol B DeSouza, Del Mar, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 67 days.

(21) Appl. No.: 10/821,502

(22) Filed: Apr. 9, 2004

(65) Prior Publication Data

US 2004/0185533 A1    Sep. 23, 2004

Related U.S. Application Data

(63) Continuation of application No. 09/881,401, filed on Jun. 13, 2001, now Pat. No. 6,723,841, which is a continuation of application No. 09/227,482, filed on Jan. 7, 1999, now abandoned, which is a continuation of application No. 08/485,984, filed on Jun. 7, 1995, now abandoned, which is a continuation-in-part of application No. 08/381,433, filed on Jan. 31, 1995, now Pat. No. 5,786,203, which is a continuation-in-part of application No. 08/259,959, filed on Jun. 14, 1994, now abandoned.

(51) Int. Cl.
C07K 14/705    (2006.01)

(52) U.S. Cl. ..................... 530/350; 536/23.5

(58) Field of Classification Search .................... None
See application file for complete search history.

(56) References Cited

U.S. PATENT DOCUMENTS 5,786,203 A    7/1998    Lovenberg et al. ...... 435/252.3

FOREIGN PATENT DOCUMENTS

EP    695 802 A2    2/1996

OTHER PUBLICATIONS

Bilezikjian, and Vale, "Glucocorticoids Inhibit Corticotropin-Releasing Facotor-Induced Production of Adenosine 3', 5'-Monophosphate in Cultured Anterior Pituitary Cells," *Endocrinology* 113(2): 657-662, Aug., 1983.

Chang et al., "Indentification of a Seven Transmembrane Helix Receptor for Corticotropin -Releasing Factor and Sauvagine in Mammalian Brain," *Neuron 11*1187-1195:, 1993.

Chen et al., "Expression cloning of a human corticotropin-releasing-factor receptor," *Proc. Natl. Acad. Sci. 90*: 8967-8971, 1993.

De Souza et al., "Corticotropin-Releasing Factor Receptors in Rat Forebrain: Autoradiographic Indentification," *Science 224*(4656): 1449-1451, Jun., 1984.

De Souza, E., "Corticotropin-Releasing Factor Receptors in the Rat Cental Nervous System. Characterization and Regional Distribution," *Journal of Neuroscience* 7(1): 88-100, 1987.

GenBank Accession No. L23332 (Submitted Oct. 22, 1993).

Hernandez et al., "Synthesis and Relative Potencies of New Constrained CRF Antagonists," *J. Med. Chem.* 36(20): 2860-2867, Oct., 1993.

Lederis et al., "Complete Amino Acid Sequence of Urotensin I, a Hypotensive and Corticotropin-Releasing Neuropeptide from *Catostomus*," *Science* 218(4568): 162-164, Oct., 1982.

Lovenberg et al., "Cloning and characterization of a functionally distinct corticotropin-releasing factor receptor subtype from rat brain,"*Proc. Natl. Acad. Sci.* 92: 836-840, 1995.

Milan et al., "Distribution of corticotropin-releasing factor receptors in primate brain," *Proc. Natl. Acad. Sci. USA 83*: 921-1925, Mar., 1986.

Miyata et al., "Cloning and Characterization of a Short Variant of the Corticotropin- Releasing Factor Receptor Subtype from Rat Amygdala," *Biochem. and Biophys. Res. Comm.* 256(3): 692-696, Mar., 1999.

Perrin et al., "Cloning and Functional Expression of a Rat Brain Corticotropin Releasing Factor (CRF) Receptor," *Endocrinology 133*(6): 3058-3061, 1993.

Perrin et al., "Corticotropin-Releasing Factor Binding to the Anterior Pituitary Receptor Is Modulated by Divalent Cations and Guanyl Nucleotides," *Endocrinology 118*(3): 1171-1179, Mar., 1986.

(Continued)

*Primary Examiner*—John Ulm
(74) *Attorney, Agent, or Firm*—Seed IP Law Group

(57) ABSTRACT

The present invention provides isolated nucleic acid molecules encoding $CRF_2$ receptors, recombinant expression vectors and host cells suitable for expressing such receptors, as well as compositions and methods which utilize such receptors.

2 Claims, 18 Drawing Sheets

OTHER PUBLICATIONS

Proll et al., "A$_1$ and A$_2$ adenosine receptors regulate adenylate cyclase in cultured human lung fibroblasts," *Mol. and Cell. Endrocrin. 44* : 211-217, 1986.

Rivier et al., "Single Point D-Substituted Corticotropin-Realeasing Factor Analogues: Effects on Potency and Physicochemical Characteristics," *J Med Chem 36*(20: 2851-2859, Oct., 1993.

Rivier et al., "Synthetic Competitive Antagonists of Corticotropin-Releasing Factor: Effect on ACTH Secretion in the Rat," *Science 224*(4651):889-891, May, 1984.

Stenzel et al., "Identification of a Novel Murine Receptor for Corticotropin-Releasing Hormone Expressed in the Heart," *Molecular Endocrinology 9*(5): 637-645, 1995.

Udelsman et al., "Functional corticotropin releasing factor receptors in the primate peripheral sympathetic nervous system," *Nature 319*: 147-150, Jan.1986.

Vale et al., "Characterization of a 41-Residue Ovine Hypothalamic Peptide That Stimulates Secretion of Corticotropin and β-Endorphin," *Science 213*94514): 1394-1397, Sep. 1981.

Vita et al., "Primary structure and functional expression of mouse pituitary and human brain corticotrophin releasing factor receptors," *FEBS Letters 335*(1): 1-5, 1993.

Webster and DeSouza, "Corticotorpin-Releasing Factor Receptors in Mouse Spleen: Indentification, Autoradiographic Localization, and Regulation by Divalent Cations and Guanine Nucleotides, " *Endocrinology 122*(2): 609-617, Feb., 1988.

Wynn et al., "Properties and Regulation of High-Affinity Pituitary Receptors for Corticotropin-Releasing Factor," *Biochem. Biophys. Res. Comm. 110*(2): 602-608, Jan.,1983.

Wynn et al., "Brain and Pituitary Receptors for Corticotropin Releasing Factor: Localization and Differential Regulation After Adrenalectomy," *Peptides 5* : 1077-1084, 1984.

CRF$_{2\alpha}$

CRF$_{2\beta}$

CORTICOTROPIN-RELEASING FACTOR₂ RECEPTORS

CROSS-REFERENCE TO RELATED APPLICATIONS

This application is a continuation of U.S. application Ser. No. 09/881,401, filed Jun. 13, 2002, now issued as U.S. Pat. No. 6,723,841; which is continuation of U.S. application Ser. No. 09/227,482, filed Jan. 7, 1999, now abandoned; which is a continuation of U.S. patent application Ser. No. 08/485,984, filed Jun. 7, 1995, now abandoned; which is a continuation-in-part of U.S. patent application Ser. No. 08/381,433, filed Jan. 31, 1995, now issued as U.S. Pat. No. 5,786,203; which is a continuation-in-part of U.S. patent application Ser. No. 08/259,959, filed Jun. 14, 1994, now abandoned.

BACKGROUND OF THE INVENTION

1. Field of the Invention

The present invention relates generally to cell surface receptors, and more specifically, to Corticotropin-Releasing Factor₂ receptors.

2. Description of the Related Art

Corticotropin-releasing factor ("CRF") is a 41-amino acid peptide originally isolated from the hypothalamus by virtue of its ability to stimulate the production of adrenocorticotropic hormone ("ACTH") and other proopiomelanocortin ("POMC") products of the anterior pituitary (Vale et al., Science 213:1394–1397, 1981). Briefly, CRF is believed to initiate its biological effects by binding to a plasma membrane receptor which is distributed throughout the brain (DeSouza et al., Science 224:1449–1451, 1984), pituitary (Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617,1988). This receptor is coupled to a GTP-binding protein (Perrin et al., Endocrinology 118:1171–1179, 1986) which mediates CRF-stimulated increase in intracellular cAMP (Bilezikjian, L. M., and W. W. Vale, Endocrinology 113:657–662,1983).

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555–2564,1992; Sapolsky et al., Science 238:522–524, 1987; Tilders et al., Regul. Peptides 5:77–84, 1982; Fisher et al., Reg. Peptide 5:153–161, 1983).

A receptor for CRF has been cloned from rat (Perrin et al., Endo 133(6):3058–3061,1993), and human brain (Chen et al., PNAS 90(19):8967–8971, 1993; Vita et al., FEBS 335 (1):1–5, 1993). This receptor is a 415 amino acid protein comprising seven membrane spanning domains, and has a predicted molecular weight of 44,000 daltons. A comparison of identity between rat and human sequences shows a high degree of homology (97%) at the amino acid level. In addition, Scatchard analysis of recombinantly produced human receptor demonstrates a single component site, with a high affinity ($K_d$ of 1.6±0.3 nM) for CRF.

The present invention provides new, previously unidentified CRF receptors, designated as the "Corticotropin-Releasing Factor-₂" ("CRF₂"), Corticotropin-Releasing Factor receptors. In addition, the present invention provides compositions and methods which utilize such CRF₂ receptors, as well as other, related advantages.

BRIEF SUMMARY OF THE INVENTION

Briefly stated, the present invention provides compositions and methods which utilize CRF₂ receptors (also termed "CRF₂ Corticotropin-Releasing Factor receptors" or "CRF₂R"). Within one aspect of the present invention, isolated nucleic acid molecules are provided which encode CRF₂ receptors. Within one embodiment, nucleic acid molecules are provided which encode a CRF₂ receptor such as that disclosed in Sequence I.D. No. 4, from amino acid number 1 to amino acid number 411. Within another embodiment, nucleic acid molecules are provided which comprise the sequence of nucleotides in Sequence I.D. No. 3, from nucleotide number 216 to nucleotide number 1449. Within another embodiment, nucleic acid molecules are provided which encode a CRF₂ receptor such as that disclosed in Sequence ID No. 2 from amino acid number 1 to amino acid number 431. Within another embodiment, nucleic acid molecules are provided which comprise the sequence of nucleotides in Sequence ID No. 1 from nucleotide number 44 to nucleotide number 1336. Nucleic acid molecules which encode CRF₂ receptors of the present invention may be isolated from virtually any warm-blooded animal, including for example, humans, macaques, horses, cattle, sheep, pigs, dogs, cats, rats and mice.

Within another aspect of the present invention, isolated nucleic acid molecules are provided which encode portions of a CRF₂ receptor, such as the N-terminal extracellular domain. Within one embodiment, isolated nucleic acid molecules are provided comprising the sequence of nucleotides in Sequence I.D. No. 3, from nucleotide number 216 to nucleotide number 570. Within another embodiment, isolated nucleic acid molecules are provided which encode a protein having the amino acid sequence of Sequence I.D. No. 4, from amino acid number 1 to amino acid number 118. Within another embodiment, isolated nucleic acid molecules are provided comprising the sequence of nucleotides in Sequence ID No. 1 from nucleotide number 44 to nucleotide number 451. Within another embodiment, isolated nucleic acid molecules are provided which encode a protein having the amino acid sequence of Sequence ID No. 2 from amino acid number 1 to amino acid number 138.

Within other aspects of the invention, expression vectors are provided which are capable of expressing the above-described nucleic acid molecules. Within other aspects, recombinant viral vectors are provided which are capable of directing the expression of the above-described nucleic acid molecules. Representative examples of such viral vectors include retroviral vectors, adenoviral vectors, and herpes simplex virus vectors. Also provided by the present invention are host cells which contain the above-described expression vectors, as well as the receptor or portions thereof which are encoded by the above-described nucleic acid molecules. Within other embodiments, isolated portions of CRF₂ receptors are provided, including for example, isolated portions of extracellular domains such as the N-terminal extracellular domain.

Within other aspects of the invention, isolated antibodies are provided which are capable of specifically binding to the above-described CRF₂ receptors. Within one embodiment, the antibodies may be selected from the group consisting of polyclonal antibodies, monoclonal antibodies, and antibody fragments. Within other embodiments, antibodies are provided which are capable of blocking the binding of CRF (or other substrates such as sauvagine or urotensin I) to a $CRF_2$ receptor. Within preferred embodiments, the antibodies may be selected from the group consisting of murine and human antibodies. Within preferred aspects of the invention, the above-noted antibodies are produced by hybridomas.

Within yet another aspect of the present invention, nucleic acid molecules are provided which are capable of specifically hybridizing to a nucleic acid molecule encoding any of the $CRF_2$ receptors described above. Such molecules may be between at least "y" nucleotides long, wherein "y" is any integer between 14 and 1230, and furthermore, may be selected suitable for use as probes or primers described below. Particularly preferred probes of the present invention are at least 18 nucleotides in length.

Within other aspects of the present invention, methods for detecting the presence of a compound which binds to a $CRF_2$ receptor are provided, comprising the steps of (a) exposing one or more compounds to cells that express $CRF_2$ receptors under conditions and for a time sufficient to allow binding of the compounds to the receptors, and (b) isolating compounds which bind to the receptors, such that the presence of a compound which binds to a $CRF_2$ receptor may be detected. Within another aspect, methods for detecting the presence of a compound which binds to a $CRF_2$ receptor are provided, comprising the steps of (a) exposing one or more compounds to a $CRF_2$ receptor N-terminal extracellular domain under conditions and for a time sufficient to allow binding of a compound to the N-terminal extracellular domain, and (b) isolating compounds which bind to the $CRF_2$ receptor N-terminal extracellular domain, such that the presence of a compound which binds to a $CRF_2$ receptor may be detected. Within one embodiment, the compounds are labeled with an agent selected from the group consisting of fluorescent molecules, enzymes, and radionuclides.

Within other aspects of the present invention, methods for determining whether a selected compound is a $CRF_2$ receptor agonist or antagonist are provided, comprising the steps of (a) exposing a selected compound to cells which express $CRF_2$ receptors under conditions and for a time sufficient to allow binding of the compound and an associated response in intracellular levels of cAMP, and (b) detecting either an increase or decrease in the level of intracellular cAMP, and thereby determining whether the selected compound is a $CRF_2$ receptor agonist or antagonist.

Within other aspects, methods are provided for detecting the presence of a $CRF_2$ receptor agonist or antagonist in a pool of compounds, comprising the steps of (a) exposing a pool of compounds to cells which express $CRF_2$ receptors under conditions and for a time sufficient to allow binding of the compound and an associated response in intracellular levels of cAMP, and (b) isolating compounds which either increase or decrease the intracellular level of cAMP, such that the presence of a $CRF_2$ receptor agonist or antagonist may be detected.

Within another aspect, methods for determining whether a selected compound is a $CRF_2$ receptor antagonist are provided, comprising the steps of (a) exposing a selected compound in the presence of a $CRF_2$ receptor agonist to a recombinant $CRF_2$ receptor coupled to a response pathway under conditions and for a time sufficient to allow binding of the compound to the receptor and an associated response through the pathway, and (b) detecting a reduction in the stimulation of the response pathway resulting from the binding of the compound to the $CRF_2$ receptor, relative to the stimulation of the response pathway by the $CRF_2$ receptor agonist alone, and therefrom determining the presence of a $CRF_2$ antagonist. Within other aspects, methods are provided for determining whether a selected compound is a $CRF_2$ receptor agonist, comprising the steps of (a) exposing a selected compound to a recombinant $CRF_2$ receptor coupled to a response pathway under conditions and for a time sufficient to allow binding of the compound to the receptor and an associated response through the pathway, and (b) detecting an increase in stimulation of the response pathway resulting from the binding of the compound to the $CRF_2$ receptor, and therefrom determining the presence of a $CRF_2$ receptor agonist.

Within other aspects of the present invention, methods are provided for treating $CRF_2$ receptor-associated diseases, wherein it is desired to either increase or decrease stimulation of a $CRF_2$ receptor response pathway. For example, within one aspect methods are provided for treating cerebrovascular disorders such as stroke, reperfusion injury and migraines, comprising the step of administering to a patient a therapeutically effective amount of a $CRF_2$ receptor antagonist, such that the disorder is remedied or alleviated. Within other aspects, methods are provided for treating learning or memory disorders, comprising administering to a patient a therapeutically effective amount of a $CRF_2$ receptor antagonist. Within yet other aspects, methods are provided for treating Alzheimer disease, comprising administering to a patient a therapeutically effective amount of a $CRF_2$ receptor antagonist. Representative examples of suitable $CRF_2$ receptor antagonist include α-helical oCRF (9–41), or d-Phe r/h CRF (12–41).

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 8A', B' and C' are adjacent sections probed with CRF2β antisense cRNA.

DETAILED DESCRIPTION OF THE INVENTION

Definitions

Figure 1:
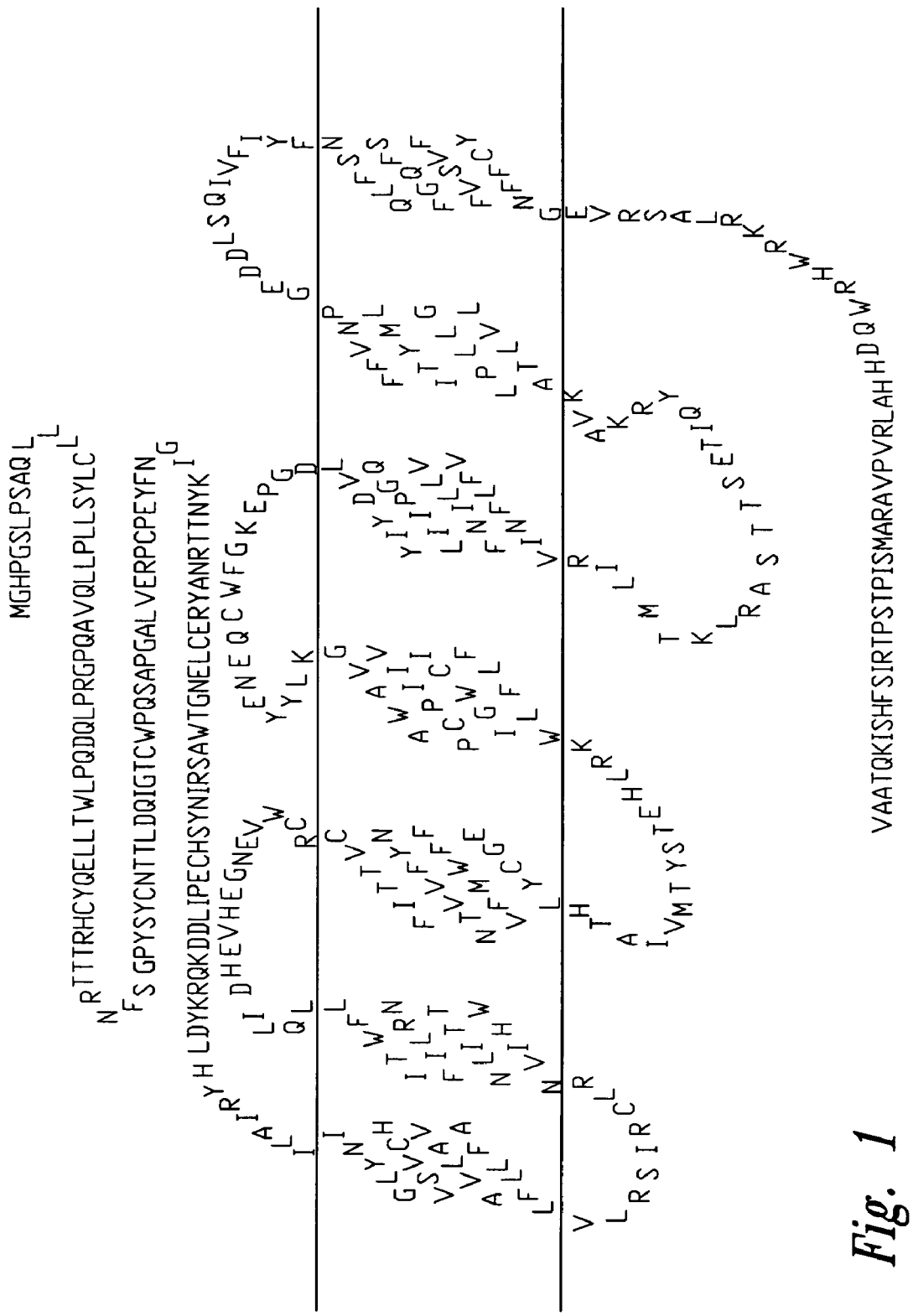
FIG. 1 schematically illustrates the structure of one representative $CRF_2$ receptor ($CRF_{2\beta}$; Sequence ID No. 2).

Prior to setting forth the invention, it may be helpful to an understanding thereof to set forth definitions of certain terms to be used hereinafter.

"$CRF_2$ receptors" (also termed "$CRF_2$ Corticotropin-Releasing Factor receptors" or "$CRF_2R$") as utilized herein refers to receptor proteins which bind corticotropin-releasing factor and other proteins such as urotensin I and sauvagine. $CRF_2$ receptors may be distinguished from other receptors such as Corticotropin-Releasing Factor receptors based upon criteria such as affinity of substrate binding, tissue distribution, and sequence homology. For example, $CRF_2$ receptors of the present invention should be greater than 70% homologous, preferably greater than 75% to 80% homologous, more preferably greater than 85% to 90% homologous, and most preferably greater than 92%, 95%, or 97% homologous to the $CRF_2$ receptors disclosed herein (e.g., Sequence I.D. No. 3). In their native configuration, $CRF_2$ receptors are believed to exist as membrane bound proteins, consisting of an N-terminal extracellular domain, seven transmembrane domains separated by three intracellular and three extracellular loops, and a C-terminal intracellular domain (see FIGS. 1 and 2). As utilized within the context of the present invention $CRF_2$ receptors should be understood to include not only the proteins which are disclosed herein (see Sequence I.D. Nos. 2, 4 and 8), but substantially similar derivatives and analogs as discussed below.

"Nucleic acid molecule" refers to a nucleic acid sequence, in the form of a separate fragment or as a component of a larger nucleic acid construct, which has been derived from nucleic acid isolated at least once in substantially pure form, i.e., free of contaminating endogenous materials, and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic nucleic acid containing the relevant sequences may also be used. Sequences of non-translated nucleic acid may be present 5' or 3' from the open reading frame, where the same do not interfere with manipulation or expression of the coding regions.

"Recombinant expression vector" refers to a replicable nucleic acid construct used either to amplify or to express nucleic acid sequences which encode $CRF_2$ receptors. This construct comprises an assembly of (1) a genetic element or elements having a regulatory role in gene expression, for example, promoters, (2) a structural or coding sequence which is transcribed into mRNA and translated into protein, and (3) appropriate transcription and translation initiation and termination sequences.

As noted above, the present invention provides isolated nucleic acid molecules encoding $CRF_2$ receptors. Briefly, $CRF_2$ receptors are G-coupled protein receptors, which are capable of binding a substrate (such as CRF, or other substrates such as sauvagine and urotensin 1), and transducing the signal provided by the substrate to the cell. Such signal transduction typically occurs when a response pathway is activated by an external stimulus that is generally, but not always, directly coupled to a membrane-bound receptor. Response pathways generally induce cellular responses such as extracellular matrix secretion from responsive cell lines, hormone secretion, chemotaxis, differentiation, or the initiation or inhibition of cell division of responsive cells. As used herein, the coupling of receptors to response pathways refers to the direct activation of a response pathway or the transduction of a signal via a second messenger, such as a G-protein, to activate a cellular response pathway.

Figure 2:
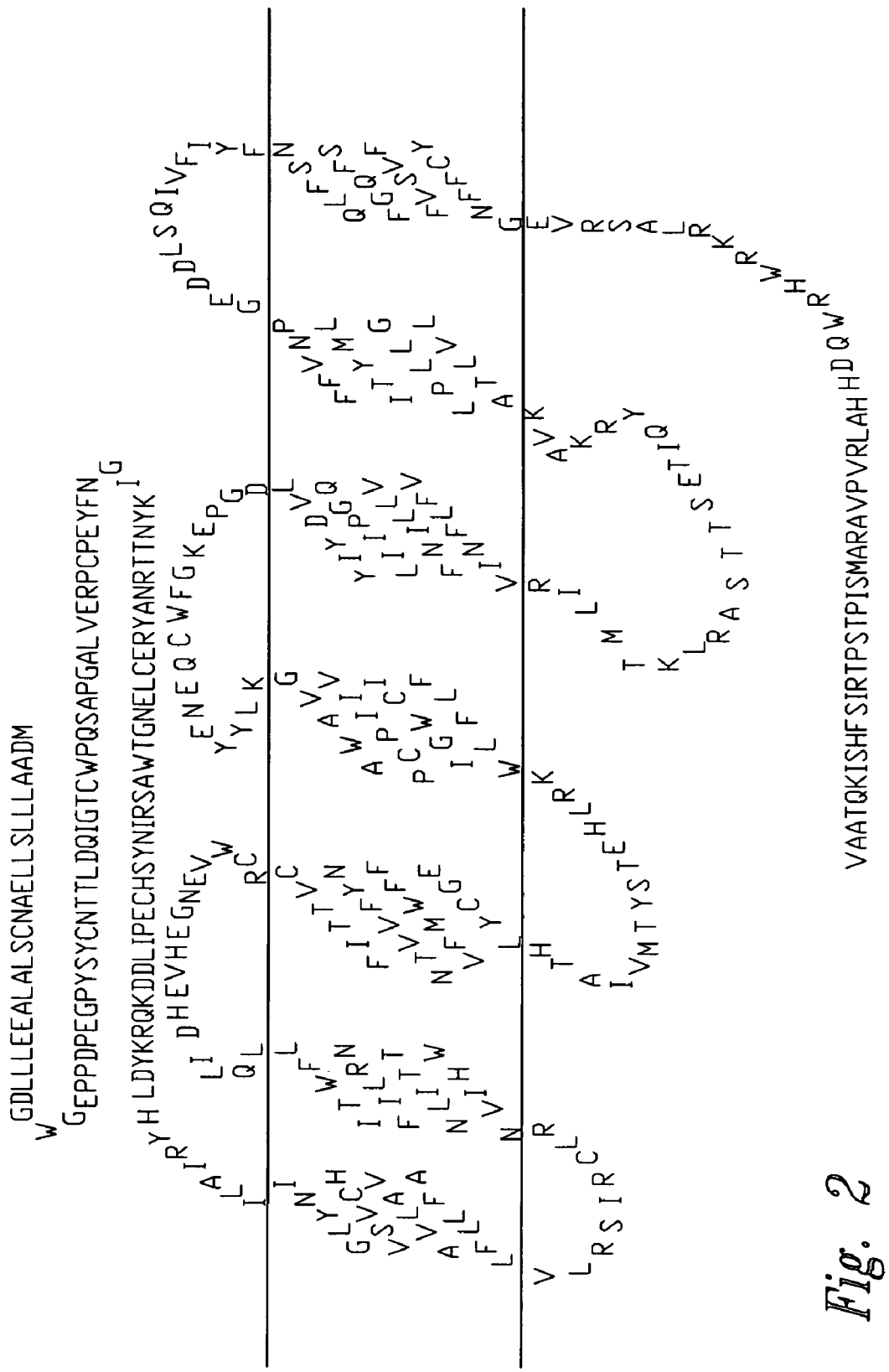
FIG. 2 schematically illustrates the structure of a second representative $CRF_2$ receptor ($CRF_{2\alpha}$; Sequence ID No. 4).

One representative $CRF_2$ receptor which may be obtained utilizing the methods described herein (see Example 1) is schematically illustrated in FIG. 1 (see also FIG. 2. Briefly, this $CRF_2$ receptor is composed of an Extracellular N-terminal Domain (amino acids 1–117), a first Transmembrane Domain (amino acids 118–138), a first Intracellular Domain (139–147), a second Transmembrane Domain (148–167), a second Extracellular Domain (168–184), a third Transmembrane Domain (185–208), a second Intracellular Domain (229–223), a fourth Transmembrane Domain (224–244), a third Extracellular Domain (245–261), a fifth Transmembrane Domain (262–286), a third Intracellular Domain (287–309), a sixth Transmembrane Domain (310–329), a fourth Extracellular Domain (330–342), a seventh Transmembrane Domain (343–363), and a C-terminal Intracellular Domain (364–411).

Although the above $CRF_2$ receptor has been provided for purposes of illustration (see also FIG. 2 and Sequence I.D. No. 2), the present invention should not be so limited. In particular, the present invention provides a wide variety of additional $CRF_2$ receptors which have substantial similarity to the sequences disclosed in Sequences I.D. Nos. 1–4. As utilized within the context of the present invention, nucleic acid sequences which encode $CRF_2$ receptors are deemed to be substantially similar to those disclosed herein if: (a) the nucleic acid sequence is derived from the coding region of a native $CRF_2$ receptor gene (including, for example, allelic variations of the sequences disclosed herein); (b) the nucleic acid sequence is capable of hybridization to nucleic acid sequences of the present invention under conditions of either moderate (e.g. 50% formamide, 5×SSPE, 5× Denhardt's, 0.1% SDS, 100 ug/ml Salmon Sperm nucleic acid, and a temperature of 42° C.) or high stringency (see Sambrook et al., *Molecular Cloning: A Laboratory Manual*, 2d Ed., Cold Spring Harbor Laboratory Press, NY, 1989); or (c) nucleic acid sequences are degenerate as a result of the genetic code to the nucleic acid sequences defined in (a) or (b). Furthermore, although nucleic acid molecules are primarily referred to herein, as should be evident to one of skill in the art given the disclosure provided herein, a wide variety of related nucleic acid molecules may also be utilized in various embodiments described herein, including for example, RNA, nucleic acid analogues, as well as chimeric nucleic acid molecules which may be composed of more than one type of nucleic acid.

In addition, as noted above, within the context of the present invention "$CRF_2$ receptors" should be understood to include derivatives and analogs of the $CRF_2$ receptors described above. Such derivatives include allelic variants and genetically engineered variants that contain conservative amino acid substitutions and/or minor additions, substitutions or deletions of amino acids, the net effect of which does not substantially change the biological activity (e.g., signal transduction) or function of the $CRF_2$ receptor. Such derivatives are generally greater than about 70% to 75% similar to the corresponding native $CRF_2$ receptor, preferably greater than 80% to 85% similar, more preferably greater than 90% to 95% similar, and most preferably greater than 97% similar. Percent similarity may be determined, for example, by comparing sequence information with the GAP program, which utilizes the alignment method of Needleman and Wunsch (*J. Mol. Biol.* 48:443,1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (*Nucl. Acids Res.* 14:6745, 1986), as described by Schwartz and Dayhoff (ed., *Atlas of Protein Sequence and Structure*, National Biomedical Research Foundation, pp. 353–358,1979); (2) a penalty of 3.0 for each gap and an additional 0.10 penalty for each symbol in each gap; and (3) no penalty for end gaps.

The primary amino acid structure of $CRF_2$ receptors may also be modified by forming covalent or aggregative conjugates with other chemical moieties, such as glycosyl groups, lipids, phosphate, acetyl groups and the like, or by creating amino acid sequence mutants. Covalent derivatives may be prepared by linking particular functional groups of $CRF_2R$ amino acid side chains or at the N- or C-termini. Other derivatives of $CRF_2R$ within the scope of this invention include covalent or aggregative conjugates of $CRF_2R$ or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). $CRF_2R$ protein fusions may also comprise peptides added to facilitate purification or identification of $CRF_2R$ (e.g., poly-His, which allows purification of the protein via, for example, a NTA nickel-chelating column), or FLAG (Hopp et al., *Bio/Technology* 6:1204–1210,1988). Other useful fusion proteins include luciferase, beta-galactosidase (Grey et al., *PNAS* 79:6598, 1982), trp E. (Itakura et al., *Science* 98:1056, 1977), and protein A (Ublen et al., *Gene* 23:369,1983). Within preferred embodiments, fusion proteins may include a site that is specifically recognized and cleaved, for example, by a collagenase (which cleaves x in the sequence Pro-x-Gly-Pro, where x is a neutral amino acid; see Keil et al., *FEBS Letters* 56:292–296, 1975). Factor Xa (which cleaves after arginine in the sequence Ile-Glu-Gly-Arg; see Nogai et al., *Methods Enzymol.* 153:461–481, 1987).

The present invention also includes $CRF_2R$ proteins with or without associated native-pattern glycosylation. Briefly, $CRF_2R$ expressed in yeast or mammalian expression systems, e.g., COS-7 cells, may be similar or significantly different in molecular weight and glycosylation pattern than the native molecules, depending upon the expression system. Expression of $CRF_2R$ nucleic acids in bacteria such as *E. coli* provides non-glycosylated molecules. Functional mutant analogs of mammalian $CRF_2R$ having inactivated N-glycosylation sites may be produced by oligonucleotide synthesis and ligation or by site-specific mutagenesis techniques. These analog proteins may be produced in a homogeneous, reduced-carbohydrate form in good yield using yeast expression systems. N-glycosylation sites in eukaryotic proteins are generally characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

Proteins which are biologically active and substantially similar to $CRF_2R$ proteins may also be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively, i.e., the most preferred substitute amino acids are those having physicochemical characteristics resembling those of the residue to be replaced.

When a substitution, deletion, or insertion strategy is adopted, the potential effect of the deletion or insertion on biological activity should be considered utilizing, for example, a binding assay such as that disclosed within the Examples. Particularly preferred regions wherein mutations, deletions, substitutions, or insertions may be accomplished include those which are not directly involved with binding of the receptor to its ligand. Such regions include all portions of the receptor, except the N-terminal extracellular domain, as well as the third intracellular loop between Th5 and Th6 (see e.g., Kobilka, *Ann. Rev. Neuro.* 15:87–114,1992).

Mutations in nucleotide sequences constructed for expression of proteins which are substantially similar to $CRF_2$ receptors should preferably preserve the reading frame phase of the coding sequences. Furthermore, the mutations should preferably not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at a target codon, or across a given site and the expressed $CRF_2R$ mutants screened for the biological activity.

Not all mutations in the nucleotide sequence which encodes $CRF_2R$ will be expressed in the final product. For example, nucleotide substitutions may be made to enhance expression primarily to avoid secondary structure loops in the transcribed mRNA, or to provide codons that are more readily translated by the selected host, e.g., the well-known, *E. coli* preference codons for *E. coli* expression.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures may be employed to provide an altered gene having particular codons altered according to the substitution, deletion, or insertion required. Representative methods of making the alterations set forth above are disclosed by Walder et al. (*Gene* 42:133, 1986); Bauer et al. (*Gene* 37:73,1985); Craik, *Bio Techniques, January* 1985, 12–19); Smith et al. (*Genetic Engineering: Principles and Methods*, Plenum Press, 1981); Sambrook et al. (*Molecular cloning: A Laboratory Manual*, 2d Ed., Cold Spring Harbor Laboratory Press, 1989); and U.S. Pat. Nos. 4,518,584 and 4,737,462.

$CRF_2$ receptors, as well as substantially similar derivatives or analogs may be used as therapeutic reagents, immunogens, reagents in receptor-based immunoassays, or as binding agents for affinity purification procedures of CRF, sauvagine, urotensin 1, other related molecules, or other binding ligands such as anti-$CRF_2$ receptor antibodies. Moreover, $CRF_2$ receptors of the present invention may be utilized to screen compounds for $CRF_2$ receptors agonist or antagonistic activity. $CRF_2$ receptor proteins may also be covalently bound through reactive side groups to various insoluble substrates, such as cyanogen bromine-activated, bisoxirane-activated, carbonyldiimidazole-activated, or tosyl-activated, agarose structures, or by adsorbing to polyolefin surfaces (with or without glutaraldehyde cross-linking). Once bound to a substrate, $CRF_2R$ may be used to selectively bind (for purposes of assay or purification) anti-$CRF_2R$ antibodies or CRF.

Isolation of CRF$_2$ Receptor cDNA Clones

As noted above, the present invention provides isolated nucleic acid molecules which encode CRF$_2$ receptors. Briefly, nucleic acid molecules which encode CRF$_2$ receptors of the present invention may be readily isolated from a variety of warm-blooded animals, including for example, humans, macaques, horses, cattle, sheep, pigs, dogs, cats, rats and mice. Particularly preferred tissues from which nucleic acid molecules which encode CRF$_2$ receptors may be isolated include brain and neural tissues such as the hypothalamus, hippocampus, and frontal cortex, as well as other tissues such as the lung, heart, skeletal muscle, or kidney. Nucleic acid molecules which encode CRF$_2$ receptors of the present invention may be readily isolated from conventionally prepared cDNA libraries (see, e.g., Sambrook et al., *Molecular Cloning: A Laboratory Manual*, 2d Ed., Cold Spring Harbor Laboratory Press, NY, 1989) or from commercially obtained libraries (e.g., Stratagene, LaJolla, Calif.) utilizing the disclosure provided herein. Particularly preferred methods for obtaining isolated nucleic acid molecules which encode CRF$_2$ receptors of the present invention are described in more detail below in Example 1 (see also Sequence I.D. Nos. 1 and 3).

As noted above, within particularly preferred embodiments of the invention, isolated nucleic acid molecules are provided which encode human CRF$_2$ receptors. Briefly, such nucleic acid molecules may be readily obtained by probing a human cDNA library either with a specific sequence as described below in Example 1, or with a rat sequence (e.g., Sequence I.D. Nos. 1 or 3) under conditions of low stringency (e.g., 35% formamide, 5×SSC, 5× Denharts, 0.1% SDS, 100 ug/ml salmon sperm nucleic acid, at 42° C. for 12 hours. This may be followed by extensive washing with 2×SSC containing 0.2% SDS at 50° C. Suitable cDNA libraries may be obtained from commercial sources (e.g., Stratagene, LaJolla, Calif.), or prepared utilizing standard techniques (see, e.g. Sambrook et al., supra).

Production of Recombinant CRF$_2$ Receptors

As noted above, the present invention also provides recombinant expression vectors which include synthetic or cDNA-derived nucleic acid fragments encoding CRF$_2$ receptors or substantially similar proteins, which are operably linked to suitable transcriptional or translation regulatory elements derived from mammalian, microbial, viral or insect genes. Such regulatory elements include a transcriptional promoter, an optional operator sequence to control transcription, a sequence encoding suitable mRNA ribosomal binding sites, and, within preferred embodiments, sequences which control the termination of transcription and translation. The ability to replicate in a host, usually conferred by an origin of replication, and a selection gene to facilitate recognition of transformants may additionally be incorporated. Nucleic acid regions are operably linked when they are functionally related to each other. For example, nucleic acid for a signal peptide (secretory leader) is operably linked to nucleic acid for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

Expression vectors may also contain nucleic acid sequences necessary to direct the secretion of a polypeptide of interest. Such nucleic acid sequences may include at least one secretory signal sequence. Representative examples of secretory signals include the alpha factor signal sequence (pre-pro sequence; Kurjan and Herskowitz, *Cell* 30:933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3:439–447,1983), the α-1-antitrypsin signal sequence (Kurachi et al., *Proc. Natl. Acad. Sci. USA* 78:6826–6830, 1981), the β-2 plasmin inhibitor signal sequence (Tone et al., *J. Biochem.* (Tokyo) 102:1033–1042, 1987), the tissue plasminogen activator signal sequence (Pennica et al., *Nature* 301:214–221,1983), the *E. coli* PhoA signal sequence (Yuan et al., *J. Biol. Chem.* 265:13528–13552, 1990) or any of the bacterial signal sequences reviewed, for example, by Oliver (*Ann. Rev. Microbiol.* 39:615–649,1985). Alternatively, a secretory signal sequence may be synthesized according to the rules established, for example, by von Heinje (*Eur. J. Biochem.* 133:17–21, 1983; *J. Mol. Biol.* 184:99–105, 1985; *Nuc. Acids Res.* 14:4683–4690, 1986).

For expression, a nucleic acid molecule encoding a CRF$_2$ receptor is inserted into a suitable expression vector, which in turn is used to transform or transfect appropriate host cells for expression. Host cells for use in practicing the present invention include mammalian, avian, plant, insect, bacterial and fungal cells. Preferred eukaryotic cells include cultured mammalian cell lines (e.g., rodent or human cell lines) and fungal cells, including species of yeast (e.g., *Saccharomyces* spp., particularly *S. cerevisiae, Schizosaccharomyces* spp., or *Kluyveromyces* spp.) or filamentous fungi (e.g., *Aspergillus* spp., *Neurospora* spp.). Strains of the yeast *Saccharomyces cerevisiae* are particularly preferred. Methods for producing recombinant proteins in a variety of prokaryotic and eukaryotic host cells are generally known in the art (see "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.) Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned nucleic acid sequences which must be transfected into the host cell may be minimized and overall yield of biologically active protein may be maximized.

Suitable yeast vectors for use in the present invention include YRp7 (Struhl et al., *Proc. Natl. Acad. Sci. USA* 76:1035–1039,1978), YEp13 (Broach et al., *Gene* 8:121–133,1979), POT vectors (Kawasaki et al., U.S. Pat. No. 4,931,373, which is incorporated by reference herein), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8:17,1979), HIS3 (Struhl et al., ibid.) or POT1 (Kawasaki et al., ibid.). Another suitable selectable marker is the CAT gene, which confers chloramphenicol resistance on yeast cells.

Promoters suitable for use in yeast include promoters from yeast glycolytic genes (Hitzeman et al., *J. Biol. Chem.*

255:12073–12080,1980; Alber and Kawasaki, *J. Mol. Appl. Genet* 1:419–434, 1982; Kawasaki, U.S. Pat. No. 4,599,311) or alcohol dehydrogenase genes (Young et al., in *Genetic Engineering of Microorganisms for Chemicals*, Hollaender et al. (eds.), p. 355, Plenum, New York, 1982; Ammerer, *Meth. Enzymol.* 101:192–201,1983). In this regard, particularly preferred promoters are the TPI1 promoter (Kawasaki, U.S. Pat. No. 4,599,311,1986) and the ADH2-4$^c$ promoter (Russell et al., *Nature* 304:652–654,1983; Irani and Kilgore, U.S. patent application Ser. No. 07/784,653, which is incorporated herein by reference). The expression units may also include a transcriptional terminator, such as the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4:2093–2099,1985) and the tpiA promoter. An example of a suitable terminator is the ADH3 terminator (McKnight et al., ibid., 1985). The expression units utilizing such components are cloned into vectors that are capable of insertion into the chromosomal nucleic acid of Aspergillus.

Techniques for transforming fungi are well known in the literature, and have been described, for instance, by Beggs (ibid.), Hinnen et al. (*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169,1983). The genotype of the host cell will generally contain a genetic defect that is complemented by the selectable marker present on the expression vector. Choice of a particular host and selectable marker is well within the level of ordinary skill in the art. To optimize production of the heterologous proteins in yeast, for example, it is preferred that the host strain carries a mutation, such as the yeast pep4 mutation (Jones, *Genetics* 85:23–33,1977), which results in reduced proteolytic activity.

In addition to fungal cells, cultured mammalian cells may be used as host cells within the present invention. Preferred cultured mammalian cells for use in the present invention include the COS-1 (ATCC No. CRL 1650), COS-7 (ATCC No. CRL 1651), BHK (ATCC No. CRL 1632), and 293 (ATCC No. CRL 1573; Graham et al., *J. Gen. Virol.* 36:59–72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, FEBS 229(1):175–178,1988).

Mammalian expression vectors for use in carrying out the present invention should include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864,1981). Cellular promoters include the mouse metallothionein-1 promoter (Palmiter et al., U.S. Pat. No. 4,579,821), a mouse $V_J$ promoter (Bergman et al., *Proc. Natl. Acad. Sci. USA* 81:7041–7045,1983; Grant et al., *Nuc. Acids Res.* 15:5496,1987) and a mouse $V_H$ promoter (Loh et al., *Cell* 33:85–93,1983). A particularly preferred promoter is the major late promoter from Adenovirus 2 (Kaufman and Sharp, *Mol. Cell. Biol.* 2:1304–13199, 1982). Such expression vectors may also contain a set of RNA splice sites located downstream from the promoter and upstream from the nucleic acid sequence encoding the peptide or protein of interest. Preferred RNA splice sites may be obtained from SV40, adenovirus and/or immunoglobulin genes. Alternatively, within certain embodiments RNA splice sites may be located downstream from the nucleic acid sequence encoding the peptide or protein of interest. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse I enhancer (Gillies, *Cell* 33:717–728, 1983). Expression vectors may also include sequences encoding the adenovirus VA RNAs. Suitable vectors can be obtained from commercial sources (e.g., Invitrogen, San Diego, Calif.; Stratagene, La Jolla, Calif.).

Cloned nucleic acid sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456,1973), electroporation (Neumann et al., *EMBO J.* 1:841–845,1982), or DEAE-dextran mediated transfection (Ausubel et al. (eds.), *Current Protocols in Molecular Biology*, John Wiley and Sons, Inc., NY, 1987), which are incorporated herein by reference. To identify cells that have stably integrated the cloned nucleic acid, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate vector at the same time as the CRF$_2$ receptor sequence, or they may be introduced on the same vector. If on the same vector, the selectable marker and the CRF$_2$ receptor sequence may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional nucleic acid, known as "carrier nucleic acid" to the mixture which is introduced into the cells.

Transfected mammalian cells are allowed to grow for a period of time, typically 1–2 days, to begin expressing the nucleic acid sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells which satisfy these criteria may then be cloned and scaled up for production.

Preferred prokaryotic host cells for use in carrying out the present invention include *Escherichia coli* (e.g., *E. coli* HB101, *E. coli* DH1, *E. coli* MRC1 and *E. coli* W3110), although *Bacillus*, *Pseudomonas*, and *Streptomyces* and other genera are also useful. Techniques for transforming these hosts and expressing foreign nucleic acid sequences cloned therein are well known in the art (see, e.g., Maniatis et al., *Molecular Cloning: A Laboratory Manual*, Cold Spring Harbor Laboratory, 1982; or Sambrook et al., supra). Vectors used for expressing cloned nucleic acid sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage k (Queen, *J. Mol. Appl. Genet.* 2:1–10, 1983) promoter systems. Plasmids useful for transforming bacteria include pBR322 (Bolivar et al., *Gene* 2:95–113, 1977), the pUC plasmids (Messing, *Meth. Enzymol.* 101: 20–78, 1983; Vieira and Messing, *Gene* 19:259–268, 1982), pCQV2 (Queen, ibid.), pMAL-2 (New England Biolabs, Beverly, Mass.) and derivatives thereof. Plasmids may contain both viral and bacterial elements.

Given the teachings provided herein, promoters, terminators and methods for introducing expression vectors encoding $CRF_2$ receptors of the present invention into plant, avian and insect cells would be evident to those of skill in the art. The use of baculoviruses, for example, as vectors for expressing heterologous nucleic acid sequences in insect cells has been reviewed by Atkinson et al. (*Pestic. Sci.* 28:215–224,1990). In addition, the use of *Agrobacterium rhizogenes* as vectors for expressing genes in plant cells has been reviewed by Sinkar et al. (*J. Biosci. (Bangalore)* 11:47–58, 1987).

Host cells containing nucleic acid molecules of the present invention are then cultured to express a nucleic acid molecule encoding a $CRF_2$ receptor. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the nucleic acid molecules by, for example, drug selection or deficiency in an essential nutrient which is complemented by the selectable marker on the nucleic acid construct or co-transfected with the nucleic acid construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the $CRF_2$ receptors of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M. Cultured mammalian cells are generally cultured in commercially available serum-containing or serum-free media. Selection of a medium and growth conditions appropriate for the particular cell line used is within the level of ordinary skill in the art.

$CRF_2$ receptors may also be expressed in non-human transgenic animals, particularly transgenic warm-blooded animals. Methods for producing transgenic animals, including mice, rats, rabbits, sheep and pigs, are known in the art and are disclosed, for example, by Hammer et al. (*Nature* 315:680–683, 1985), Palmiter et al. (*Science* 222:809–814, 1983), Brinster et al. (*Proc. Natl. Acad. Sci. USA* 82:4438–4442, 1985), Palmiter and Brinster (*Cell* 41:343–345,1985) and U.S. Pat. No. 4,736,866, which are incorporated herein by reference. Briefly, an expression unit, including a nucleic acid sequence to be expressed together with appropriately positioned expression control sequences, is introduced into pronuclei of fertilized eggs. Introduction of nucleic acid is commonly done by microinjection. Integration of the injected nucleic acid is detected by blot analysis of nucleic acid from tissue samples, typically samples of tail tissue. It is generally preferred that the introduced nucleic acid be incorporated into the germ line of the animal so that it is passed on to the animal's progeny.

Within particularly preferred embodiments of the invention, "knockout" animals may be developed from embryonic stem cells through the use of homologous recombination (Capecchi, *Science* 244:1288–1292,1989) or antisense oligonucleotide (Stein and Chen, *Science* 261(5124):1004–1012, 1993; Milligan et al., *Semin. Conc. Biol.* 3(6):391–398, 1992).

Within a preferred embodiment of the invention, a transgenic animal, such as a mouse, is developed by targeting a mutation to disrupt a $CRF_2$ receptor sequence (see Mansour et al., "Disruption of the proto-oncogene int-2 in mouse embryo-derived stem cells: A general strategy for targeting mutations to non-selectable genes," *Nature* 336:348–352, 1988). Such animals may readily be utilized as a model to study the role of the $CRF_2$ receptor in metabolism.

$CRF_2$ Receptor Peptides

As noted above, the present invention also provides $CRF_2$ receptor peptides. Within the context of the present invention, $CRF_2$ receptor peptides should be understood to include portions of a $CRF_2$ receptor or derivatives thereof discussed above, which do not contain transmembrane domains, and which are at least 8, and more preferably 10 or greater amino acids in length. Briefly, the structure of the $CRF_2$ receptor as well as putative transmembrane domains may be predicted from the primary translation products using the hydrophobicity plot function of, for example, P/C Gene or Intelligenetics Suite (Intelligenetics, Mt. View, Calif.), or according to the methods described by Kyte and Doolittle (*J. Mol. Biol.* 157:105–132, 1982). While not wishing to be bound by a graphical representation, based upon this hydrophobicity analysis, $CRF_2$ receptors are believed to have the general structure shown in FIGS. 1 and 2. In particular, these receptors are believed to comprise an extracellular amino-terminal domain, three extracellular loop domains and four intracellular loop domains each separated by a transmembrane domain.

Within one aspect of the invention, isolated $CRF_2$ receptor peptides are provided comprising the extracellular amino-terminal domain of a $CRF_2$ receptor. Within a preferred embodiment, an isolated $CRF_2$ receptor peptide is provided comprising the sequence of amino acids shown in Sequence I.D. No. 4, from amino acid 1 to amino acid number 118. Within another embodiment, an isolated CRF2 receptor peptide is provided comprising the sequence of amino acids shown in Sequence ID No. 2 from amino acid number 1 to amino acid number 138.

$CRF_2$ receptor peptides may be prepared by, among other methods, culturing suitable host/vector systems to produce the recombinant translation products of the present invention. Supernatants from such cell lines may then be treated by a variety of purification procedures in order to isolate the $CRF_2$ receptor peptide. For example, the supernatant may be first concentrated using commercially available protein concentration filters, such as an Amicon or Millipore Pellicon ultrafiltration unit. Following concentration, the concentrate may be applied to a suitable purification matrix such as, for example, CRF or an anti-$CRF_2$ receptor antibody bound to a suitable support. Alternatively, anion or cation exchange resins may be employed in order to purify the receptor or peptide. Finally, one or more reversed-phase high performance liquid chromatography (RP-HPLC) steps may be employed to further purify the $CRF_2$ receptor peptide.

Alternatively, $CRF_2$ receptor peptides may also be prepared utilizing standard polypeptide synthesis protocols, and purified utilizing the above-described procedures.

A $CRF_2$ receptor peptide is deemed to be "isolated" or purified within the context of the present invention, if only a single band is detected subsequent to SDS-polyacrylamide gel analysis followed by staining with Coomassie Brilliant Blue.

Antibodies to $CRF_2$ Receptors

Within one aspect of the present invention, $CRF_2$ receptors, including derivatives thereof, as well as portions or fragments of these proteins such as the $CRF_2$ receptor peptides discussed above, may be utilized to prepare antibodies which specifically bind to $CRF_2$ receptors. Within the context of the present invention the term "antibodies" includes polyclonal antibodies, monoclonal antibodies, fragments thereof such as $F(ab')_2$ and Fab fragments, as well as recombinantly produced binding partners. These binding partners incorporate the variable regions from a gene which encodes a specifically binding monoclonal antibody. Antibodies are defined to be specifically binding if they bind to the $CRF_2$ receptor with a $K_a$ of greater than or equal to $10^7$ $M^{-1}$. The affinity of a monoclonal antibody or binding partner may be readily determined by one of ordinary skill in the art (see Scatchard, *Ann. N.Y. Acad. Sci.* 51:660–672, 1949).

Polyclonal antibodies may be readily generated by one of ordinary skill in the art from a variety of warm-blooded animals such as horses, cows, goats, sheep, dogs, chickens, rabbits, mice, or rats. Briefly, the $CRF_2$ receptor is utilized to immunize the animal through intraperitoneal, intramuscular, intraocular, or subcutaneous injections. The immunogenicity of a $CRF_2$ receptor or $CRF_2$ receptor peptide may be increased through the use of an adjuvant such as Freund's complete or incomplete adjuvant. Following several booster immunizations, small samples of serum are collected and tested for reactivity to the $CRF_2$ receptor. A variety of assays may be utilized in order to detect antibodies which specifically bind to a $CRF_2$ receptor. Exemplary assays are described in detail in *Antibodies: A Laboratory Manual*, Harlow and Lane (eds.), Cold Spring Harbor Laboratory Press, 1988. Representative examples of such assays include: Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also *Antibodies: A Laboratory Manual*, supra). Particularly preferred polyclonal antisera will give a signal that is at least three times greater than background. Once the titer of the animal has reached a plateau in terms of its reactivity to the $CRF_2$ receptor, larger quantities of polyclonal antisera may be readily obtained either by weekly bleedings, or by exsanguinating the animal.

Monoclonal antibodies may also be readily generated using well-known techniques (see U.S. Patent Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, within one embodiment a subject animal such as a rat or mouse is injected with a form of $CRF_2$ receptor suitable for generating an immune response against the $CRF_2$ receptor. Representative examples of suitable forms include, among others, cells which express the $CRF_2$ receptor, or peptides which are based upon the $CRF_2$ receptor sequence. Additionally, many techniques are known in the art for increasing the resultant immune response, for example, by coupling the receptor or receptor peptides to another protein such as ovalbumin or keyhole limpet hemocyanin (KLH), or through the use of adjuvants such as Freund's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for binding to the $CRF_2$ receptor using assays as described above. Additional immunizations may also be accomplished until the animal has plateaued in its reactivity to the $CRF_2$ receptor. The animal may then be given a final boost of $CRF_2$ receptor or $CRF_2$ receptor peptide, and three to four days later sacrificed. At this time, the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the $CRF_2$ receptor that is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Agl.2.3 (ATCC No. CRL 1631), and YB2/0 (ATCC No. CRL 1662). Particularly preferred fusion lines include NS-1 (ATCC No. TIB 18) and P3×63-Ag 8.653 (ATCC No. CRL 1580), which may be utilized for fusions with either mouse, rat, or human cell lines. Fusion between the myeloma cell line and the cells from the immunized animal may be accomplished by a variety of methods, including the use of polyethylene glycol (PEG) (see Antibodies: A Laboratory Manual, Harlow and Lane (eds.), Cold Spring Harbor Laboratory Press, 1988) or electrofusion (see Zimmerman and Vienken, *J. Membrane Biol.* 67:165–182, 1982).

Following the fusion, the cells are placed into culture plates containing a suitable medium, such as RPMI 1640 or DMEM (Dulbecco's Modified Eagles Medium) (JRH Biosciences, Lenexa, Kans.). The medium may also contain additional ingredients, such as Fetal Bovine Serum ("FBS," i.e., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine) (Sigma Chemical Co., St. Louis, Mo.). After about seven days, the resulting fused cells or hybridomas may be screened in order to determine the presence of antibodies which recognize the $CRF_2$ receptor. Following several clonal dilutions and reassays, a hybridoma producing antibodies which bind to $CRF_2$ receptor may be isolated.

Other techniques may also be utilized to construct monoclonal antibodies (see Huse et al., "Generation of a Large Combinational Library of the Immunoglobulin Repertoire in Phage Lambda," *Science* 246:1275–1281, December 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989; see also Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population and utilized to create heavy and light chain immunoglobulin cDNA expression libraries in the kIMMUNOZAP(H) and kIMMUNOZAP(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant nucleic acid techniques to incorporate the variable regions of a gene which encodes a specifically binding antibody. The construction of these proteins may be readily accomplished by one of ordinary skill in the art (see Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann et al., "Reshaping Human Antibodies for Therapy," Nature 332: 323–327, 1988; Roberts et al., "Generation of an Antibody with Enhanced Affinity and Specificity for its Antigen by Protein Engineering," *Nature* 328:731–734,1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397,1989; see also, U.S. Pat. No. 5,132,405 entitled "Biosynthetic Antibody Binding Sites"), given the disclosure provided herein. Briefly, within one embodiment, nucleic acid molecules encoding $CRF_2$ receptor-specific antigen binding domains are amplified from hybridomas which produce a specifically binding monoclonal antibody, and inserted directly into the genome of a cell which produces human antibodies (see Verhoeyen et al., supra; see also Reichmann et al., supra). This technique allows the antigen-binding site of a specifically binding mouse or rat monoclonal antibody to be transferred into a human antibody. Such antibodies are preferable for therapeutic use in humans because they are not as antigenic as rat or mouse antibodies.

Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or $CRF_2$ receptor binding domain of the antibody may be found in the variable region of the antibody. Furthermore, nucleic acid sequences which encode smaller portions of the antibody or variable regions which specifically bind to mammalian $CRF_2$ receptor may also be utilized within the context of the present invention. These portions may be readily tested for binding specificity to the $CRF_2$ receptor utilizing assays described below.

Within a preferred embodiment, genes which encode the variable region from a hybridoma producing a monoclonal antibody of interest are amplified using oligonucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{HC}$, $V_{Hd}$, $C_{H1}$, $V_L$ and $C_L$ regions. These primers may be utilized to amplify heavy or light chain variable regions, which may then be inserted into vectors such as IMMUNOZAP*(H) or IMMUNOZAP*(L) (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426,1988).

Other "antibodies" which may also be prepared utilizing the disclosure provided herein, and thus which are also deemed to fall within the scope of the present invention include humanized antibodies (e.g., U.S. Pat. No. 4,816,567 and WO 94/10332), microbodies (e.g., WO 94/09817) and transgenic antibodies (e.g., GB 2 272 440).

Once suitable antibodies have been obtained, they may be isolated or purified by many techniques well known to those of ordinary skill in the art (see *Antibodies: A Laboratory Manual*, supra). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components."

Antibodies of the present invention have many uses. For example, antibodies may be utilized in flow cytometry to sort $CRF_2$ receptor-bearing cells, or to histochemically stain $CRF_2$ receptor-bearing tissues. Briefly, in order to detect $CRF_2$ receptors on cells, the cells (or tissue) are incubated with a labeled antibody which specifically binds to $CRF_2$ receptors, followed by detection of the presence of bound antibody. These steps may also be accomplished with additional steps such as washings to remove unbound antibody. Representative examples of suitable labels, as well as methods for conjugating or coupling antibodies to such labels are described in more detail below.

In addition, purified antibodies may also be utilized therapeutically to block the binding of CRF or other $CRF_2$ receptor substrates such as sauvagine or urotensin I to the $CRF_2$ receptor in vitro or in vivo. Briefly, blocking antibodies are those antibodies that bind to $CRF_2$ receptor epitopes in such a way as to prevent CRF from binding to the receptor, or to prevent CRF from effecting signal transduction. As noted above, a variety of assays may be utilized to detect antibodies which block or inhibit the binding of CRF to the $CRF_2$ receptor, including inter alia, inhibition and competition assays noted above. Within one embodiment, monoclonal antibodies (prepared as described above) are assayed for binding to the $CRF_2$ receptor in the absence of CRF, as well as in the presence of varying concentrations of CRF. Blocking antibodies are identified as those which, for example, bind to $CRF_2$ receptors and, in the presence of CRF, block or inhibit the binding of CRF to the $CRF_2$ receptor.

Antibodies of the present invention may also be coupled or conjugated to a variety of other compounds for either diagnostic or therapeutic use. Such compounds include, for example, toxic molecules, molecules which are nontoxic but which become toxic upon exposure to a second compound, and radionuclides. Representative examples of such molecules are described in more detail below.

Antibodies which are to be utilized therapeutically are preferably provided in a therapeutic composition comprising the antibody or binding partner and a physiologically acceptable carrier or diluent. Suitable carriers or diluents include, among others, neutral buffered saline or saline, and may also include additional excipients or stabilizers such as buffers, sugars such as glucose, sucrose, or dextrose, chelating agents such as EDTA, and various preservatives.

Isolation and Use of Compounds which Bind the $CRF_2$ Receptor, Including Agonists and Antagonists As noted above, the present invention provides a variety of methods for detecting the presence of compounds which bind to $CRF_2$ receptors. For example, within one embodiment of the invention methods for detecting such compounds are provided, comprising the steps of (a) exposing one or more compounds to cells that express $CRF_2$ receptors under conditions and for a time sufficient to allow binding of the compounds to the receptors, and (b) isolating compounds which bind to the receptors, such that the presence of a compound which binds to a $CRF_2$ receptor may be detected. As utilized herein, conditions sufficient to allow binding of compounds to cells that express $CRF_2$ receptors generally range from pH 6.8 to 7.5, and include a suitable buffer such as Tris-HCl or PBS, either with or without bovine serum albumin ("BSA"). Such buffers may also include magnesium at a concentration of 5 to 20 mM, as well as protease inhibitors such as bacitracin or aprotinin. Sufficient time for the binding of compounds to cells that express $CRF_2$ receptors generally ranges from between 30 and 150 minutes after exposure.

Within other aspects of the present invention, methods for detecting the presence of a compound which binds to $CRF_2$ receptors are provided, comprising the steps of (a) exposing one or more compounds to a $CRF_2$ receptor N-terminal extracellular domain under conditions and for a time sufficient to allow binding of a compound to the N-terminal extracellular domain, and (b) isolating compounds which bind to the $CRF_2$ receptor N-terminal extracellular domain, such that the presence of a compound which binds to a $CRF_2$ receptor may be detected. Such assays may take a variety of forms, including for example, as Enzyme Linked ImmunoSorbent Assay, "Sandwich" assay, or the like. Within one embodiment, the compounds are labeled with an agent selected from the group consisting of fluorescent molecules, enzymes, and radionuclides.

In addition to providing assays which detect the presence of compounds which bind to $CRF_2$ receptors, the present invention also provides methods for detecting both $CRF_2$ receptor agonists and $CRF_2$ receptor antagonists. Within the context of the present invention, $CRF_2$ receptor agonists should be understood to refer to molecules that are capable of binding to the cell-surface receptor, thereby stimulating a response pathway within the cell. In contrast, $CRF_2$ receptor antagonists should be understood to refer to molecules that are capable of binding to a $CRF_2$ receptor, but which prevent stimulation, or exhibit greatly reduced stimulation of a response pathway within the cell. Various assays may be utilized given the disclosure provided herein in order to screen or select for CRF agonists and antagonists.

For example, within one aspect of the present invention, methods are provided for determining whether a selected compound is a $CRF_2$ receptor agonist or antagonist, comprising the steps of (a) exposing a selected compound to cells which express $CRF_2$ receptors under conditions and for a time sufficient to allow binding of the compound and an associated response in intracellular levels of cAMP, and (b) detecting either an increase or decrease in the level of intracellular cAMP, and thereby determining whether the selected compound is a $CRF_2$ receptor agonist or antagonist.

cAMP may be readily measured using methods which are well known in the art, including, for example, methods described by Salomon et al. (*Anal. Biochem.* 58:541–548, 1976) or Krishna et al. (*J. Pharmacol. Exp. Ther.* 163:379, 1968), or, preferably, using commercially available kits such as the Scintillation Proximity Assay Kit from Amersham Corporation, or the $^{125}I$ RIA cAMP determination kit from Incstar Corporation (Stillwater, Minnesota). The Scintillation Proximity Assay Kit measures the production of cAMP by competition of iodinated-cAMP with anti-cAMP antibodies.

Within other aspects, methods are provided for detecting the presence of a $CRF_2$ receptor agonist or antagonist in a pool of compounds, comprising the steps of (a) exposing a pool of compounds to cells which express $CRF_2$ receptors under conditions and for a time sufficient to allow binding of the compound and an associated response in intracellular levels of cAMP, and (b) isolating compounds which either increase or decrease the intracellular level of cAMP, such that the presence of a $CRF_2$ receptor agonist or antagonist may be detected.

Within another aspect, methods for determining whether a selected compound is a $CRF_2$ receptor antagonist are provided, comprising the steps of (a) exposing a selected compound in the presence of a $CRF_2$ receptor agonist to a recombinant $CRF_2$ receptor coupled to a response pathway under conditions and for a time sufficient to allow binding of the compound to the receptor and an associated response through the pathway, and (b) detecting a reduction in the stimulation of the response pathway resulting from the binding of the compound to the $CRF_2$ receptor, relative to the stimulation of the response pathway by the $CRF_2$ receptor agonist alone, and therefrom determining the presence of a $CRF_2$ antagonist. Within other aspects, methods are provided for determining whether a selected compound is a $CRF_2$ receptor agonist, comprising the steps of (a) exposing a selected compound to a recombinant $CRF_2$ receptor coupled to a response pathway under conditions and for a time sufficient to allow binding of the compound to the receptor and an associated response through the pathway, and (b) detecting an increase in stimulation of the response pathway resulting from the binding of the compound to the $CRF_2$ receptor, and therefrom determining the presence of a $CRF_2$ receptor agonist.

Within particularly preferred embodiments of the invention, the response pathway is a membrane-bound adenylate cyclase response pathway, and the step of detecting comprises measuring the increase or decrease in cAMP production by the membrane-bound adenylate cyclase response pathway. Adenylate cyclase activity assays may be carried out, for example, utilizing method(s) described below in the Examples. Generally, such methods measure the level of stimulation of cAMP relative to known agonists (e.g., sauvagine, urotensin I or CRF), and generally involve exposing a preparation of cells which express a biologically active $CRF_2$ receptor to the selected compound in the presence of radiolabelled ATP.

Within a further embodiment of the invention, the response pathway includes a reporter system, such as luciferase, or β-galactosidase (see Konig et al., *Mol. and Cell. Neuro.* 2:331–337, 1991). For examples, within one embodiment of the invention an expression vector is provided comprising a cyclic AMP response element such as a proenkephalin cyclic AMP response element, operably linked to β-galactosidase or luciferase cDNA. The expression vector is then stably transfected into a host cell, and the host cell then transfected with a second expression vector which expresses a $CRF_2$ receptor. Upon activation of the response pathway, elevated cAMP levels induce the expression of the reporter product, such as the β-galactosidase or luciferase. If the reporter product is luciferase, it is then exposed to luciferin, and photons which are released during the oxidation of luciferin by the luciferase are measured.

A variety of compounds may be screened utilizing such methods. Representative examples include blocking antibodies discussed above, $CRF_2$ receptor peptides, and CRF analogs (including both peptide and non-peptide ligands). In addition, large numbers of CRF analogs may be generated by saturation mutagenesis of nucleic acid sequences encoding CRF (e.g., Little, *Gene* 88:113–115, 1990; Hembers et al., *Gene* 88:143–151,1989), by segment-directed mutagenesis (e.g., Shortle et al., *Proc. Natl. Acad. Sci. USA* 77:5375–5379,1980), by forced nucleotide misincorporation (e.g., Liao and Wise, *Gene* 88:107–111,1990), or by use of randomly mutagenized oligonucleotides (Hutchison et al., *Proc. Natl. Acad. Sci. USA* 83:710–714,1986). Individual transformants expressing a $CRF_2$ analog may then be cloned as discussed above, or pooled.

Other compounds which may also be screened utilizing methods of the present invention, include chemical compounds which are known and either available commercially (e.g., from Sigma Chemical Co., St. Louis, Mo.) or readily synthesized by one of skill in the art. In addition, numerous novel compositions which are provided in combinatorial libraries may also be readily screened utilizing the methods described herein, including for example organic and protein or peptide libraries (see e.g., Gold and Tuerk, U.S. Pat. No. 5,270,163; and Ladner et al., U.S. Pat. Nos. 5,096,815, 5,198,346, and 5,223,409).

Within a preferred aspect of the invention, the screening of chemical libraries (including peptide, small organic molecule or combinatorial chemistry-derived compound libraries) can be assessed in a high-throughput format using the expressed $CRF_2$ receptors. More specifically, within one embodiment of the invention, a high throughput receptor binding assay may be performed in a 96-well plate and is automated using the BIOMEK 2000 (Beckman, Fullerton Calif.). Briefly, $1 \times 10^5$ cells transfected with the $CRF_2$ receptor are grown in each well. To this, 0.05 ml of assay buffer (Dulbecco's Phosphate Buffered Saline, 10 mM $MgCl_2$, 20 μM Bacitracin) with or without unlabeled r/hCRF (final concentration, 1 μM) is added in duplicate to determine total binding and non-specific binding. In singlets, 0.05 ml of compounds (mixtures from 1 to 30 compounds) are added to each well in addition to 0.05 ml of either [$^{125}$I]-oCRF or [$^{125}$I]-r/hCRF (final concentration ~200 pM). The mixture is incubated for 2 hours at 22° C. Since the transfected cells are adherent, a centrifugation step to separate membrane-bound CRF is not necessary. Next, the fluid is aspirated and the cells are washed three times with approximately 0.9 ml of PBS. After the third wash and aspiration, 0.2 ml of 4M guanidine thiocyanate is added to each well to solubilize the tissue. An aliquot (0.15 ml) of the solubilized sample is monitored in a gamma counter for radioactivity at approximately 80% efficiency. Compounds which demonstrate $\geq 50\%$ inhibition of [$^{125}$I]CRF binding are tested in a full dose response competition assay to determine the affinity of these compounds (Ki value) at the $CRF_2$ receptor.

Once purified partially, or to homogeneity, as desired, both $CRF_2$ receptor agonists and antagonists may be used therapeutically. Generally substantially pure recombinant CRF antagonists of at least about 50% homogeneity are preferred, at least about 70%–80% homogeneity more preferred, and 95%–99% or more homogeneity most preferred, particularly for pharmaceutical uses. In general, the antagonists may be administered intradermally ("i.d."), intracranially ("i.c."), intraperitoneally ("i.p."), intrathecally ("i.t."), intravenously ("i.v."), subcutaneously ("s.c."), intramuscularly ("i.m.") or directly into a tumor. Typically, the antagonists are present as free bases or as acid salts. Suitable salts should be pharmaceutically acceptable. Representative examples include metal salts, alkali and alkaline earth metal salts such as potassium or sodium salts. Other pharmaceutically acceptable salts include citric, succinic, lactic, hydrochloric and hydrobromic acids. Parenteral compositions may be formulated in aqueous isotonic solutions of between pH Labels The nucleic acid molecules, antibodies, $CRF_2$ receptors, and $CRF_2$ receptor agonists and antagonists of the present invention may be labeled or conjugated (either through covalent or non-covalent means) to a variety of labels or other molecules, including for example, fluorescent markers, enzyme markers, toxic molecules, molecules which are nontoxic but which become toxic upon exposure to a second compound, and radionuclides.

Representative examples of fluorescent labels suitable for use within the present invention include, for example, Fluorescein Isothiocyanate (FITC), Rodamine, Texas Red, Luciferase and Phycoerythrin (PE). Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881,1970; and Goding, "Conjugation of Antibodies with Fluorochromes: Modification to the Standard Methods," *J. Immunol. Methods* 13:215–226,1970.) For histochemical staining, HRP, which is preferred, may be conjugated to the purified antibody according to the method of Nakane and Kawaoi ("Peroxidase-Labeled Antibody: A New Method of Conjugation," *J. Histochem. Cytochem.* 22:1084–1091,1974; see also, Tijssen and Kurstak, "Highly Efficient and Simple Methods for Preparation of Peroxidase and Active Peroxidase Antibody Conjugates for Enzyme Immunoassays," *Anal. Biochem.* 136:451–457, 1984).

Representative examples of enzyme markers or labels include alkaline phosphatase, horse radish peroxidase, and β-galactosidase. Representative examples of toxic molecules include ricin, abrin, diphtheria toxin, cholera toxin, gelonin, pokeweed antiviral protein, tritin, Shigella toxin, and Pseudomonas exotoxin A. Representative examples of molecules which are nontoxic, but which become toxic upon exposure to a second compound include thymidine kinases such as HSVTK and VZVTK. Representative examples of radionuclides include Cu-64, Ga-67, Ga-68, Zr-89, Ru-97, Tc-99m, Rh-105, Pd-109, In-111, I123, I125, I131, Re-186, Re-188, Au-198, Au-1, Pb-203, At-211, Pb-212 and Bi-212.

As will be evident to one of skill in the art given the disclosure provided herein, the above described nucleic acid molecules, antibodies, $CRF_2$ receptors, $CRF_2$ receptor peptides and $CRF_2$ receptor agonists and antagonists may also be labeled with other molecules such as colloidal gold, as well either member of a high affinity binding pair (e.g., avidin-biotin).

Diaqnostic Use Of $CRF_2$ Receptor Sequences

Within another aspect of the present invention, probes and primers are provided for detecting $CRF_2$ receptors. Within one embodiment of the invention, probes are provided which are capable of hybridizing to $CRF_2$ receptor nucleic acid or RNA. For purposes of the present invention, probes are "capable of hybridizing" to $CRF_2$ receptor nucleic acid if they hybridize to Sequence I.D. Nos. 1 or 3 under conditions of moderate or high stringency (see Sambrook et al., supra); but not to CRF receptor nucleic acids. Preferably, the probe may be utilized to hybridize to suitable nucleotide sequences in the presence of 50% formamide, 5×SSPE, 5× Denhardt's, 0.1% SDS and 100 ug/ml Salmon Sperm nucleic acid at 42° C., followed by a first wash with 2×SSC at 42° C., and a second wash with 0.2×SSC at 55 to 60° C.

Probes of the present invention may be composed of either deoxyribonucleic acids (DNA) ribonucleic acids (RNA), nucleic acid analogues, or any combination of these, and may be as few as about 12 nucleotides in length, usually about 14 to 18 nucleotides in length, and possibly as large as the entire sequence of the $CRF_2$ receptor. Selection of probe size is somewhat dependent upon the use of the probe. For example, in order to determine the presence of various polymorphic forms of the $CRF_2$ receptor within an individual, a probe comprising virtually the entire length of the $CRF_2$ receptor coding sequence is preferred. $CRF_2$ receptor probes may be utilized to identify polymorphisms linked to the $CRF_2$ receptor gene (see, for example, Weber, *Genomics* 7:524–530,1990; and Weber and May, *Amer. J. Hum. Gen.* 44:388–396,1989). Such polymorphisms may be associated with inherited diseases such as diabetes.

Probes may be constructed and labeled using techniques which are well known in the art. Shorter probes of, for example, 12 or 14 bases may be generated synthetically. Longer probes of about 75 bases to less than 1.5 kb are preferably generated by, for example, PCR amplification in the presence of labeled precursors such as $^{32}$P-dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells (see Sambrook et al., supra).

Probes may be labeled by a variety of markers, including, for example, radioactive markers, fluorescent markers, enzymatic markers, and chromogenic markers. The use of $^{32}$P is particularly preferred for marking or labeling a particular probe.

Probes of the present invention may also be utilized to detect the presence of a $CRF_2$ receptor mRNA or nucleic acid within a sample. However, if $CRF_2$ receptors are present in only a limited number, or if it is desired to detect a selected mutant sequence which is present in only a limited number, or if it is desired to clone a $CRF_2$ receptor from a selected warm-blooded animal, then it may be beneficial to amplify the relevant sequence such that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402,1989; Lomeli et al., *Clinical Chem.* 35(9):1826–1831, 1989; U.S. Pat. No. 4,786,600), and nucleic acid amplification utilizing Polymerase Chain Reaction ("PCR") (see U.S. Pat. Nos. 4,683,195, 4,683,202, and 4,800,159) (see also, U.S. Pat. No. 4,876,187, and 5,011,769, which describe an alternative detection/amplification system comprising the use of scissile linkages).

Within a particularly preferred embodiment, PCR amplification is utilized to detect or obtain a $CRF_2$ receptor nucleic acid. Briefly, as described in greater detail below, a nucleic acid sample is denatured at 95° C. in order to generate single stranded nucleic acid. Specific primers, as discussed below, are then annealed at 37° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence.

Primers for the amplification of a selected sequence should be selected from sequences which are highly specific and form stable duplexes with the target sequence. The primers should also be non-complementary, especially at the 3' end, should not form dimers with themselves or other primers, and should not form secondary structures or duplexes with other regions of nucleic acid. In general, primers of about 18 to 20 nucleotides are preferred, and may be easily synthesized using techniques well known in the art.

Therapeutic Uses of $CRF_2$ Receptor(s) and $CRF_2$ Receptor Antagonists $CRF_2$ receptors (or portions thereof), $CRF_2$ receptor agonists and antagonists, as well as the nucleic acid sequences which encode these molecules may be utilized in a variety of therapeutic applications. For example, within one embodiment of the invention $CRF_2$ receptors (or portions thereof which bind a substrate such as CRF, sauvagine, or urotensin I) may be utilized in order to reduce vascular levels of the substrate or high ACTH levels due to an excess of the substrate. Thus, $CRF_2$ receptors may be utilized in treating diseases which are associated with high cortisol levels, including for example Cushing's Disease, alcoholism, anorexia nervosa, and other related disorders.

Similarly, $CRF_2$ receptors, (or portions thereof which bind a substrate as discussed above) may be utilized in treating tumors which produce high levels of a substrate (e.g., CRF) such as pituitary tumors, as well as for treating abnormalities during pregnancy such as preclampsia which are associated with increased CRF levels. Similarly, they may be utilized to treat hypotension, to modulate the effect of immune system disorders such as arthritis, and to modulate the effect of pituitary disorders. In addition, $CRF_2$ receptors, (or portions thereof) may be utilized in order to modulate a variety of brain functions, including for example control of satiety, reproduction growth, anxiety, depression, fever, metabolism.

Within yet another aspect of the present invention, viral vectors are provided which may be utilized to treat diseases wherein either the $CRF_2$ receptor (or a mutant $CRF_2$ receptor) is over-expressed, or where no $CRF_2$ receptor is expressed. Briefly, within one embodiment of the invention, viral vectors are provided which direct the production of antisense $CRF_2$ receptor RNA, in order to prohibit the over-expression of $CRF_2$ receptors, or the expression of mutant $CRF_2$ receptors. Within another embodiment, viral vectors are provided which direct the expression of $CRF_2$ receptor cDNA. Viral vectors suitable for use in the present invention include, among others, herpes viral vectors (e.g., U.S. Pat. No. 5,288,641), retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218; Vile and Hart, *Cancer Res.* 53:3860–3864,1993; Vile and Hart, *Cancer Res.* 53:962–967,1993; Ram et al., *Cancer Res.* 53:83–88, 1993; Takamiya et al., *J. Neurosci. Res* 33:493–503, 1992; Baba et al., *J. Neurosurg* 79:729–735,1993), pseudotyped viruses, adenoviral vectors (e.g., WO 94/26914, WO 93/9191; Kolls et al., *PNAS* 91(1):215–219,1994; Kass-Eisler et al., *PNAS* 90(24):11498–502,1993; Guzman et al., *Circulation* 88(6): 2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409,1993; Caillaud et al., *Eur. J. Neurosci.* 5(10):1287–1291,1993; Vincent et al., *Nat. Genet.* 5(2):130–134, 1993; Jaffe et al., *Nat. Genet.* 1(5):372–378, 1992; and Levrero et al, *Gene* 101(2):195–202, 1991), adenovirus-associated viral vectors (Flotte et al., *PNAS* 90(22):10613–10617, 1993), parvovirus vectors (Koering et al., *Hum. Gene Therap.* 5:457–463, 1994), baculovirus vectors, and pox virus vectors (Panicali and Paoletti, *PNAS* 79:4927–4931, 1982; and Ozaki et al., *Biochem. Biophys. Res. Comm.* 193(2):653–660,1993). Within various embodiments, either the viral vector itself, or a viral particle which contains the viral vector may be utilized in the methods and compositions described below.

Within other embodiments of the invention, the vectors which contain or express nucleic acid molecules of the present invention, or even the nucleic acid molecules themselves, may be administered by a variety of alternative techniques, including for example direct nucleic acid injection (Acsadi et al., *Nature* 352:815–818, 1991); liposomes (Pickering et al., *Circ.* 89(1):13–21, 1994; and Wang et al., *PNAS* 84:7851–7855,1987); lipofection (Felgner et al., *Proc. Natl. Acad. Sci. USA* 84:7413–7417,1989); microprojectile bombardment (Williams et al., *PNAS* 88:2726–2730, 1991); nucleic acid ligand (Wu et al., *J. of Biol. Chem.* 264:16985–16987,1989); administration of nucleic acid linked to killed adenovirus (Michael et al., *J. Biol. Chem.* 268(10):6866–6869, 1993; and Curiel et al., *Hum. Gene Ther.* 3(2):147–154, 1992), retrotransposons, cytofectin-mediated introduction (DMRIE-DOPE, Vical, Calif.) and transferrin-nucleic acid complexes (Zenke).

Improving Learning and Memory

As noted above, the present invention also provides methods for improving learning and memory by administration to a patient of a therapeutically effective amount of a $CRF_2$ receptor antagonist. Briefly, such patients may be identified through a clinical diagnosis based on symptoms of dementia or learning and memory loss. For example, individuals with an amnestic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning.

Dementia is characterized by multiple clinically significant deficits in cognition that represent a significant change from a previous level of functioning. Memory impairment involving inability to learn new material or forgetting of previously learned material is required to make the diagnosis of a dementia. Memory can be formally tested by asking the person to register, retain, recall and recognize information. The diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

A standard test used by clinicians to determine if a patient has impaired learning and memory is the Minimental Test for Learning and Memory (Folstein et al., *J. Psychiatric Res.* 12:185, 1975). This test involves a number of simple tasks and written questions. For instance, "paired-associate" learning ability is impaired in amnesiac patients of several types including those suffering from head trauma, Korsakoff's disease or stroke (Squire, 1987). Ten pairs of unrelated words (e.g., army-table) are read to the subject. Subjects are then asked to recall the second word when given the first word of each pair. The measure of memory impairment is a reduced number of paired-associate words recalled relative to a matched control group. This serves as an index of short-term, working memory of the kind that deteriorates rapidly in the early stages of dementing or amnesiac disorders.

Improvement in learning and memory constitutes either (a) a statistically significant difference between the performance of $CRF_2$ receptor antagonist treated patients as compared to members of a placebo group; or (b) a statistically significant change in performance in the direction of normality on measures pertinent to the disease model. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task (Davidson and Stern, 1991). Another potential application for therapeutic interventions against memory impairment is suggested by age-related deficits in performance which are effectively modeled by the longitudinal study of recent memory in aging mice (Forster and Lal, 1992).

In animals, several established models of learning and memory are available to examine the beneficial cognitive enhancing effects and potential anxiety-related side effects of activation of CRF-sensitive neurons. For example, both the Morris maze (Stewart and Morris, in *Behavioral Neuroscience*, R. Saghal, Ed. (IRL Press, 1993) p.107) and the Y-maze (Brits et al., *Brain Res. Bull.* 6, 71 (1981)) tests measure cognitive enhancing effects. Anxiety-related effects may be evaluated in the elevated plus-maze. (Pellow et al., *J. Neurosci. Meth.* 14:149,1985.)

Briefly, the Morris water maze is one of the best validated models of learning and memory, and it is sensitive to the cognitive enhancing effects of a variety of pharmacological agents (McNamara and Skelton, *Brain Res. Rev.* 18:33, 1993). The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia (McNamara and Skelton, 1993; Davidson and Stern, 1991; McEntee and Crook, 1992; Dawson et al., 1992). In addition, this animal paradigm accurately models the increasing degree of impairment with advancing age (Levy et al., 1994) and the increased vulnerability of the memory trace to pre-test delay or interference (Stewart and Morris, 1993) which is characteristic of amnesiac patients.

The test is a simple spatial learning task in which the animal is placed in tepid water, which is opaque due to the addition of powdered milk. The animals learn the location of the platform relative to visual cues located within the maze and the testing room; this learning is referred to as place learning. Briefly, 15 minutes prior to training on each of days 1–3, groups of animals receive ICV injections of control solution or 0.1, 1, 5, or 25 µg of a $CRF_2$ receptor antagonist. Control animals typically reach the platform within five to ten seconds after three days of training. The measure of the memory modulator effects of a $CRF_2$ receptor antagonist is a shift of this time period.

The Y-maze test based on visual discrimination is another assay of learning and memory in animals. In this maze, two arms of the maze end in a translucent plastic panel behind which there is a 40-watt electric bulb. The start box is separated from the third arm by a manually-activated guillotine door. In the first trial, all animals are allowed to explore the maze for five minutes, and food pellets are available in each arm. On the second day, each animal is placed in the start box with the door closed. When the door is opened, the animal is allowed to move down the arms and eat the pellets which are located in both arms. On the third day, animals receive six trials in groups of three where one arm is closed at the choice point, no discriminative stimulus is present, and two food pellets are available in the open goal box. On days 4–10, a light at the end of the arm with the food pellets is illuminated and ten trials are run, again in groups of three. The time it takes for the animal to reach the food pellets is recorded.

The effectiveness of a $CRF_2$ receptor antagonist to improve learning and memory in the Y-maze is tested as follows. Fifteen minutes prior to each of the blocks of training trials on days 4–10, groups of animals receive ICV injections of control solutions or doses of 1, 5, or 25 µg of a $CRF_2$ receptor antagonist. Control animals are expected to make 50% correct choices. The measure of efficacy of treatment on memory is an increase in correct responses.

The elevated plus maze test measures anxiogenic responses in an approach-avoidance situation involving an exposed, lighted space versus a dark, enclosed space. Both spaces are elevated and are set up as two runways intersecting in the form of a plus sign. This type of approach-avoidance situation is a classical test of "emotionality" and is very sensitive to treatments that produce disinhibition and stress. Briefly, animals are placed in the center of the maze and are allowed free access to all four arms in a five minute testing period. The time spent in each arm is recorded.

In humans, determination of improving learning and memory may be measured by such tests as the Wechsler Memory Scale or a pair-associate memory task. The Wechsler Memory Scale is a widely-used pencil-and-paper test of cognitive function and memory capacity. In the normal population, the standardized test yields a mean of 100 and a standard deviation of 15, so that a mild amnesia can be detected with a 10–15 point reduction in the score, a more severe amnesia with a 20–30 point reduction, and so forth (Squire, 1987). During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/mlmory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory is present within the context of the present invention if there is a statistically significant difference in the direction of normality in the paired-associate test, for example, between the performance of $CRF_2$ receptor antagonist treated patients as compared to members of the placebo group or between subsequent tests given to the same patient.

Alzheimer's Disease

The present invention provides methods for treating Alzheimer's disease (AD) by administration to a patient of a therapeutically effective amount of a $CRF_2$ receptor antagonist. Briefly, such patients may be identified through clinical diagnosis based on symptoms of dementia or learning and memory loss which are not attributable to other causes. In addition, patients are also identified through diagnosis of brain atrophy as determined by magnetic resonance imaging.

Several established animal models of Alzheimer's disease which focus on cholinergic deficits are available. The primary role of cholinergic deficits in AD is well established. In AD, there are significant positive correlations between reduced choline acetyltransferase activity and reduced CRF levels in the frontal, occipital, and temporal lobes (DeSouza et al., 1986). Similarly, there are negative correlations between decreased choline acetyltransferase activity and an increased number of CRF receptors in these three cortices (Id.). In two other neurodegenerative diseases, there are highly significant correlations between CRF and choline acetyltransferase activity in Parkinson's disease, but only a slight correlation in progressive supranuclear palsy (Whitehouse et al., 1987).

In rats, anatomic and behavioral studies evidence interactions between CRF and cholinergic systems. First, in some brain stem nuclei, CRF and acetylcholinesterase are co-localized, and some cholinergic neurons also contain CRF. Second, CRF inhibits carbachol-induced behaviors (carbachol is a muscarinic cholinergic receptor antagonist), suggesting that CRF has effects on cholinergic systems (Crawley et al., *Peptides* 6:891,1985). Treatment with another muscarinic cholinergic receptor antagonist, atropine, results in an increase in CRF receptors (DeSouza and Battaglia, *Brain Res.* 397:401, 1986). Taken together, these data show that CRF and cholinergic systems interact similarly in humans and animals.

An animal model of Alzheimer's disease which focuses on cholinergic deficits is produced by the administration of scopolamine, a non-selective postsynaptic muscarinic receptor antagonist that blocks the stimulation of postsynaptic receptors by acetylcholine. In these animals, memory deficits are readily apparent as measured by passive avoidance or delayed-matching-to-position tests, which distinguish motor or perceptual deficits from amnesia or cognitive enhancing effects of experimental treatments. Thus, the Morris maze and Y-maze tests following scopolamine-induced amnesia are utilized to test memory impairment and subsequent enhancement following administration of a $CRF_2$ receptor antagonist. In the Morris maze, the design of the experiment is essentially as described above, but is modified to include treatment 30 minutes prior to training on each of days 1 to 3 with an ip injection of scopolamine hydrobromide (0.3 mg/kg). This amnestic dose of scopolamine impairs acquisition and retention of spatial and avoidance learning paradigms in the rat. The anti-amnestic effects of 1, 5, or 25 µg of a $CRF_2$ receptor antagonist are measured relative to the concurrent control groups who receive or do not receive scopolamine. The effect of the $CRF_2$ receptor antagonists on reversal of scopolamine-induced amnesia using the Y-maze is performed similarly to the Y-maze test described above. Modification of this test includes treatment 30 minutes prior to training on days 5 to 10 with an ip injection of scopolamine hydrobromide (0.3 mg/kg). The anti-amnestic effects of 1, 5, or 25 µg of a $CRF_2$ receptor antagonist administered ICV, centrally or systemically, are measured relative to concurrent control and scopolamine treated-control groups.

Several tests measuring cognitive behavior in AD have also been designed. (See Gershon et al., *Clinical Evaluation of Psychotropic Drugs: Principles and Guidelines*, Prien and Robinson (eds.), Raven Press, Ltd., New York, 1994, p. 467.) One of these tests, BCRS, measures concentration, recent memory, past memory, orientation, and functioning and self-care. The BCRS is designed to measure only cognitive functions. This test, as well as the Weschler Memory Scale and the Alzheimer's Disease-Associated Scale, may be used to determine improvement following therapeutic treatment with a $CRF_2$ receptor antagonist. As noted above, "improvement" in Alzheimer's disease is present within the context of the present invention if there is a statistically significant difference in the direction of normality in the Weschler Memory Scale test, for example, between the performance of $CRF_2$ receptor antagonist treated patients as compared to members of the placebo group or between subsequent tests given to the same patient. In addition, scopolamine-induced amnesia in humans can be used as a model system to test the efficacy of the $CRF_2$ receptor antagonists.

Cerebrovascular Disease

As noted above, the present invention also provides methods for treating cerebrovascular diseases such as stroke, reperfusion injury and migraines, by administration to a patient of a therapeutically effective amount of a $CRF_2$ receptor antagonist. A patient is deemed to have been treated if the administration of the $CRF_2$ receptor antagonist, results in a statistically significant benefit, as compared to controls, of a clinical or diagnostic indication of a cerebrovascular disease (see, e.g., Harrison's Principles of Internal Medicine, McGraw-Hill Book Co.). Representative examples of animal model systems to test the effects of a $CRF_2$ receptor antagonist upon cerebrovascular disease include focal ischemic damage from injusions of NMDA agonists (1-amino cyclobutane-cis-1,3 dicarboxulic acid). Such excitotoxic compounds may be fused into specific areas of the brain, and the toxicity measured by later staining with a compound such as tetrazolium. Indicia of neural protection may be evidenced by the reduction of the volume of infarction in animals treated with a $CRF_2$ receptor antagonist.

Administration of $CRF_2$ receptor antagonists may be by a variety of routes, including for example by direct injection into a site of injury or disease, via other intracranial, intradermal, intraperitoneal, intrathecal, subcutaneous, or intramuscular routes, or more preferably, orally or intravenously.

The following examples are offered by way of illustration, and not by way of limitation.

EXAMPLES

Example 1

Isolation of $CRF_2$ Receptor cDNA

A. Isolation of $CRF_2$ Receptor cDNA from a Rat Brain cDNA Library

Male Sprague-Dawley rats (Madison, Wis.) weighing between 175–250 gm are decapitated, and the brain excised. Total RNA is then isolated from the brain utilizing a Promega RNAgents Total RNA Kit (catalog #Z5110, Promega, Wisc.) according to the manufacturers instructions, followed by the isolation of poly A+ RNA utilizing a Promega PolyATract kit (catalog # Z5420). A cDNA phage library is then prepared utilizing a Giga-Pack Gold library construction kit according to the manufacturers instructions (catalog #237611, Stratagene, LaJolla, Calif.), which is in turn plated and screened essentially as described by Sambrook et al., (Molecular Cloning) with oligonucleotide 5'-CCCGGATGCC TACAGAGAAT GCCTGGAGGA TGGGACCTGG GCCTCAAGGG-3" (Sequence I.D. No. 5). This oligonucleotide is complementary to nucleotides 440–490 of the rat CRF2 receptor cDNA sequence shown in FIG. 1.

The phage library is rescreened until a single pure phage isolate is obtained. The phage is then grown on bacterial host XL1-Blue (Stratagene, LaJolla, Calif.), and plasmid nucleic acid is excised with ExAssist helper phage (Stratagene) in SOLR cells. The SOLR cells are then plated, and plasmid nucleic acid is isolated and sequenced utilizing the Sanger dideoxy protocol.

A rat CRF2 receptor cDNA sequence that may be obtained utilizing this procedure is set forth below in FIG. 2 and in Sequence I.D. No. 1.

B. Isolation of CRF$_2$ Receptor cDNA from a Rat Hypothalamus cDNA Library

CRF2 receptor cDNA can also be isolated from commercially available rat hypothalamus cDNA libraries. Briefly, two million plaques from a rat hypothalamus phage library (Stratagene, catalog # 936518) are plated according to the manufacturers instructions, and screened with oligonucleotide Sequence I.D. No. 5 essentially as described above.

A rat CRF2 receptor cDNA sequence that may be obtained utilizing this procedure is set forth below in FIG. 1 and in Sequence I.D. No. 3.

C. Isolation of CRF$_2$ Receptor cDNA from a Human cDNA Library

CRF2 receptor cDNA can also be isolated from commercially available human cDNA libraries. Briefly, approximately two million plaques from a human frontal cortex phage library (Stratagene, catalog # 936212) are plated according to the manufacturers instructions, and screened with oligonucleotide 5'-GATCAACTAC TCACAGTGTG AGCCCATTTT GGATGACAAG CAGAGGAAGT A-3' (Sequence I.D. No. 6) essentially as described above.

One human CRF2 receptor cDNA sequence that may be obtained utilizing this procedure is set forth below in Sequence I.D. No. 7. Briefly, the human sequence is 89.1% identical at the nucleotide level and 93.0% identical at the amino acid level to that of the above-described rat CRF2αreceptor (Sequence I.D. No. 3).

Example 2

Expression of CRF$_2$ Receptor cDNA pCDM7-Amp is first constructed from pCDM8 (Seed, *Nature* 329:840–842, 1987; Seed and Aruffo, Proc. Natl. Acad. Sci. 84:3365–3369, 1987; Thomsen et al., *Cell* 63:485–493, 1990; Bernot and Auffray, *Proc. Natl. Acad. Sci.* 88:2550–2554,1991; Han et al., *Nature* 349:697–700, 1991) by deletion of the adeno origin of replication, M13 origin of replication and sup F selection marker. An ampicillin resistance marker is added in order to facilitate selection of the plasmid.

A full-length CRF2 receptor clone in pBluescriptSK- is isolated from the phage clone described above, and cut with EcoRV and XhoI, releasing the insert. The insert is then isolated and ligated to pCDM7-Amp which had been similarly cut. The resulting product is used to transform *E. coli* DH5α, from which larger quantities of plasmid nucleic acid may be isolated.

COS-7 (ATCC No. CRL 1651) cells are then transfected with pCDM7-Amp containing CRF$_2$ receptor cDNA (10 ug nucleic acid/10 cm plate of cells) utilizing 400 μg/ml of DEAE-Dextran and 100 μM chloroquine. The cells are transfected for 4 hours, then shocked with 10% DMSO for 2 minutes. The cells are then washed, and grown in DMEM containing 10% Fetal Bovine Serum for 2 days in a 24-well plate.

Example 3

CRF$_2$ Receptor Binding Assay

Materials $^{125}$I-Tyr$^0$-ovine CRF ($^{125}$I-oCRF; specific activity, 2200 Ci/mmol) is obtained from Du Pont-New England Nuclear (Boston, Mass.). Unlabeled rat/human CRF is purchased from Peninsula Laboratories (Belmont, Calif.). All other standard reagents were purchased from Sigma Chemical Co. (St. Louis, Mo.).

A. Cell Membrane Preparation

Transfect cells which express CRF2 receptors are harvested, washed once in PBS (pH 7.0 at 22° C.), pelleted by centrifugation and stored at −70° C. until use. On the day of assay, frozen pellets are resuspended in 5 ml of ice cold buffer containing 50 mM Tris, 10 mM MgCl$_2$, 2 mM EGTA pH 7.0 at 22° C. and homogenized using a Polytron (PT3000, Brinkmann Instruments, Westbury, NY) at 27,000 rpm for 20 s. The homogenate is centrifuged at 48,000×g for 10 min at 4° C., the supernatant discarded, and the pellet was re-homogenized in the same volume of buffer and centrifuged again at 48,000×g for 10 min at 4° C. The resulting pellet containing membranes is resuspended in the above buffer to yield a final protein concentration of 300 mg/ml for use in the assay described below. Protein determinations were performed according to the method of Lowry et al. (*J. Biol. Chem.* 193:265–275, 1951) using bovine serum albumin (BSA) as a standard.

B. CRF Receptor Binding Assay

One hundred microliters of the membrane suspension is added to 1.5 ml (polypropylene microfuge tubes) containing 100 μl of (100–200 pM) $^{125}$I-oCRF in incubation buffer (50 mM Tris, 10 mM MgCl$_2$, 2 mM EGTA, 1.5% BSA, 0.15 mM bacitracin and 1.5% aprotinin) and 100 μl of the incubation buffer. Competing peptides (e.g., r/hCRF, sauvagine, urotensin I, urotensin II, bovine CRF (b-CRF), and deamidated bovine CRF (b-CRF—OH)) are also added. Incubations are carried out at room temperature (22° C.) for 2 hours, and terminated by centrifugation in a microfuge for 5 min at 12,000×g. The resulting pellet is washed gently with 1.0 ml of ice-cold phosphate-buffered saline, pH 7.2 containing 0.01% Triton X-100 and re-centrifuged for 5 min at 12,000×g. The microfuge tubes are cut just above the pellet, placed into 12×75 mm polystyrene tubes, and monitored for radioactivity in a Packard Cobra II gamma counter at approximately 80% efficiency. The non-specific binding of $^{125}$I-oCRF to membrane homogenates, is defined in the presence of 1 mM unlabeled CRF.

C. Saturation Curve Analysis

For saturation studies, 100 μl $^{125}$I-oCRF (50 pM -10 nM final concentration), 100 μl of assay buffer (with or without 1 μM r/hCRF final concentration, to define the non-specific binding) and 100 μl of membrane suspension (as described above) are added in sequence to 1.5 ml polypropylene microfuge tubes. All reactions are carried out for 2 h at 22° C. and terminated by centrifugation for 5 min at 12,000×g. Aliquots of the supernatant are collected to determine the amount of unbound radioligand. The remaining supernatant is aspirated. Pellets are washed gently with ice-cold PBS plus 0.01% Triton X-100, centrifuged again, and monitored for bound radioactivity. Data from saturation curves are analyzed using the non-linear least-squares curve-fitting program LIGAND (Munson and Rodbard, *Anal. Biochem* 107:220–229, 1980). Non-specific binding is not defined arbitrarily by the investigator, but rather is estimated as an independent variable from the entire data set.

D. Competition Curve Analysis

For competition studies, 100 μl $^{125}$I-oCRF (final concentration 200–300 pM) is incubated along with 100 μl buffer (in the presence of 1 pM to 10 mM of competing ligands) and 100 μl of membrane suspension as prepared above. The reaction is allowed to proceed for 2 h at 22° C. and was terminated by centrifugation as described above. Data from competition curves were also analyzed by the program LIGAND. For each competition curve, estimates of the affinity of the radiolabeled ligand for the CRF receptor ($^{125}$I-oCRF or $^{125}$I-r/hCRF) are obtained in independent saturation experiments. These estimates are constrained during the analysis of the apparent inhibitory constants ($K_i$) for the various related and unrelated peptides tested. Routinely, the data are analyzed using a one and two-site model comparing the "goodness of fit" between the models in order to accurately determine the $K_i$. Statistical analyses provided by LIGAND allowed the determination of whether a single-site or multiple-site model should be used. For CRF-related peptides, all data fit a single site model suggesting that the transfected cells contained a single homogeneous population of binding sites with high affinity and the appropriate pharmacological profile of the CRF receptor.

Example 4 cAMP Assay

The effect of CRF and related peptides on adenylate cyclase activity in transfected cells may be determined essentially as follows. For agonist testing, compounds are added to wells with buffer only in order to identify compounds with intrinsic activity. For antagonist testing, compounds are placed in the wells along with 1–100 nM CRF to stimulate the adenylate cyclase system. Compounds are then assessed for their ability to inhibit the CRF-stimulated cAMP production in the transfected cells. Briefly, cells are plated and grown in DMEM containing 10% fetal bovine serum for 2–4 days in 24-well plates at 37° C. On the day of assay, the medium is removed by vacuum aspiration and 100 μl of DMEM, 10 mM MgCl$_2$, 1 mM isobutylmethylxanthine (a phosphodiesterase inhibitor to inhibit the breakdown of cAMP produced) and 0.1% BSA (pH 7.2) are added to each well. CRF, related peptides and organic test molecules are added to individual wells. The plates are incubated at 37° C. for a period of 1 hour. Following incubation, the wells are aspirated, rinsed once with PBS and aspirated again. 300 μl of 95% Ethanol and 20 mM HCl (EtOH/HCl) are then added to each well and the plates incubated at -20° C. overnight to extract the produced cAMP. The EtOH/HCl is removed, placed in 1.5 ml polypropylene eppendorf tubes and the wells washed with an additional 200 μl of EtOH/HCl and pooled with the initial sample. All samples are dried in a Speed-Vac (Savant Instruments, Farmingdale NY) and either stored at -20° C. until use or reconstituted with 500 μl of sodium acetate buffer pH 7.5 and assayed immediately for cAMP concentration using a radioimmunoassay kit from Biomedical Technologies Inc. (Stoughton Mass.) according to manufacturers instructions.

Figure 3:
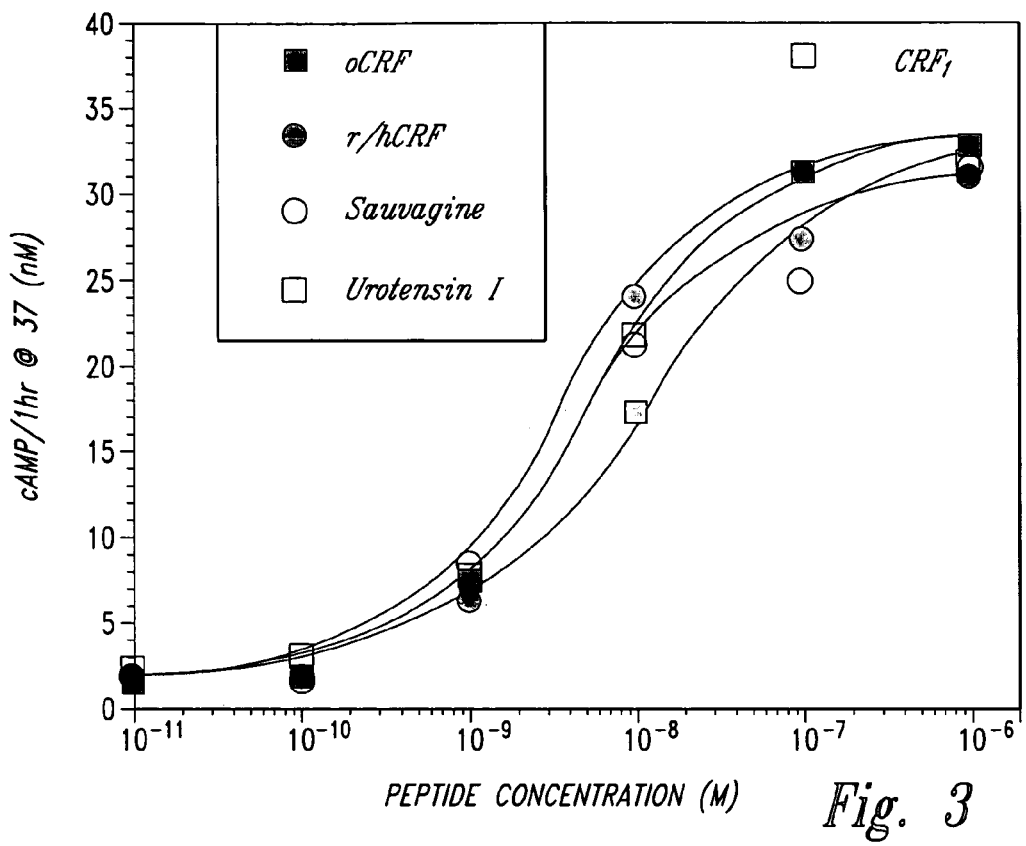
FIG. 3 is a graph which depicts cAMP accumulation in cells transfected with the $CRF_1$ receptor.
Figure 4:
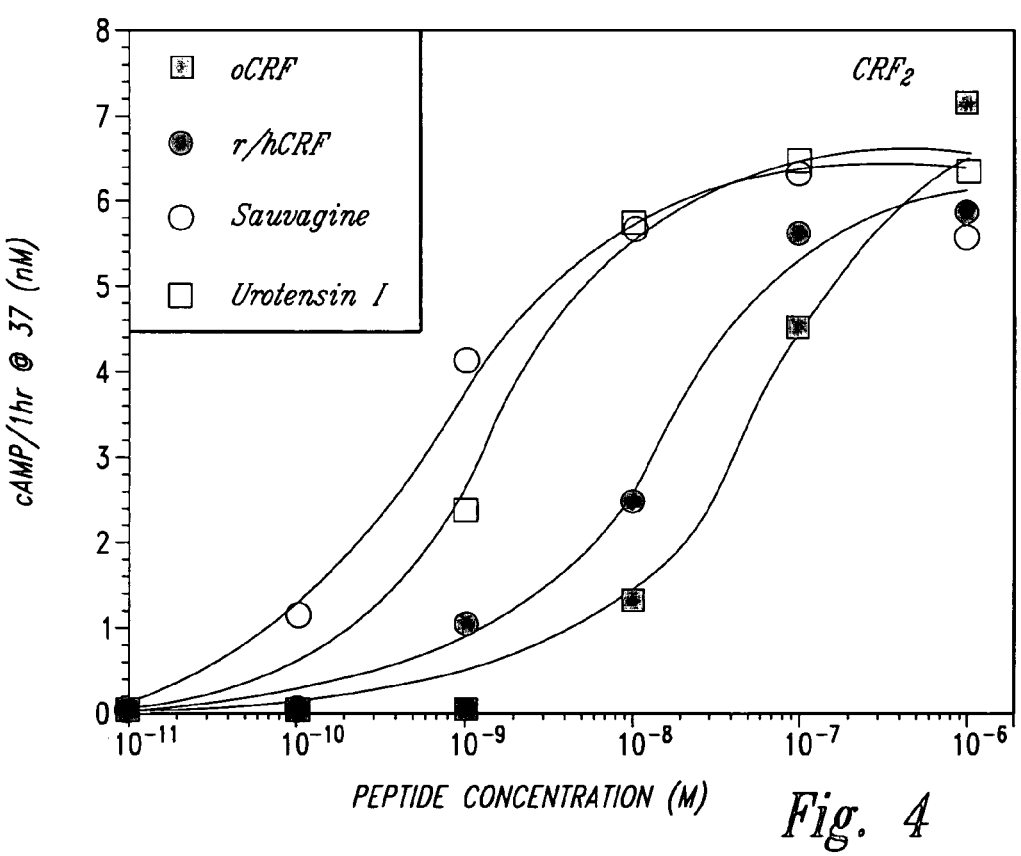
FIG. 4 is a graph which depicts cAMP accumulation in cells transfected with the $CRF_2$ receptor.

FIG. 3 represents cAMP accumulation in cells transfected with the CRF1 receptor and stimulated with ovine CRF (oCRF), rat/human CRF (r/hCRF), sauvagine or urotensin I. Briefly, this figure shows a dose-dependent increase in cAMP in response to these compounds. All of these compounds showed similar potencies. In FIG. 4, the rat CRF$_{2\alpha}$ receptor has been transfected into cells and cAMP accumulation is measured in response to the same drugs as shown in FIG. 3. As shown in FIG. 4, sauvagine and urotensin I are more potent than either OCRF or r/hCRF at stimulating cAMP. Together, these findings show a clearly distinct pharmacological profile between the CRF$_1$ and CRF$_2$ receptors.

Figure 5:
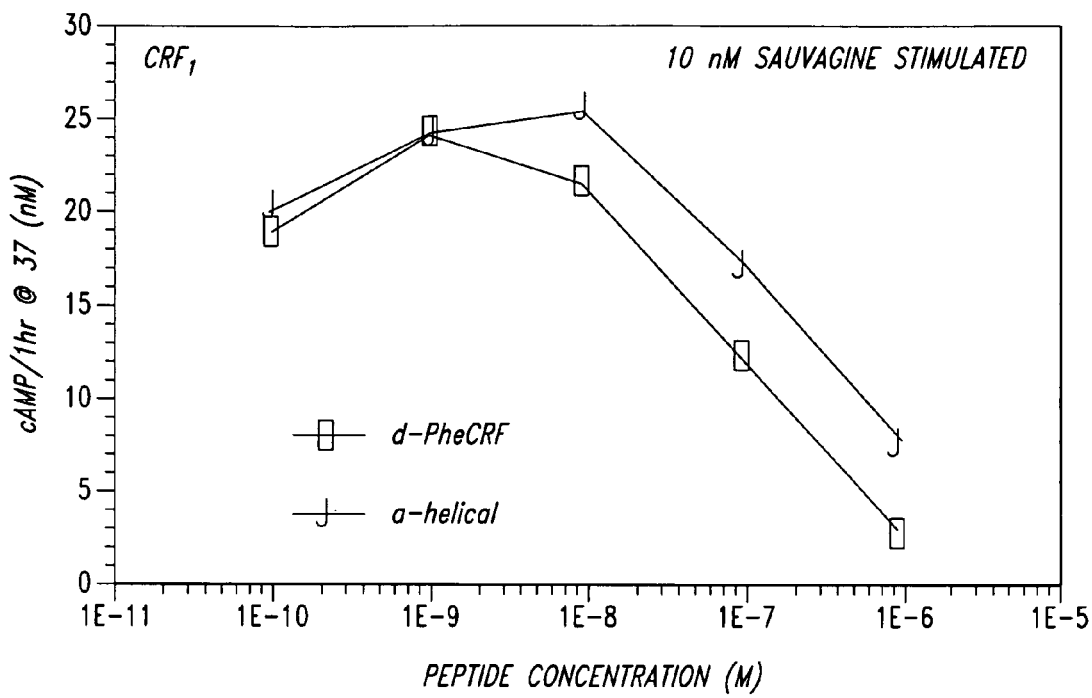
FIG. 5 is a graph which depicts the effect of the antagonists α-helical and d-Phe on Sauvagine stimulated cAMP production in $CRF_1$ transfected cells.
Figure 6:
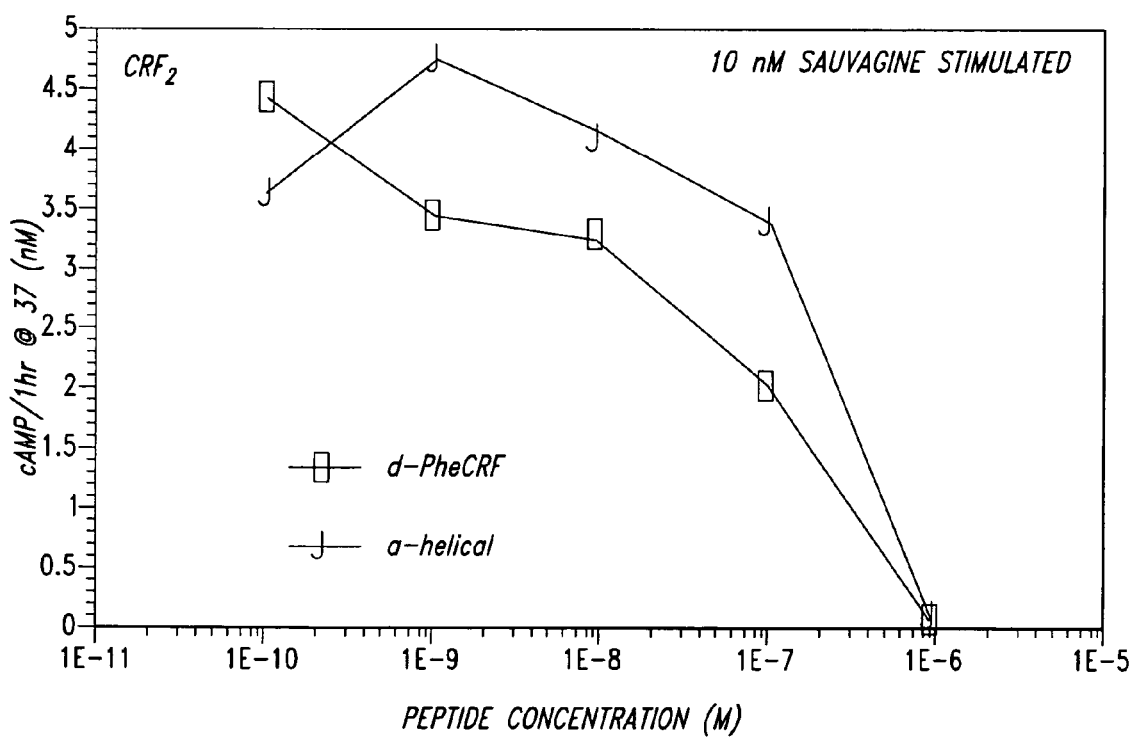
FIG. 6 is a graph which depicts the effect of the antagonists α-helical and d-Phe on Sauvagine stimulated cAMP production in $CRF_{2\alpha}$ transfected cells.

FIG. 5 and FIG. 6 depict the effect in CRF$_1$ and CRF$_{2\alpha}$ transfected cells, respectively, of the antagonists α-helical oRCF(9–41) and d-Phe r/hCRF(12–41) upon Sauvagine-stimulated cAMP production.

The above results have been formulated below in Table I, wherein the effective concentration of one-half maximal adenylate cyclase stimulation (EC$_{50}$) are presented.

TABLE I

| PEPTIDE | human CRF$_1$ receptor | human CRF$_{2\alpha}$ receptor | rat CRF$_{2\beta}$ receptor |
|---|---|---|---|
| oCRF | 10 nM | 80 nM | N/A |
| r/hCRF | 4 nM | 20 nM | 1 nM |
| Sauvagine | 3 nM | 0.5 nM | 0.4 nM |
| Urotensin I | 4 nM | 2 nM | N/A |
| bCRF | 30 nM | 100 nM | N/A |
| bCRF-OH | 1000 nM | >1000 | N/A |
| Gly41 r/hCRF-OH | 800 nM | >1000 | N/A |
| r/hCRF(6–33) | >1000 | >1000 | N/A |
| d-Phe r/hCRF(12–41) | >1000 | >1000 | N/A |
| α-helical oCRF(9–41) | >1000 | >1000 | N/A |
| VIP | >1000 | >1000 | N/A |
| AVP | >1000 | >1000 | N/A |
| hGRF | >1000 | >1000 | N/A |

Example 5

Tissue Distribution of CRF$_{2\alpha}$ and β Receptors

In order to determine anatomical distribution of the two CRF$_2$ receptor forms, mRNA expression patterns were analyzed in isolated RNA (RNase protection assays) and whole tissue sections (in situ hybridization) from rat brain and peripheral tissues essentially as described below.

A. RNase Protection Assay

A 366-base riboprobe, containing 258-base antisense sequence specific to rat the CRF$_{2\alpha}$ receptor, and a 278-base riboprobe containing 181-base antisense sequence specific to the CRF$_{2\beta}$ receptor mRNA were generated by T3 RNA polymerase in 40 mM Tris-HCl (pH 7.5), 6 mM MgCl, 2 mM spermidine, 10 mM NaCl, 10 mM DTT, 1 U/μl of RNasin (Promega), 0.5 mM each of ATP, CTP, TTP, and 3 μM of $^{32}$P-UTP (DuPont, 800 Ci/mmol), 0.1 μg/μl of template DNA, 1 U/μl of T3 RNA polymerase in total volume of 10 μl at 37° C. for 30 minutes. A 712-base riboprobe containing 632-base of antisense sequence specific to rat β-actin mRNA was generated in the same conditions, except using T7 RNA polymerase. The probe synthesis mixtures were then treated with DNase I at concentration of 1 U/μl at 37° C. for 10 minutes and then electrophoresed on a 5% denaturing acrylamide gel. The $^{32}$P-labeled RNA probes with expected sizes were recovered from the gel with an RNA purification kit, RNaid kit (Bio-101, La Jolla, Calif.). RNA hybridization, RNase digestion and separation of protected RNAs were performed as described by Sawbrook et al., supra. In assays for $CRF_2$ receptor mRNAs, 40 μg of total RNA was used in each sample. In assays for β-actin mRNA, 1 μg of total RNA was used for each sample.

B. In Situ Hybridization

Male Sprague-Dawley rats were sacrificed by decapitation, and the brains removed and frozen in liquid isopentane (−42° C.). Subsequently, tissues were sectioned (15 μm) on a cryostat maintained at −20° C. and thaw mounted onto polylysine-coated microscope slides. Sections were stored at −80° C. prior to tissue fixation.

Sections were removed from storage at −80° C. and placed directly into 4% buffered paraformaldehyde at room temperature. After 60 minutes, slides were rinsed in isotonic phosphate buffered saline (10 minutes) and treated with proteinase K (1 μg/ml) in 100 mM Tris/HCL, pH 8.0) for 10 minutes at 37° C. Subsequently, sections underwent successive washes in water (1 minute), 0.1 M triethanolamine (pH 8.0, plus 0.25% acetic anhydride) for 10 minutes and 2×SSC (0.3 mM NaCl, 0.03 mM sodium citrate, pH 7.2) for 5 minutes. Sections were then dehydrated through graded alcohols and air dried.

RNA probes (as described above) were synthesized using Maxiscript RNA transcription kits (Ambion, Austin, Tex.). Post-fixed sections were hybridized with 1.0×10$^6$ dpm of [$^{35}$S]UTP-labeled riboprobes in hybridization buffer containing 75% formamide, 10% dextran sulphate, 3×SSC, 50 mM sodium phosphate buffer (pH 7.4), 1× Denhardt's solution, 0.1 mg/ml yeast tRNA and 10 mM dithiothreitol in a total volume of 25 μl. The diluted probe was applied to sections on a glass coverslip which was sealed into place with rubber cement. Sections were hybridized overnight at 55° C. in a humid environment.

Post-hybridization the rubber cement was removed and sections were washed in 2×SSC for 5 minutes and then treated with RNase A (200 μg/ml in 10 mM Tris/HCL, pH 8.0, containing 0.5 M NaCl) for 60 minutes at 37° C. Subsequently, sections were washed in 2×SSC for 5 minutes, 1×SSC for 5 minutes, 0.5×SSC for 60 minutes at hybridization temperature, 0.5×SSC for 60 minutes at room temperature for 5 minutes and then dehydrated in graded alcohols and air dried. For signal detection, sections were placed on Kodak XAR-5 X-ray film and exposed for 7 days at room temperature.

C. Results

Figure 7:
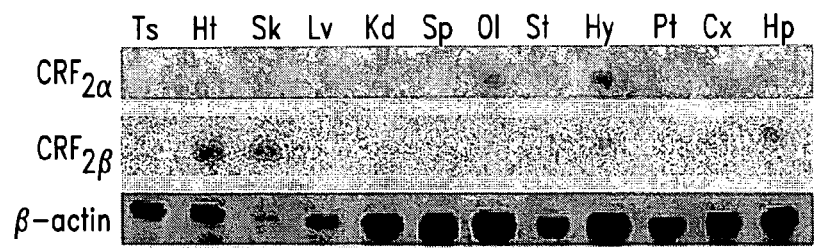
FIG. 7 is a photograph of an RNase protection assay of two $CRF_2$ subtypes ($CRF_{2\alpha}$, and $CRF_{2\beta}$), and β-actin. Ts=testis; Ht=heart; Sk=skeletal muscle; Lv=liver; Kd=kidney; Sp=spleen; Ol=olfacfory bulb; St=striatum; Hy=hypothalamus; Pt=pituitary; Cx=cortex; Hp=hippocampus.
Figure 8A:
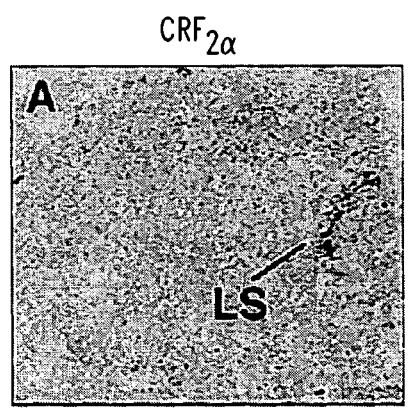
FIGS. 8A, A', B, B', C and C' are a series of photographs which show the anatomical distribution of two $CRF_2$ subtypes. 8A, B and C are coronal sections of rat brain probed with CRF2α and CRF2β.
Figure 8A:
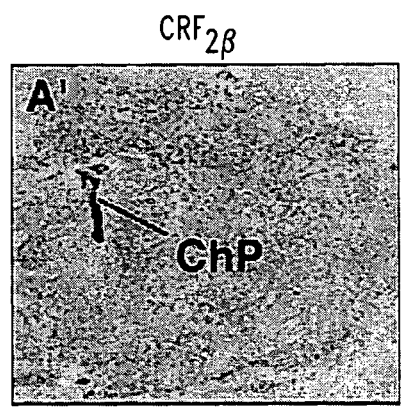
Figure 8B:
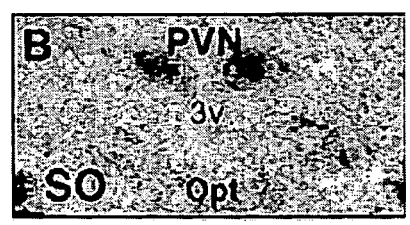
Figure 8B:
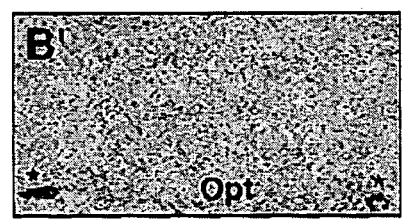
Figure 8C:
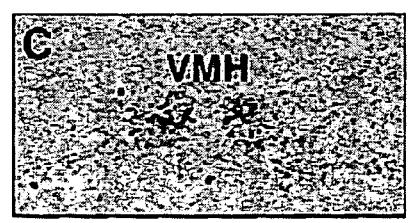
Figure 8C:
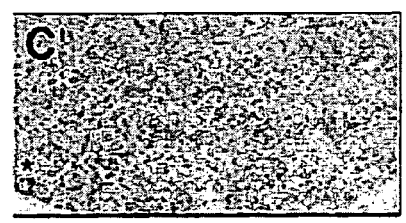

As shown in FIG. 7, based upon RNase protection assays $CRF_{2\alpha}$ and $CRF_{2\beta}$ receptor mRNAs have clearly distinct tissue distributions. In particular, $CRF_{2\alpha}$ is found primarily in the brain, particularly in the hypothalamus, lateral septum and olfactory bulb, whereas the $CRF_{2\beta}$ mRNA is found primarily, but not restricted to, the heart and skeletal muscle. This is in stark contrast to the previously disclosed distribution of the $CRF_1$ receptor (Potter et al., *PNAS* 91:8777–8781,1994).

Results of in situ hybridization assays are shown in FIG. 8. FIGS. 8A, B, C and 8A', B', C' show coronal sections of rat brain probed with antisense $CRF_{2\alpha}$ and $CRF_{2\beta}$ probes, respectively. There is clear expression of $CRF_{2\alpha}$ in the lateral septum (A), whereas $CRF_{2\beta}$ is expressed in choroid plexus (A'). FIGS. 8B and 8C show $CRF_{2\alpha}$ expression in the paraventricular nuclei and ventromedial hypothalamic nuclei, respectively. $CRF_{2\beta}$ is not detected in either of these areas (FIGS. 8B' and 8C'). $CRF_{2\alpha}$ is also detected in the supraoptic nuclei (FIG. 8B), whereas $CRF_{2\beta}$ is expressed in the adjacent arterioles (FIG. 8B'). $CRF_{2\alpha}$ was also found to be expressed on many of the arterioles in the brain which express $CRF_{2\beta}$ albeit at a lower level (not shown). In heart, $CRF_{2\beta}$ was the major form expressed, and was found predominantly on arterioles (not shown).

Example 6

Anatomical Distribution of $CRF_1$ and $CRF_2$ mRNA

A. Materials and Methods

1. Animals: Male Sprague Dawley rats (200–220 g) were used for mapping studies. Prior to sacrifice, animals were housed in a 12 hr light/dark cycle with food and water provided ad libitum.

Figure 9:
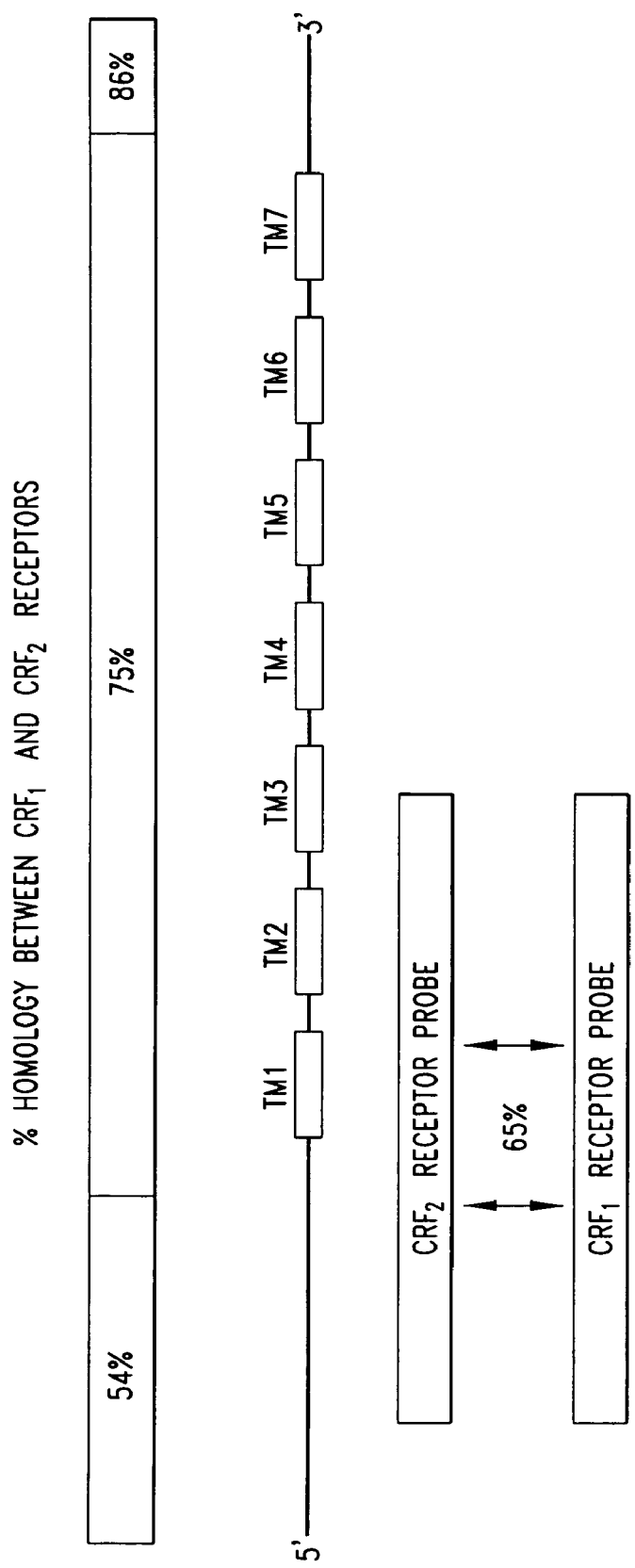
FIG. 9 is a schematic illustration of nucleotide sequence homology between $CRF_1$ and $CRF_2$ receptors across the coding region of the receptors. Lower bars indicate the region of the receptors against which $CRF_1$ and $CRF_2$ cRNA probes were designed.

2. Riboprobe Design: $CRF_2$ cRNA riboprobe was produced from a 460 bp cDNA fragment of the $CRF_2$ receptor sub-cloned into pBluescriptSK+(Stratagene, La Jolla) and linearized with Xba I. $CRF_1$ probe was synthesized from a 460 bp 5' fragment of $CRF_1$ cDNA in pBluescriptSK+, linearized with Xba I. Both $CRF_2$ and $CRF_1$ riboprobes were directed against the 5' region of their respective receptors, covering the sequence up to the third presumed transmembrane region (FIG. 9). The approximate nucleotide homology between the two probes is 65% in this region. Importantly, in preliminary experiments, cRNA probes directed against the 3' region of the $CRF_2$ receptor apparently labeled both $CRF_1$ and $CRF_2$ receptor mRNA's whereas the two mRNA species could be clearly separated by 5' specific probes under similar hybridization conditions. Thus, it seems necessary to utilize 5' probes for subtype-specific labeling. For both probes, specificity was confirmed by absence of signal in sections labeled with sense probe and sections pretreated with RNase prior to hybridization with antisense (CRNA) probe. CRF CRNA antisense probes were synthesized from a 770 bp fragment of CRF cDNA sub-cloned into a pGEM3Z vector (courtesy Dr. Robert Thompson, University of Michigan). Riboprobes were produced using either T3 or T7 transcription systems in a standard labelling reaction mixture consisting of: 1 μg linearized plasmid, 5× transcription buffer, 125 μCi $^{35}$S-UTP or $^{33}$P-UTP, 150 μM NTP's, 12.5 mM dithiothreitol, 20U RNAse inhibitor and 6U of the appropriate polymerase. The reaction was incubated at 37° C. for 90 min, labeled probe being separated from free nucleotides over Sephadex G-50 spin columns.

3. In Situ Hybridization Histochemistry: Dissected tissue was frozen in isopentane cooled to −42° C. and subsequently stored at −80° C. prior to sectioning on a cryostat. Slide-mounted tissue sections were then stored at −80° C. Sections were removed from storage and placed directly into 4% buffered paraformaldehyde at room temperature. After 60 min, slides are rinsed in isotonic phosphate buffered saline (10 min) and treated with proteinase K (1 μg/ml in 100 mM Tris/HCl, pH 8.0) for 10 min at 37° C. Subsequently, sections underwent successive washes in water (1 min), 0.1 M triethanolamine (pH 8.0, plus 0.25% acetic anhydride) for 10 min and 2×SSC (0.3 mM NaCl, 0.03 mM sodium citrate, pH 7.2) for 5 min. Sections were then dehydrated through graded alcohols and air dried. Post-fixed sections were hybridized with $1.0 \times 10^6$ dpm [$^{35}$S]UTP-labelled riboprobes in hybridization buffer containing 75% formamide, 10% dextran sulphate, 3×SSC, 50 mM sodium phosphate buffer (pH 7.4), 1× Denhardt's solution, 0.1 mg/ml yeast tRNA and 10 mM dithiothreitol in a total volume of 30 μl. The diluted probe was applied to sections on a glass coverslip and hybridized overnight at 55° C. in a humid environment. Post-hybridization, sections were washed in 2×SSC for 5 min and then treated with RNase A (200 μg/ml in 10 mM Tris/HCl, pH 8.0, containing 0.5 M NaCl) for 60 min at 37° C. Subsequently, sections were washed in 2×SSC for 5 min, 1×SSC for 5 min, 0.1×SSC for 60 min at 70° C., 0.5×SSC at room temperature for 5 min and then dehydrated in graded alcohols and air dried. For signal detection, sections were placed on Kodak Bio Max X-ray film and exposed for the required length of time or dipped in photographic emulsion (Amersham LM-1) for high resolution analysis. Autoradiograms were analyzed using automated image analysis (DAGE camera/Mac II/IMAGE program). Briefly, anatomical regions of interest were interactively selected and mean optical density measurements determined from at least three coronal sections. Background signal was determined from an area of section in which labelling was undetectable. Dipped sections were examined using a Zeiss Axioscope.

B. Results

1. $CRF_2$ Probe Selection

As illustrated in FIG. 1, the $CRF_2$ cRNA probe utilized in the present studies was synthesized from a 460 bp 5' fragment of $CRF_2$ cDNA. Preliminary in situ hybridization studies using cRNA probes encompassing the 3' portion of the receptor (bearing high homology to the $CRF_1$ receptor) afforded an anatomical distribution which was inconsistent with that obtained using 5'-specific riboprobes. The pattern of labelling was, however, consistent with both $CRF_1$ and $CRF_2$ receptor mRNA distribution. The high sequence homology between $CRF_1$ and $CRF_2$ receptors thus necessitates the use of 5'-containing riboprobes for specific hybridization of $CRF_2$ or $CRF_1$ receptor subtype mRNA.

2. Anatomical Distribution

The comparative anatomical distribution of $CRF_2$ and $CRF_1$ mRNA was determined in adjacent coronal brain sections. Table II below summarizes the semi-quantitative analysis of the data.

Figure 10:
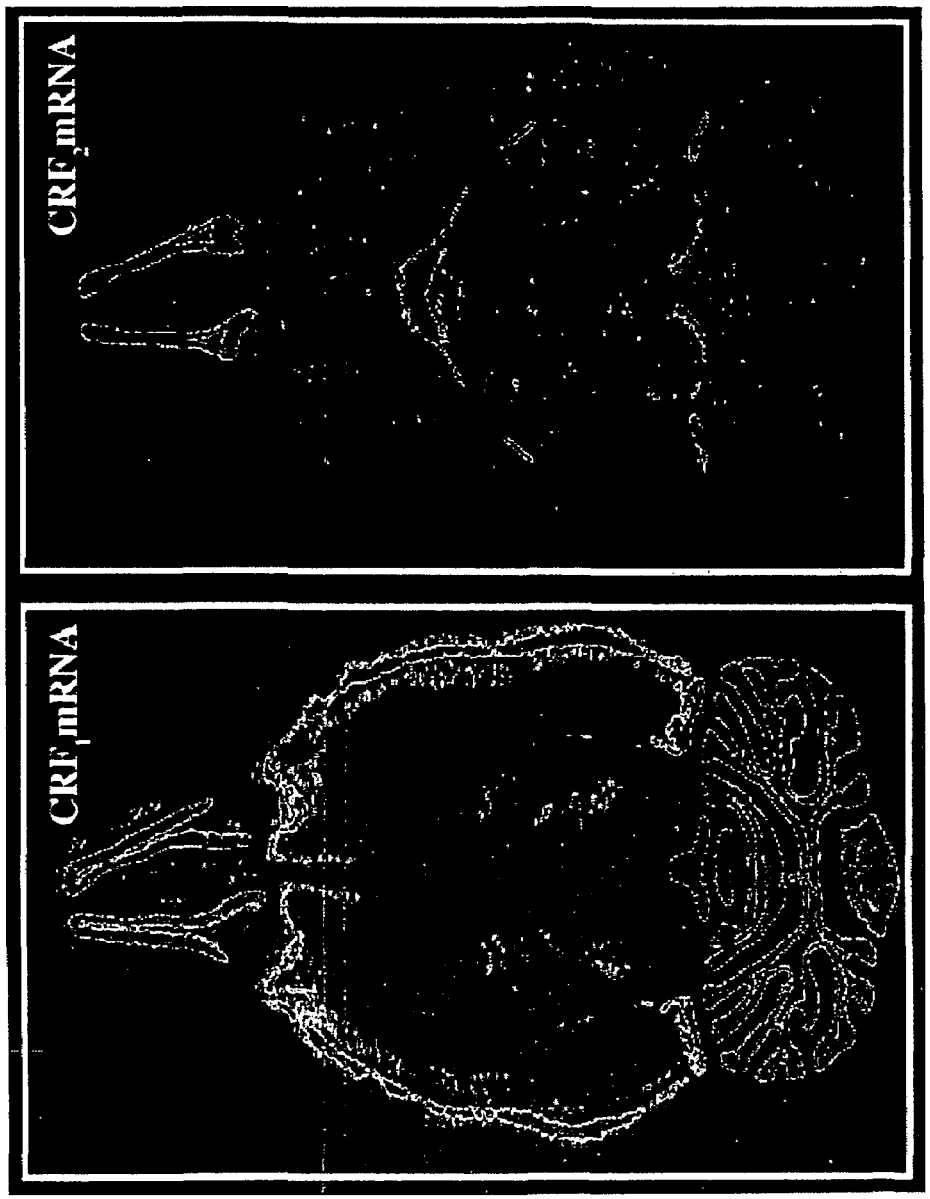
FIG. 10 is two color-coded digitized images of $CRF_1$ and $CRF_2$ receptor mRNA expression in adjacent horizontal brain sections. Regions exhibiting high levels of mRNA expression are coded in red and orange while the lowest levels of expression are coded in blue.
Figure 11A:
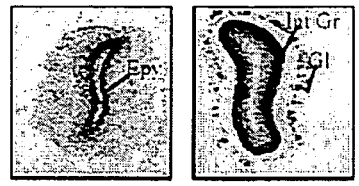
FIGS. 11A, B, C, D and E are a series of photographs which show the rostro-caudal (A-E) distribution of $CRF_2$ receptor mRNA (left hemisphere) and $CRF_1$ receptor mRNA (right hemisphere) in digitized coronal brain sections. Epy, ependymal layer of olfactory bulb; Int Gr, internal granule cell layer of olfactory bulb; G1, granule cell layer of olfactory bulb; LSI, lateral septal nucleus (intermediate part); LSV, lateral septal nucleus (ventral part); MS, medial septal nucleus; Fr Ctx, frontal cortex; Pir, piriform cortex; $CA_1$, field $CA_1$ (Ammons horn); $CA_3$, field $CA_3$ (Ammons horn); DG, dentate gyrus; Chp, choroid plexus; MeA, medial amygdaloid nucleus; VMH, ventromedial hypothalamic nucleus; Cing Ctx, cingulate cortex; BLA, basolateral amygdaloid nucleus; PCo, posterior cortical amygdaloid nucleus; RN, red nucleus; Oc Ctx, occipital cortex; MG, medial geniculate nucleus; PDTg, posterior dorsal tegmental nucleus; Trg Nuc, trigeminal nuclei; Pn, pontine gray.
Figure 11B:
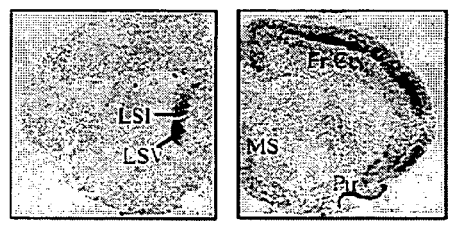
Figure 11C:
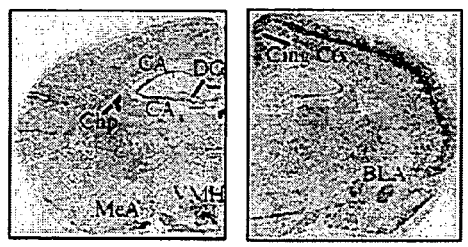
Figure 11D:
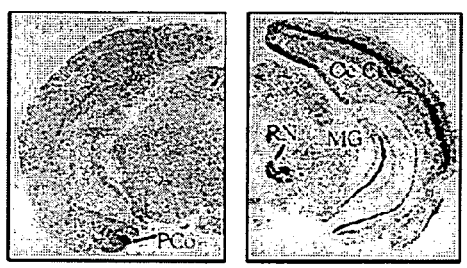
Figure 11E:
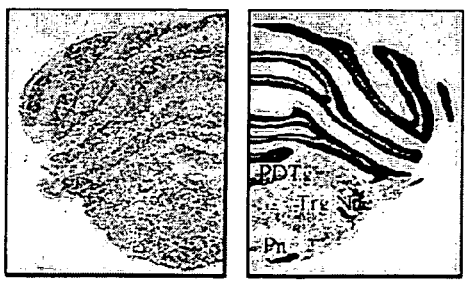
Figure 12A:
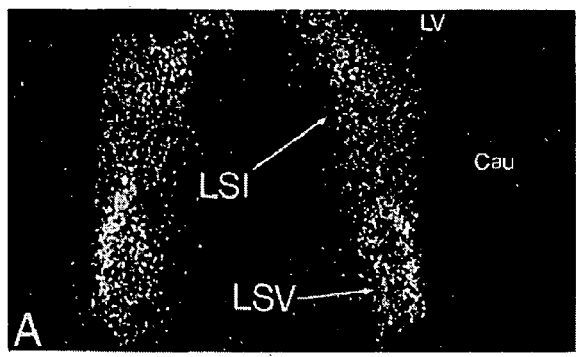
FIGS. 12A and B are two darkfield photomicrographs of cells hybridized with ($^{35}$S) cRNA $CRF_2$ probe in (A) the intermediate (LSI) and ventral (LSV) lateral septal nuclei. At high resolution (B) note the high level of $CRF_2$ receptor expression in cells in the ventral lateral septum. Cau, caudate; LV, lateral ventricle.
Figure 12B:
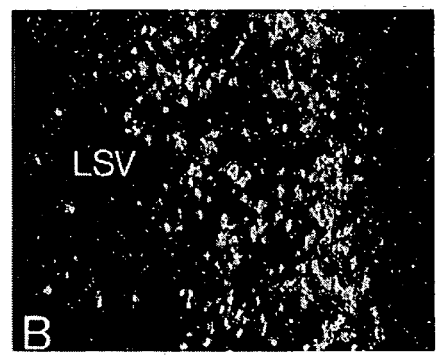

As illustrated in horizontal section (FIG. 10), the distribution of $CRF_2$ receptor mRNA clearly differs from that of $CRF_1$, exhibiting a distinct sub-cortical pattern. While $CRF_1$ mRNA expression was high in a range of telencephalic structures, $CRF_2$ receptor expression exhibited a more anatomically specific pattern including the lateral septal region (LS), the bed nucleus of the stria terminalis (BNST), the amygdaloid area and the olfactory bulb (FIG. 11, Table 1). The contrast in expression patterns between CRF receptor subtypes was particularly evident within the septal region: $CRF_2$ mRNA expression was very high in the lateral septal nuclei but very low in the medial septum, the septal nucleus where $CRF_1$ mRNA abundance was most evident (FIG. 11B). The distribution of $CRF_2$ receptor mRNA within the LS was, however, heterogeneous; very high levels of expression were evident within both the intermediate and ventral sub-nuclei with only an occasionally labelled cell evident in the dorsal sub-division (FIG. 12). Within both the intermediate and ventral regions of the LS the level of $CRF_2$ receptor expression exhibited an apparent rostro-caudal gradient, with a smaller percentage of labelled cells detected in the caudal aspects of both areas. At this level, some scattered $CRF_2$-expressing cells were also evident in both the vertical and horizontal limbs of the diagonal band. Again, contrasting the higher levels of $CRF_1$ mRNA found in these regions (FIG. 11). Differential patterns of CRF receptor subtype expression were also evident within the olfactory bulb (FIG. 11A). Here, $CRF_1$ receptor expression was particularly high in the internal granule cell and mitral cell layers with lower levels detectable in the external granule layer and ependyma. However, most cells expressing $CRF_2$ receptors were found lining the ventricle within the ependymal area and the internal granule cell layer (FIG. 11A). Both $CRF_1$ and $CRF_2$ receptors were also expressed in the accessory olfactory nucleus.

Figure 14A:
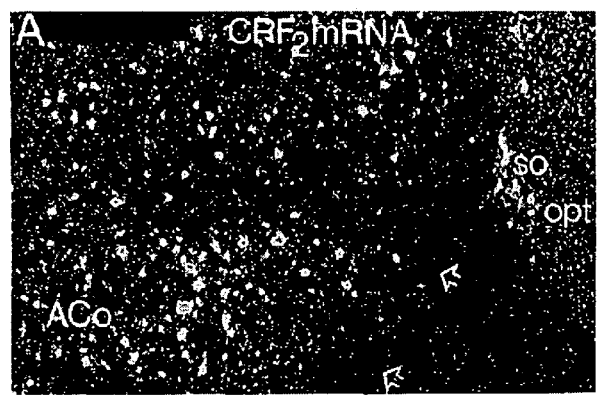
FIGS. 14A and B are two darkfield photomicrographs of cells hybridized with (A) ($^{35}$S) cRNA $CRF_2$ probe and (B)($^{35}$S) cRNA $CRF_1$ probe in the anterior cortical amygdaloid nucleus (ACo). In (A) not the high level of $CRF_2$ receptor mRNA expression in cells throughout the nucleus while in (B) $CRF_1$ receptor expression is comparable to background signal. $CRF_2$ receptor mRNA expression is also evident within the supraoptic nucleus in (A), an area where $CRF_1$ receptor expression is undetectable (B). opt, optic tract, arrows in (A) indicate section edge.
Figure 14B:
Figure 13A:
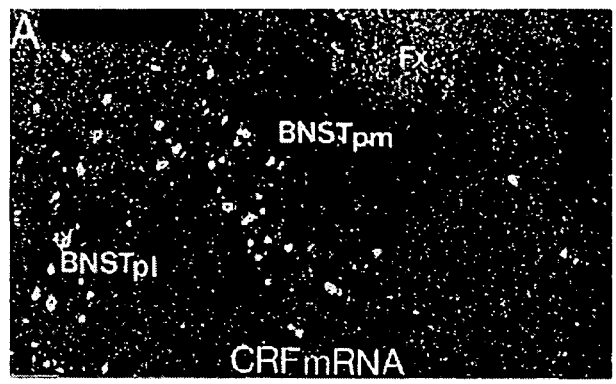
FIGS. 13A, B and C are a series of darkfield photomicrographs of cells hybridized with (A) ($^{35}$S) cRNA CRF probe, (B) ($^{35}$S) cRNA $CRF_2$ probe and (C) ($^{35}$S) cRNA $CRF_1$ probe in adjacent coronal sections through the bed nucleus of the stria terminalis (BNST). In (A) note the higher concentration of CRF-expressing cells in the posterolateral area (BNSTpl) while in (B) $CRF_2$ receptor expression is predominantly localized to the medial aspects of the nucleus (BNSTpm). In (C)$CRF_1$ receptor mRNA expression is evident in both medial and lateral aspects of the nucleus. Fx, formix.
Figure 13B:
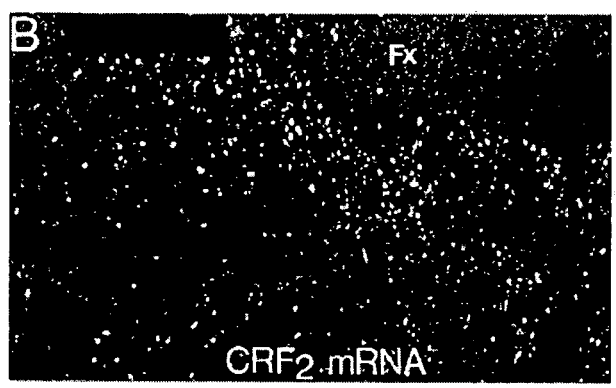
Figure 13C:
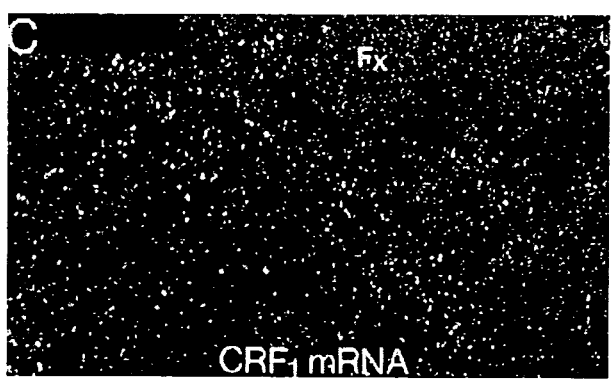
Figure 15A:
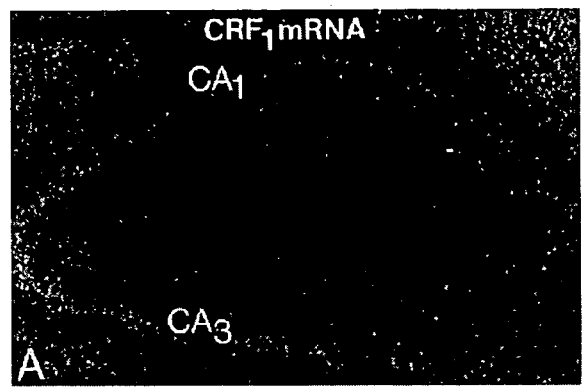
FIGS. 15A, B and C are a series of darkfield photomicrographs of cells hybridized with (A) ($^{35}$S) cRNA $CRF_1$ probe and (B) and (C) ($^{35}$S) cRNA $CRF_2$ probe in the hippocampal formation. Within dorsal hippocampus, both $CRF_1$ and $CRF_2$ receptor expression was relatively low. However, within the ventral hippocampus (C), cells expressing high levels of $CRF_2$ receptor mRNA were evident in the dentate gyrus and subiculum. *, emulsion artifact.
Figure 15B:
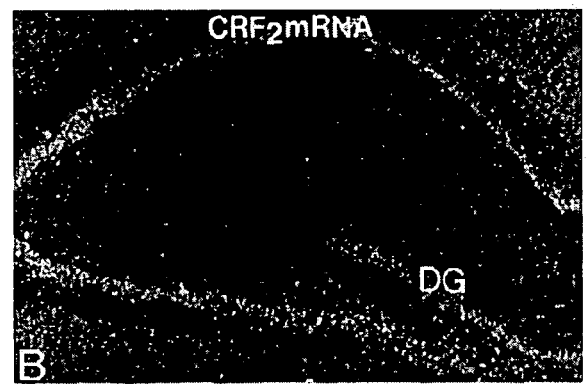
Figure 15C:
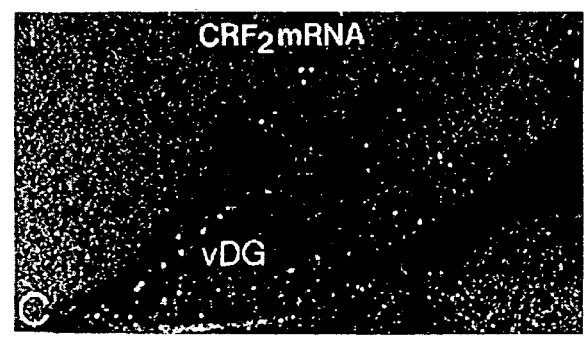

Both $CRF_2$ and $CRF_1$ receptor mRNA expression were evident in the BNST, particularly in the medial aspect, and the amygdaloid area. Within the BNST, $CRF_2$ receptor expression appeared to be lower in the lateral regions where the highest abundance of CRF-expressing cells were found (FIGS. 13A and B). $CRF_1$ receptor expression was found in both medial and lateral divisions of the BNST (FIG. 13C). Within the amygdala the highest levels of $CRF_2$ receptor expression were evident in the cortical and medial amygdaloid nuclei with less expression in the basolateral nucleus (FIG. 11C). In complementary fashion, $CRF_1$ receptor expression was very high in the basolateral area but low in the cortical amygdala (FIG. 14). Both $CRF_1$ and $CRF_2$ receptor mRNA expression were unremarkable in the central nucleus. Within the hippocampal formation, $CRF_2$ receptors were generally expressed in low to moderate levels in pyramidal cells of CA subfields and granule cells of the dentate gyrus. However, scattered cells with high levels of $CRF_2$ expression were evident in non-granule cell layers in ventral dentate gyrus (FIG. 15). $CRF_1$ receptor expression was most abundant in the pyramidal cell layer of $CA_{3/4}$ with moderate levels evident in $CA_1$. However, $CRF_1$ receptor expression was apparently absent in the dorsal dentate gyrus (FIG. 15). Interestingly, higher levels of $CRF_2$ expression were evident in the ventral hippocampus compared to the dorsal aspect (FIGS. 11C and D). Cells expressing both $CRF_1$ and $CRF_2$ were found throughout entorhinal cortex.

Figure 16A:
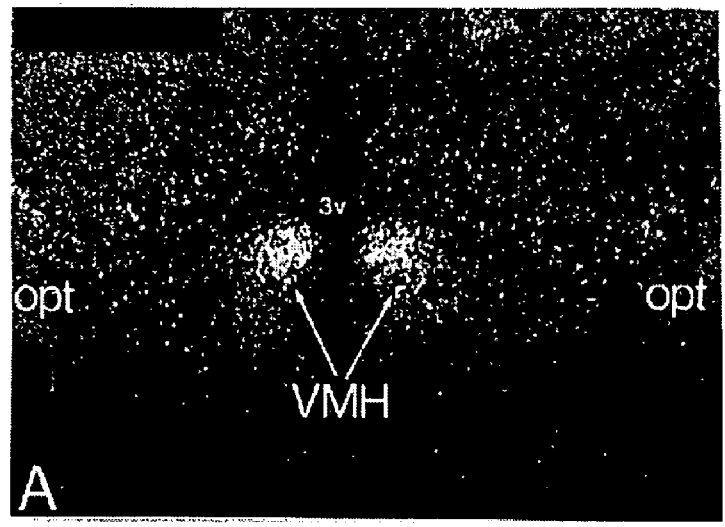
FIGS. 16A and B are two darkfield photomicrographs of cells hybridized with ($^{35}$S)cRNA $CRF_2$ probe in the ventromedial hypothalamic nucleus (VMH)(A) and (B). At high resolution (B), note the high level of $CRF_2$ receptor expression in both the dorsomedial (DM) and ventrolateral (VL) aspects of the nucleus. 3v, third ventricle; opt, optic tract.
Figure 16B:
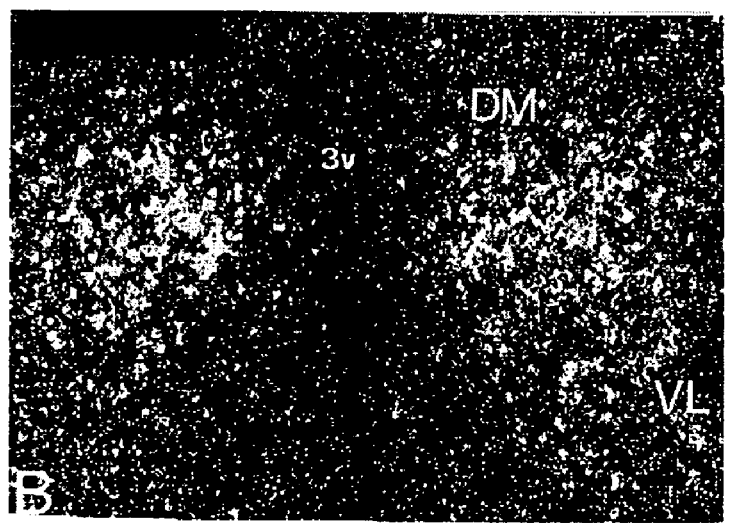
Figure 17C:
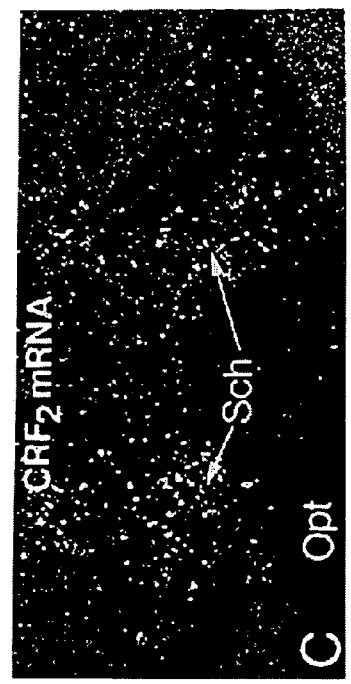
FIGS. 17A, B, C and D are a series of darkfield photomicrographs of cells hybridized with ($^{35}$S) cRNA $CRF_2$ probe (A) and (C) and ($^{35}$S) cRNA $CRF_1$ probe (B) and (D) in adjacent coronal sections through the supraoptic nucleus (SO) and suprachiasmatic nucleus (Sch). Note the absence of $CRF_1$ receptor expression in either nucleus (B) and (D). Opt, optic tract; *, labeled arteriole.
Figure 17D:
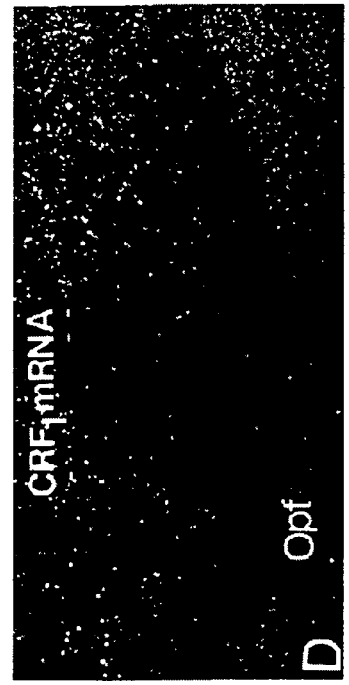
Figure 17A:
Figure 17B:
Figure 18A:
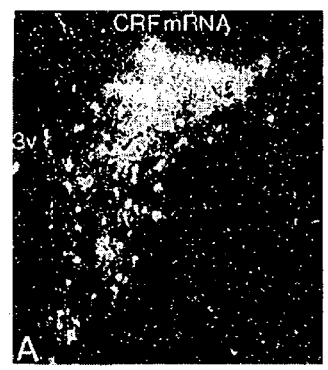
FIGS. 18A, B and C are a series of darkfield photomicrographs of cells hybridized with (A) ($^{35}$S) cRNA CRF probe, (B) ($^{35}$S) cRNA $CRF_2$ probe and (C) ($^{35}$S) cRNA $CRF_1$ probe in adjacent sections through the paraventricular nucleus of the hypothalamus. In (A), CRF expressing cells are evident throughout the medial and dorsal aspects of the paraventricular nucleus. In (B) note that $CRF_2$ receptor expression is most prominent in the medial parvocellular area (mpv) with only scattered labeled cells evident in the dorsal sub-division. $CRF_1$ receptor expression is unremarkable in both sub-divisions (C). 3v, third ventricle; Fx, formix.
Figure 18B:
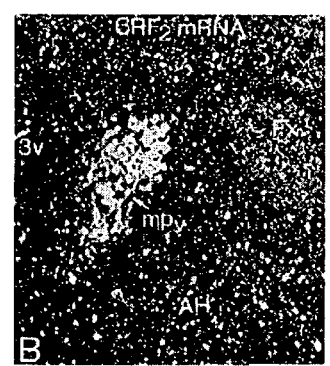
Figure 18C:
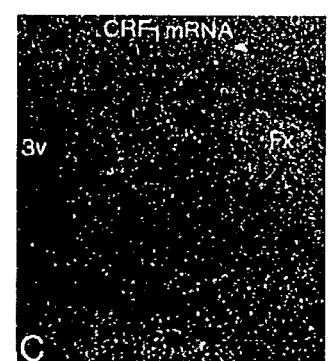

The distribution of $CRF_2$ receptor transcripts in diencephalic structures was confined mainly to the hypothalamus where labelled cells were evident in preoptic, anterior and tuberal regions. The levels of $CRF_2$ mRNA expression found in the ventromedial hypothalamic nuclei (VMH) were amongst the highest detected in brain (FIG. 16). Both dorsal and ventral aspects of VMH displayed high levels of $CRF_2$ mRNA relative to other brain regions although $CRF_2$ mRNA expression was most evident in the dorsomedial division. At this level, however, $CRF_1$ receptor expression was predominantly localized to the dorsomedial hypothalamic nucleus (DMH) with only a limited number of cells labelled in the VMH. In anterior hypothalamus, $CRF_2$ mRNA was localized to highly expressing cells in the supraoptic nucleus (SO) and medial areas of the paraventricular nucleus (PVN) (FIG. 17, FIG. 18). Within the PVN, $CRF_2$ mRNA appeared to be expressed in medial parvocellular cells, partially coinciding with CRF mRNA expression (FIG. 10A). This raises the interesting possibility that $CRF_2$ receptors may act as autoreceptors in selective cells in this nucleus. In both the SO and PVN, the number of cells expressing $CRF_1$ mRNA was extremely low (FIG. 17, FIG. 18). Cells expressing $CRF_2$ mRNA were also evident throughout the anterior and lateral hypothalamic areas, the suprachiasmatic nucleus and in the medial preoptic area (MPA).

Figure 19A:
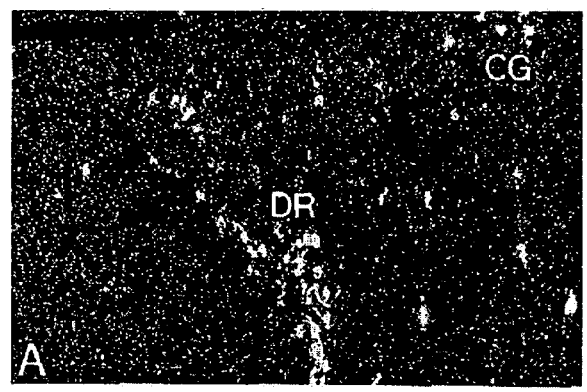
FIGS. 19A, B and C are a series of darkfield photomicrographs of cells hybridized with ($^{35}$S) cRNA $CRF_2$ probe in (A) dorsal raphe (DR) and central gray (CG), (B) median raphe (MnR) and (C) interpeduncular nucleus (IPN).
Figure 19B:
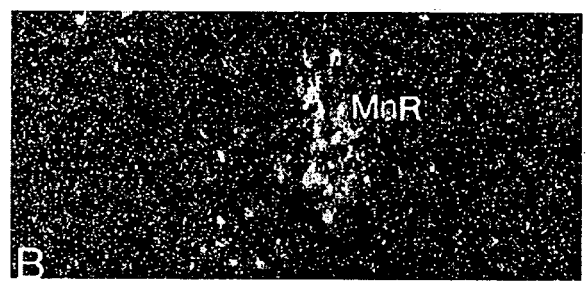
Figure 19C:
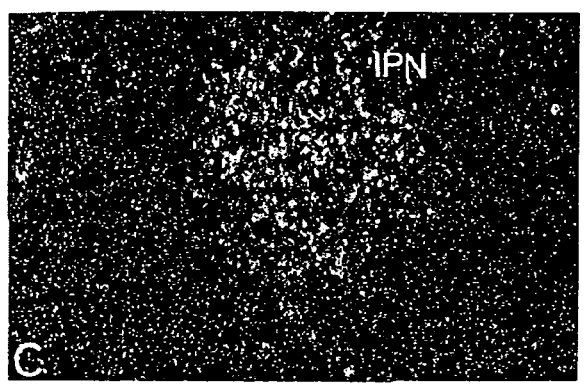

In the midbrain, $CRF_2$-expressing cells were evident throughout nuclei biochemically characterized as serotonin-containing nuclei. Strongly hybridizing cells were localized along the midline in the dorsal raphe nucleus (DR), the caudal linear nucleus, and in the lateral aspects of the central gray (FIG. 19). More ventrally, $CRF_2$ receptor expression was also detectable in the median raphe (MR) and the interpeduncular nucleus (IPN), especially within the rostral subnucleus (FIG. 19). With the exception of IPN, $CRF_1$ receptor mRNA levels were generally low in all of these areas. At this level, $CRF_2$-expressing cells were also evident in clusters in the lateral and dorsal regions of the interior colliculus. However, higher levels of $CRF_1$ mRNA expression was also present in the inferior colliculus. However, higher levels of $CRF_1$ mRNA were found in the visually-receptive fields of the superior colliculus where $CRF_2$ receptor expression was very low. This differential expression pattern was repeated in other sensory relay structures of the brainstem. Thus, while $CRF_1$ receptor mRNA abundance levels were very high in tegmental nuclei and sensory trigeminal areas, $CRF_2$ receptor expression was limited to a few scattered cells in these structures (Table II). Similarly, within the cerebellum, $CRF_1$ receptor mRNA levels were very high in Purkinje and granule cell layers while $CRF_2$ receptor mRNA was present at very limited levels in granule cells (FIG. 11E).

Figure 20A:
FIG. 20A is a photomicrograph which shows $CRF_2$ receptor mRNA expression in the choroid plexus (ChP).
Figure 20B:
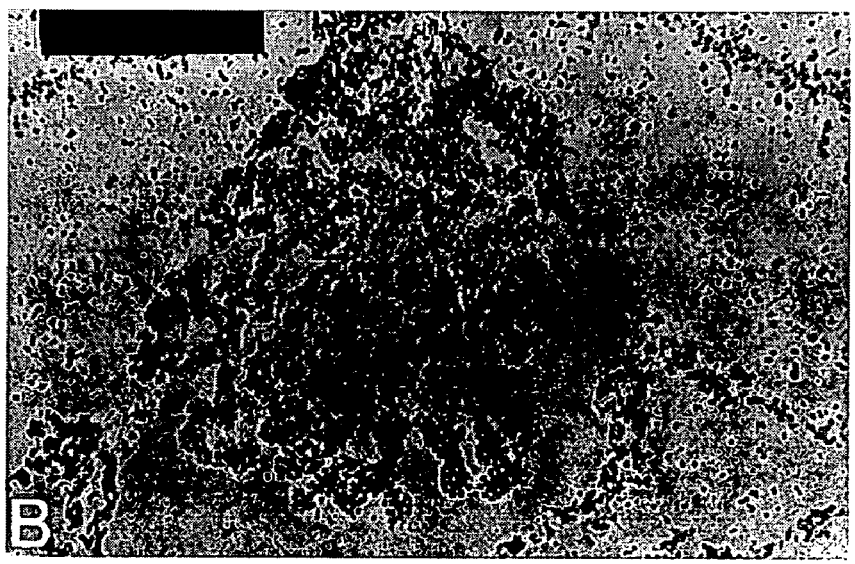
FIG. 20B is a photomicrograph which shows an adjacent nissl stained section. 4v, fourth ventricle.
Figure 21A:
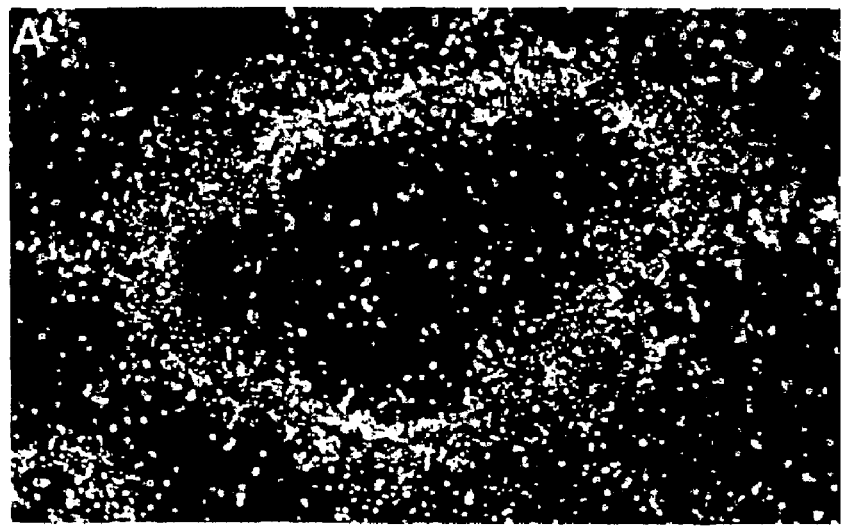
FIG. 21A is a high power darkfield image of $CRF_2$ receptor mRNA expression in a cerebral arteriole.
Figure 21B:
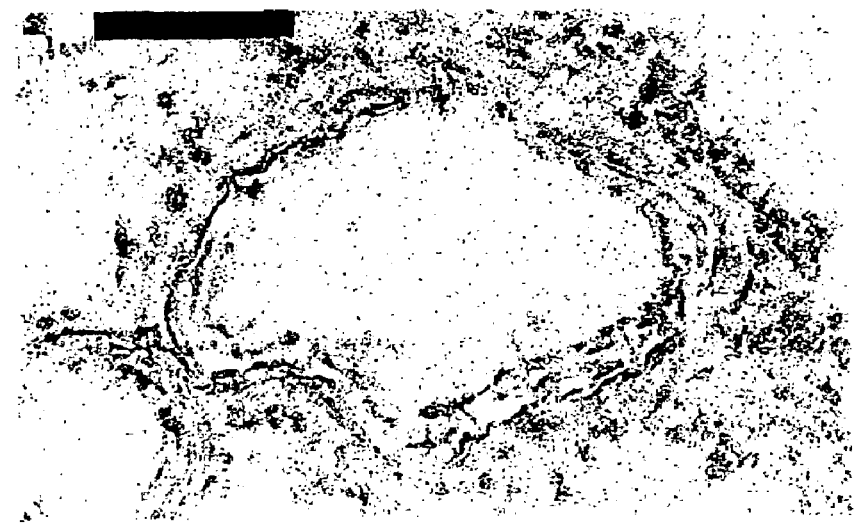
FIG. 21B is a brightfield nissl-stained section of arteriole shown in (A). Note the characteristic muscular arteriole wall in (B).
Figure 22A:
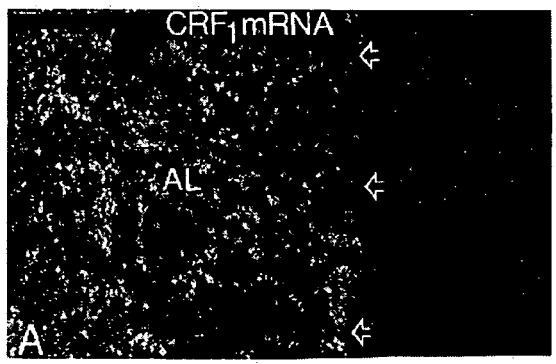
FIGS. 22A, B, C and D are a series of darkfield photomicrographs of CRF, receptor mRNA expression (A) and (B) and $CRF_2$ receptor mRNA expression (C) and (D) in the anterior lobe (AL) of the pituitary gland. In (A), note the clustering of cells expressing $CRF_1$ mRNA presumably reflecting the distribution of pituitary corticotropes while $CRF_2$ mRNA expression is present only in scattered cells (C). At high resolution, prominent accumulation of silver grains are evident over anterior lobe cells hybridized with ($^{35}$S) cRNA $CRF_1$ probe, arrow in (B), while only weak accumulations of silver grains were evident over cells hybridized with ($^{35}$S) cRNA $CRF_2$ probe, arrow in (D).
Figure 22B:
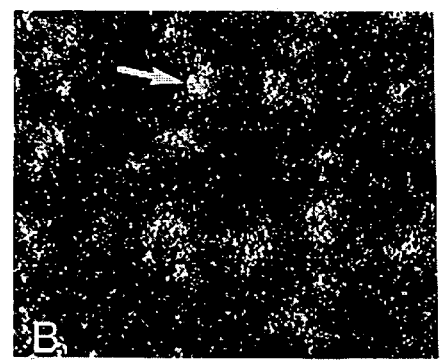
Figure 22C:
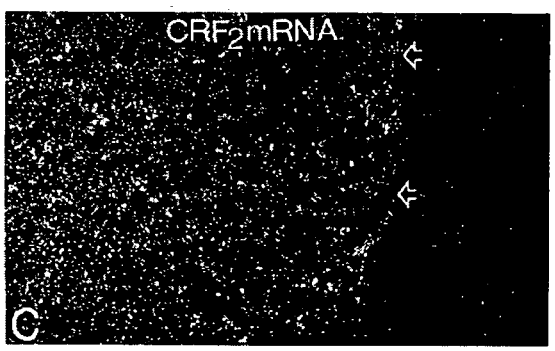
Figure 22D:
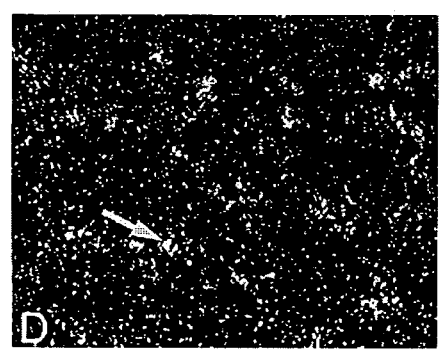

Within non-neuronal structures, a very high level of $CRF_2$ receptor expression was evident in the choroid plexus of the third, fourth and lateral ventricles (FIG. 20). In addition, cerebral arterioles consistently exhibited $CRF_2$ mRNA at all brain levels examined (FIG. 21). CRF, mRNA was detectable at near background levels in these structures. In the pituitary gland, CRF, expression was detectable in both anterior and intermediate lobes with particularly high expression in clusters within the anterior lobe (FIG. 22). Within the anterior lobe, $CRF_2$ receptor expression was detectable only in scattered cells (FIG. 22).

2. Discussion

The present in situ hybridization studies indicate that at least two CRF receptor subtypes, $CRF_1$ and $CRF_2$, are expressed in mammalian rat brain. The heterogeneous anatomical distribution patterns of $CRF_1$ and $CRF_2$ mRNA expression suggests distinct functional roles for each receptor in CRF-related CNS circuits. While $CRF_1$ receptor expression was most abundant in neocortical, cerebellar and sensory relay structures, $CRF_2$ receptor expression was generally localized to specific sub-cortical structures, including the lateral septum and various hypothalamic nuclei.

Within the forebrain, the highest levels of $CRF_2$ receptor expression were found in the lateral septal nuclei. The lateral septum, by virtue of widespread reciprocal connections throughout the brain, is implicated in a variety of physiological processes, which range from higher cognitive functions such as learning and memory to autonomic regulation, including food and water intake. In addition, the septum plays a central role in classical limbic circuitry and is thus important in a variety of emotional conditions including fear and aggression. The lateral septal nuclei receive CRF-containing afferents from rostral hypothalamic regions, particularly the anterior hypothalamic area (Sakanaka et al., *J. Comp. Neurol.* 270:404–415,1988). Interestingly, the majority of these CRF-like immunoreactive fibres are found in the most lateral aspects of the LSV and in the LSI (Sakanaka et al., *J. Comp. Neurol.* 270:404–415,1988), septal subnuclei exhibiting the highest levels of $CRF_2$ receptor mRNA (FIG. 12). The lack of $CRF_1$ receptor expression in these nuclei suggests that $CRF_2$ receptors may solely mediate the postsynaptic actions of CRF inputs to this region. The principal GABAergic neurons of the lateral septum provide inhibitory input to hypothalamic regions, as well as amygdaloid nuclei (Jakab et al., 1991, *Calbindin-containing somatospiny neurons of the rat lateral septal area project to the medial amygdala and the anterior hypothalamus*, Third IBRO World Congress Neuroscience Abstracts, 324) and receive excitatory glutamatergic input from the hippocampal formation (Joels and Urban, *Experimental Brain Research* 54:455–462, 1984). The lateral septum thus acts as both an integrator of limbic circuitry and an interface between telencephalic and diencephalic areas. The high level of $CRF_2$ receptor expression in this area indicates that $CRF_2$ receptors can modulate limbic circuitry at the level of septal activity.

In agreement with previous in situ hybridization studies (Potter et al., *Proceedings of the National Academy of Sciences* 91:8777–8781, 1994), a general lack of $CRF_1$ receptor expression in hypothalamic nuclei was noted. From the present studies it is clear that $CRF_2$ receptor mRNA was evident throughout the rostro-caudal extent of the hypothalamus while $CRF_1$ receptor expression was limited. The difference in CRF receptor subtype expression levels was particularly evident within the paraventricular nucleus where $CRF_2$ receptor expression was readily detectable while $CRF_1$ receptor mRNA was present only in scattered cells. The distribution of cells expressing $CRF_2$ receptor mRNA within the PVN coincides with the cellular distribution of CRF mRNA (FIG. 18) indicating an autoreceptor role for $CRF_2$ receptors in this nucleus. The CRF neurons of the PVN play a classical hypophysiotropic role in controlling ACTH release from the anterior pituitary (Wiegand and Price, *J. Comp. Neurol.* 192:1–19,1980) and as such are central to the control of the mammalian hypothalamo-pituitary-adrenal system. In addition to this stress axis-related role, subpopulations of PVN CRF neurons, particularly within the dorsal parvocellular region and ventral aspect of the medial parvocellular region (mpv), project to autonomic cell groups in the brainstem and spinal cord (Sawchenko, *Brain Res.* 437,1987). Thus, the high level of $CRF_2$ receptor expression within the mpv suggests a presynaptic role for $CRF_2$ receptors in modulating autonomic-related CRF projection neurons.

A selective expression of $CRF_2$ receptor mRNA was also evident in the magnocellular neurosecretory neurons of the supraoptic nucleus. In view of the putative association of $CRF_2$ receptor expression with CRF neurons in the PVN, it is relevant that a subset of SO neurons also synthesize CRF (Kawata et al., *Cell Tissue Research* 230:239–246,1983). The presence of $CRF_2$ receptors in both SO and PVN neurons indicates that these sites may act to influence hypothalamic input to both the anterior and posterior pituitary. Within the pituitary, however, $CRF_1$ receptor expression predominates over $CRF_2$ expression in both the intermediate and anterior lobes. Thus, in terms of HPA axis activity, $CRF_2$ receptors may mediate CRF effects at the level of the hypothalamus while $CRF_1$ receptors are responsible for CRF-induced changes in ACTH release in pituitary corticotropes.

Within the caudal hypothalamus, $CRF_1$ and $CRF_2$ receptors exhibited mutually exclusive patterns of mRNA distribution: $CRF_1$ receptor mRNA being abundant in the dorsomedial nucleus but low within the VMH, while $CRF_2$ receptor mRNA expression was very high within the VMH but undetectable within the DMH. CRF-containing fibres originating in the corticomedial amygdala and subiculum terminate within the VMH (Sakanaka et al., *Brain Res.*

382:213–238,1986). Afferents from the VMH in turn innervate the septum, BNST and amygdala, as well as brainstem regions (Simerly, R. B., Anatomical substrates of hypothalamic integration. In: The Rat Nervous System (Paxinos, G., eds.), pp. 353–376, Academic Press, 1995). Microinjection of CRF into the VMH is associated with changes in both autonomic outflow and gastrointestinal function (Brown and Fisher, Regulation of the autonomic nervous system by corticotropin-releasing factor. In: Corticotropin-releasing factor: Basic and clinical studies of a neuropeptide (De Souza, E. B., Nemeroff, C. B., eds.), pp. 291–298, Boca Raton, Fla., CRC Press, Inc., 1990; Tache et al., CRF: Central nervous system action to influence gastrointestinal function and role in the gastrointestinal response to stress. In: Corticotropin-releasing factor: Basic and clinical studies of a neuropeptide (De Souza, E. B., Nemeroff, C. B., eds.), pp. 299–308, Boca Raton, Fla., CRC Press, Inc., 1990). The high level of $CRF_2$ receptor expression in the VMH implicates this CRF receptor subtype as a terminal or somatodendritic regulator of these CRF-related physiological functions. Moreover, dysregulation of $CRF_2$ receptors in this locus, or the PVN, may participate in the proposed role of central CRF systems in the development of obesity/anorectic syndromes (Krahn and Gosnell, *Psychiatric Medicine* 7:235–245,1989).

In addition to CRF involvement in the development of eating disorders, a large body of evidence exists to implicate this neuropeptide in the pathophysiology of affective diseases such as anxiety and depression. For example, CRF injected into the rodent locus coeruleus produces an anxiogenic response while benzodiazepine anxiolytics have been shown to reduce CRF concentrations in the same nucleus (Owens et al., *J. Pharmacol. Exp. Ther.* 258:349–356, 1991). In clinical studies of major depression, patients have been found to exhibit signs of CRF hypersecretion including: increased CRF concentrations in CSF, increased HPA activity, a blunted ACTH response to CRF and pituitary and adrenal hypertrophy (Owens and Nemeroff, The role of corticotropin-releasing factor in the pathophysiology of affective and anxiety disorders: laboratory and clinical studies. In: Corticotropin-Releasing Factor (Chadwick, D. J., Marsh, J., Ackrill, K., eds.), pp. 296–316, John Wiley and Sons, 1993). In view of the stimulatory role of CRF in HPA activity, it remains possible that the hypercortisolemia observed in depression results from increased central CRF drive. The possibility that hyperactivity of brain CRF circuits may contribute to the symptomatology of depressive illness is supported by preclinical studies in both rodents and nonhuman primates. In both species, central administration of CRF produces a spectrum of behavioral responses reminiscent of human depressive illness (Koob and Britton, Behavioral effects of corticotropin-releasing factor. In: Corticotropin-releasing factor: Basic and clinical studies neuropeptide (De Souza, E. B., Nemeroff, C. B., eds.), Boca Raton, Fla., CRC Press, Inc., 1990; Kalin, Behavioral and endocrine studies of corticotropin-releasing hormone in primates. In: Corticotropin-releasing factor: Basic and clinical studies of a neuropeptide (De Souza, E. B., Nemeroff, C. B., eds.), pp. 275–290, Boca Raton, Fla., CRC Press, Inc., 1990). While the specific underlying mechanisms by which CRF evokes such behavioral responses remain largely undefined, it is likely that modulation of brain limbic circuitry and the participation of specific populations of CRF neurons are involved (Rainnie et al., *J. Pharm. Exp. Therap.* 263: 846–858,1992). In this regard, the present study provides an anatomical basis for the involvement of both $CRF_1$ and $CRF_2$ receptors in mediating limbic CRF effects. While the $CRF_2$ receptor may be regarded as the predominant hypothalamic CRF receptor, both $CRF_1$ and $CRF_2$ receptors were localized to classical limbic structures such as the amygdaloid complex, the hippocampus and the septal nuclei.

In addition to neuroendocrine abnormalities, a convincing body of data indicates dysfunction in central serotonergic activity in depressive illness. From postmortem studies, it is clear that serotonin metabolism and specific receptor subtypes are altered in some brain regions in depressed patients (Meltzer, *Br. J. Psychiat.* 155:25–31,1989; Yates et al., *Psychiatry* 27:489–496,1990). Drugs which inhibit serotonin metabolism, inhibit serotonin uptake from the synapse or act to directly stimulate serotonin receptors are all effective antidepressants (Peroutka and Snyder, *Science* 210:88–90, 1980; Traber and Glaser, *Trends Pharmacol. Sci* 8:432–437, 1987). Thus as both the HPA axis and serotonergic system are implicated in affective disease, it is likely that interactions between these two systems may be relevant to the pathophysiology and pharmacotherapy of depression (Chalmers et al., *Clin. Neurosci.* 1:122–128,1993). In this context, the present data indicates a selective expression of $CRF_2$ receptor mRNA in midbrain serotonergic cell body nuclei. Both dorsal and median raphe nuclei exhibited $CRF_2$ mRNA, as well as cells in serotonin-associated regions of the interpeduncular nucleus and central grey (FIG. 19). As the raphe nuclei receive CRF-ergic input from forebrain regions (Sawchenko and Swanson, Organization of CRF immunoreactive cells and fibers in the rat brain: immunohistochemical studies. In: Corticotropin-releasing factor: Basic and clinical studies of a neuropeptide (De Souza, E. B., Nemeroff, C. B., eds.), pp. 29–52, Boca Raton, Fla., CRC Press, Inc., 1990) any CRF-induced modulation of serotonergic activity is likely to be $CRF_2$ receptor mediated. Such interaction provides an anatomical and biochemical basis for central "stress"-related modulation of serotonergic function and a basis for theories of stress-induced affective disorders.

In addition to neuronal localization the present study also indicates a high level of $CRF_2$ receptor expression in both the choroid plexus and cerebral arterioles. The presence of signal in both structures may be indicative of an endothelial cell localization. The $CRF_2$ cRNA probe used in the present studies did not differentiate between the two apparent splice forms of the $CRF_2$ receptor, $CRF_{2\alpha}$, and $CRF_{2\beta}$ (Lovenberg et al., *Proc. Natl. Acad Sci USA* 92:836–840,1995). However, preliminary data indicates that the $CRF_{2\alpha}$ form of the receptor may predominate in blood vessels. Interestingly, the $CRF_{2\beta}$ receptor is also expressed in peripheral tissues such as heart, lung and skeletal muscle where it may act to mediate vascular effects of CRF.

In summary, a differential cellular distribution of $CRF_2$ and $CRF_1$ receptor mRNA has been identified in rat brain and pituitary gland. This distribution suggests that the $CRF_1$ receptor is the primary neuroendocrine pituitary CRF receptor and plays a dominant role in the cortical, cerebellar and sensory roles of CRF in brain. The regional anatomical distribution of $CRF_2$ receptor mRNA indicates a role for this receptor in relation to hypothalamic neuroendocrine, autonomic and behavioral actions of brain CRF. The presence of $CRF_2$ receptor mRNA in the hypothalamic PVN and medial and cortical amygdaloid regions may indicate an autoreceptor role for this site in selective circuits.

TABLE II

SEMIQUANTITATIVE EVALUATION OF CRF₁ AND CRF₂ RECEPTOR MRNA DISTRIBUTION IN RAT BRAIN AND PITUITARY GLAND

| Anatomical Region | CRF1 mRNA Abundance | CRF2 mRNA Abundance |
|---|---|---|
| Telencephalon: | | |
| Olfactory Bulb: | | |
| External Granular Layer | ++ | – |
| Internal Granular Layer | ++++ | ++ |
| Mitral Cell Layer | ++++ | – |
| Ependyma | ++ | +++ |
| Accessory Olfactory Nucleus | ++ | ++ |
| Frontal Cortex (Superficial) | +++ | – |
| Frontal Cortex (Deep) | +++ | – |
| Cingulate Cortex (Superficial) | +++ | – |
| Cingulate Cortex (Deep) | +++ | – |
| Lateral Septum (Ventral) | + | ++++ |
| Lateral Septum (Intermediate) | + | ++++ |
| Medial Septum | ++ | –/+ |
| Bed Nucleus of the Stria Terminalis (Medial) | ++ | ++ |
| Amygdala: | | |
| Basolateral Nucleus | ++++ | –/+ |
| Medial Nucleus | ++++ | ++ |
| Posterior Cortical | + | +++ |
| Hippocampus: | | |
| CA1 | ++ | ++ |
| CA3/4 | ++++ | ++ |
| Dentate Gyrus | ++ | ++ |
| Entorhinal Cortex | ++ | ++ |
| Diencephalon: | | |
| Hypothalamus: | | |
| Paraventricular Nucleus | –/+ | ++ |
| Supraoptic Nucleus | + | +++ |
| Lateral Hypothalamus | + | + |
| Dorsomedial Hypothalamus | +++ | – |
| Ventromedial Hypothalamic Nucleus | + | ++++ |
| Medial Geniculate Nucleus | ++ | –/+ |
| Mesencephalon: | | |
| Superior Colliculus (Superficial Layer) | +++ | + |
| Interpeduncular Nucleus | ++++ | +++ |
| Dorsal Raphe Nucleus | + | ++ |
| Caudal Linear Nucleus | + | +++ |
| Red Nucleus | ++++ | – |
| Pons/Medulla: | | |
| Inferior Colliculus | ++ | ++ |
| Lateral Dorsal Tegmental Nucleus | ++++ | – |
| Locus Coeruleus | – | – |
| Cerebellar Cortex | ++++ | –/+ |
| Pontine Gray | ++++ | –/+ |
| Motor Trigeminal Nucleus | ++++ | – |
| Sensory Trigeminal Nucleus | +++ | –/+ |
| Choroid Plexus | – | ++++ |
| Pituitary Gland | | |
| Anterior Lobe | +++ | –/+ |
| Intermediate Lobe | +++ | –/+ |
| Posterior Lobe | – | – |

CRF₁ and CRF₂ mRNA abundance for each anatomical region was determined from optical density measurements. Density values for each parameter are presented according to their respective percentile distributions:
++++ (>75%), very dense;
+++ (<75%, >50%), dense;
++ (<50%, >25%), moderate;
+ (<25%, >10%), low;
–/+ (<10%), scattered cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

The invention claimed is:

1. An isolated $CRF_2$ receptor comprising the amino acid sequence of SEQ ID NO:4, from amino acid number 1 to amino acid number 411.

2. An isolated $CRF_2$ receptor N-terminal extracellular domain comprising amino acids 1 to 118 of SEQ ID NO:4.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1514 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 44..1336

(xi) SEQUENCE DESCRIPTION: SEQ ID NO: 1:

```
GATCCCTATC CCTGAGCAAG CGAGTGGCAG GATCTGGTGT CCC ATG GGG CAC CCA      55
                                             Met Gly His Pro
                                              1
```

-continued

| | |
|---|---|
| GGC TCT CTT CCC AGT GCA CAA CTC CTC CTC TGC CTA TAC TCT CTG CTC<br>Gly Ser Leu Pro Ser Ala Gln Leu Leu Leu Cys Leu Tyr Ser Leu Leu<br>5                    10                  15                  20 | 103 |
| CCA CTG CTC CAG GTG GCC CAA CCA GGC AGG CCA CTC CAG GAC CAG CCC<br>Pro Leu Leu Gln Val Ala Gln Pro Gly Arg Pro Leu Gln Asp Gln Pro<br>               25                  30                    35 | 151 |
| CTG TGG ACA CTT TTG GAG CAG TAC TGC CAT AGG ACC ACA ACT CGG AAT<br>Leu Trp Thr Leu Leu Glu Gln Tyr Cys His Arg Thr Thr Thr Arg Asn<br>          40                    45                  50 | 199 |
| TTT TCA GGT CCC TAC TCC TAC TGC AAC ACG ACC TTG GAC CAG ATC GGG<br>Phe Ser Gly Pro Tyr Ser Tyr Cys Asn Thr Thr Leu Asp Gln Ile Gly<br>        55                  60                  65 | 247 |
| ACC TGC TGG CCC CAG AGC GCG CCT GGA GCC CTA GTG GAG AGA CCA TGC<br>Thr Cys Trp Pro Gln Ser Ala Pro Gly Ala Leu Val Glu Arg Pro Cys<br>70                    75                  80 | 295 |
| CCC GAA TAC TTC AAC GGC ATC AAG TAC AAC ACG ACC CGG AAT GCC TAC<br>Pro Glu Tyr Phe Asn Gly Ile Lys Tyr Asn Thr Thr Arg Asn Ala Tyr<br>85                    90                  95                  100 | 343 |
| AGA GAA TGC CTG GAG AAT GGG ACC TGG GCC TCA AGG ATC AAC TAC TCA<br>Arg Glu Cys Leu Glu Asn Gly Thr Trp Ala Ser Arg Ile Asn Tyr Ser<br>                  105                110                115 | 391 |
| CAC TGT GAA CCC ATT TTG GAT GAC AAG CAG AGG AAG TAT GAC CTG CAT<br>His Cys Glu Pro Ile Leu Asp Asp Lys Gln Arg Lys Tyr Asp Leu His<br>                  120                125                130 | 439 |
| TAC CGA ATC GCC CTC ATC ATC AAC TAC CTG GGC CAC TGT GTT TCC GTG<br>Tyr Arg Ile Ala Leu Ile Ile Asn Tyr Leu Gly His Cys Val Ser Val<br>        135                    140                145 | 487 |
| GTG GCC CTG GTG GCT GCT TTC CTG CTT TTC CTA GTG CTG CGG AGT ATC<br>Val Ala Leu Val Ala Ala Phe Leu Leu Phe Leu Val Leu Arg Ser Ile<br>150                    155                160 | 535 |
| CGC TGC CTG CGG AAT GTG ATC CAC TGG AAC CTC ATC ACC ACC TTC ATC<br>Arg Cys Leu Arg Asn Val Ile His Trp Asn Leu Ile Thr Thr Phe Ile<br>165                    170                175                180 | 583 |
| CTG AGA AAC ATC ACG TGG TTC CTG CTG CAA CTC ATC GAC CAC GAA GTG<br>Leu Arg Asn Ile Thr Trp Phe Leu Leu Gln Leu Ile Asp His Glu Val<br>                  185                190                195 | 631 |
| CAT GAG GGC AAT GAG GTC TGG TGC CGC TGC GTC ACC ACC ATA TTC AAC<br>His Glu Gly Asn Glu Val Trp Cys Arg Cys Val Thr Thr Ile Phe Asn<br>                  200                205                210 | 679 |
| TAC TTT GTG GTC ACC AAC TTC TTC TGG ATG TTT GTG GAA GGC TGC TAC<br>Tyr Phe Val Val Thr Asn Phe Phe Trp Met Phe Val Glu Gly Cys Tyr<br>        215                    220                225 | 727 |
| CTG CAC ACG GCC ATC GTC ATG ACG TAC TCC ACG GAG CAT CTG CGC AAG<br>Leu His Thr Ala Ile Val Met Thr Tyr Ser Thr Glu His Leu Arg Lys<br>230                    235                240 | 775 |
| TGG CTC TTC CTC TTC ATT GGA TGG TGC ATA CCC TGC CCT ATC ATT GTC<br>Trp Leu Phe Leu Phe Ile Gly Trp Cys Ile Pro Cys Pro Ile Ile Val<br>245                    250                255                260 | 823 |
| GCC TGG GCA GTT GGC AAA CTC TAC TAT GAG AAT GAG CAG TGC TGG TTT<br>Ala Trp Ala Val Gly Lys Leu Tyr Tyr Glu Asn Glu Gln Cys Trp Phe<br>                  265                270                275 | 871 |
| GGC AAG GAA CCT GGT GAC TTA GTG GAC TAC ATC TAC CAG GGC CCC ATC<br>Gly Lys Glu Pro Gly Asp Leu Val Asp Tyr Ile Tyr Gln Gly Pro Ile<br>                  280                285                290 | 919 |
| ATC CTC GTG CTC CTC ATC AAT TTT GTG TTT CTG TTC AAC ATC GTC AGG<br>Ile Leu Val Leu Leu Ile Asn Phe Val Phe Leu Phe Asn Ile Val Arg<br>        295                    300                305 | 967 |
| ATC CTG ATG ACA AAA CTG CGA GCC TCC ACC ACA TCC GAG ACC ATC CAG<br>Ile Leu Met Thr Lys Leu Arg Ala Ser Thr Thr Ser Glu Thr Ile Gln<br>310                    315                320 | 1015 |

```
TAC AGG AAG GCA GTG AAG GCC ACC CTG GTC CTC CTC CCC CTG TTG GGC      1063
Tyr Arg Lys Ala Val Lys Ala Thr Leu Val Leu Leu Pro Leu Leu Gly
325                 330                 335                 340

ATC ACC TAC ATG CTC TTC TTT GTC AAT CCT GGA GAG GAC GAC CTG TCA      1111
Ile Thr Tyr Met Leu Phe Phe Val Asn Pro Gly Glu Asp Asp Leu Ser
            345                 350                 355

CAG ATT GTG TTC ATC TAC TTC AAC TCT TTC CTG CAG TCC TTT CAG GGT      1159
Gln Ile Val Phe Ile Tyr Phe Asn Ser Phe Leu Gln Ser Phe Gln Gly
        360                 365                 370

TTC TTT GTG TCC GTT TTC TAC TGC TTC TTC AAT GGA GAG GTG CGC TCC      1207
Phe Phe Val Ser Val Phe Tyr Cys Phe Phe Asn Gly Glu Val Arg Ser
    375                 380                 385

GCC CTG AGA AAG CGG TGG CAC CGT TGG CAG GAC CAC CAC GCC CTC CGA      1255
Ala Leu Arg Lys Arg Trp His Arg Trp Gln Asp His His Ala Leu Arg
390                 395                 400

GTG CCT GTG GCC CGG GCC ATG TCC ATT CCC ACA TCG CCC ACC AGG ATC      1303
Val Pro Val Ala Arg Ala Met Ser Ile Pro Thr Ser Pro Thr Arg Ile
405                 410                 415                 420

AGC TTC CAC AGC ATC AAG CAG ACA GCT GCC GTG TGATCCCCTG TCACCCATCT    1356
Ser Phe His Ser Ile Lys Gln Thr Ala Ala Val
                425                 430

GCCCAGCACT CCACCACCGA GGCGGCTTCC TCATTCTTCA CAGCCTTCCC TGGGTCCTCC    1416

TTGCTACACT GACCCTTGGG TGCAGGAGAA GGGGGGGTGG ATGAACTCTC CTGCCGGAAG    1476

AAAGGAAAAC TATGAAATGG AGGCTCTGAA AGACCAGG                            1514

(2) INFORMATION FOR SEQ ID NO: 2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly His Pro Gly Ser Leu Pro Ser Ala Gln Leu Leu Cys Leu
1               5                   10                  15

Tyr Ser Leu Leu Pro Leu Leu Gln Val Ala Gln Pro Gly Arg Pro Leu
            20                  25                  30

Gln Asp Gln Pro Leu Trp Thr Leu Leu Glu Gln Tyr Cys His Arg Thr
        35                  40                  45

Thr Thr Arg Asn Phe Ser Gly Pro Tyr Ser Tyr Cys Asn Thr Thr Leu
    50                  55                  60

Asp Gln Ile Gly Thr Cys Trp Pro Gln Ser Ala Pro Gly Ala Leu Val
65                  70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
            100                 105                 110

Ile Asn Tyr Ser His Cys Glu Pro Ile Leu Asp Asp Lys Gln Arg Lys
        115                 120                 125

Tyr Asp Leu His Tyr Arg Ile Ala Leu Ile Ile Asn Tyr Leu Gly His
    130                 135                 140

Cys Val Ser Val Val Ala Leu Val Ala Ala Phe Leu Leu Phe Leu Val
145                 150                 155                 160

Leu Arg Ser Ile Arg Cys Leu Arg Asn Val Ile His Trp Asn Leu Ile
                165                 170                 175
```

-continued

```
Thr Thr Phe Ile Leu Arg Asn Ile Thr Trp Phe Leu Leu Gln Leu Ile
            180                 185                 190

Asp His Glu Val His Glu Gly Asn Glu Val Trp Cys Arg Cys Val Thr
            195                 200                 205

Thr Ile Phe Asn Tyr Phe Val Val Thr Asn Phe Phe Trp Met Phe Val
            210                 215                 220

Glu Gly Cys Tyr Leu His Thr Ala Ile Val Met Thr Tyr Ser Thr Glu
225                 230                 235                 240

His Leu Arg Lys Trp Leu Phe Leu Phe Ile Gly Trp Cys Ile Pro Cys
            245                 250                 255

Pro Ile Ile Val Ala Trp Ala Val Gly Lys Leu Tyr Tyr Glu Asn Glu
            260                 265                 270

Gln Cys Trp Phe Gly Lys Glu Pro Gly Asp Leu Val Asp Tyr Ile Tyr
            275                 280                 285

Gln Gly Pro Ile Ile Leu Val Leu Leu Ile Asn Phe Val Phe Leu Phe
            290                 295                 300

Asn Ile Val Arg Ile Leu Met Thr Lys Leu Arg Ala Ser Thr Thr Ser
305                 310                 315                 320

Glu Thr Ile Gln Tyr Arg Lys Ala Val Lys Ala Thr Leu Val Leu Leu
            325                 330                 335

Pro Leu Leu Gly Ile Thr Tyr Met Leu Phe Phe Val Asn Pro Gly Glu
            340                 345                 350

Asp Asp Leu Ser Gln Ile Val Phe Ile Tyr Phe Asn Ser Phe Leu Gln
            355                 360                 365

Ser Phe Gln Gly Phe Phe Val Ser Val Phe Tyr Cys Phe Phe Asn Gly
370                 375                 380

Glu Val Arg Ser Ala Leu Arg Lys Arg Trp His Arg Trp Gln Asp His
385                 390                 395                 400

His Ala Leu Arg Val Pro Val Ala Arg Ala Met Ser Ile Pro Thr Ser
            405                 410                 415

Pro Thr Arg Ile Ser Phe His Ser Ile Lys Gln Thr Ala Ala Val
            420                 425                 430
```

(2) INFORMATION FOR SEQ ID NO: 3:

(i) SEQUENCE CHARACTERISTICS:
        (A) LENGTH: 1626 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 216..1449

(xi) SEQUENCE DESCRIPTION: SEQ ID NO: 3:

```
GCGGCCCCTC ATCTCCGTGA GCCCCGAGGC TTCTCTTGGC CAAGGTCCTA GGAGTGATCC    60

GATTGAGAGC GGCGCCCCAA AGCTGCCGGG CTGGCCGGGG TGGGCGGGGA GGCACCTGGA   120

CGCTGCACTC TCTGGTGGCT CCGCGTCGCG CCAGGTCCCT CGCAGCCACG CGGGGCGCGC   180

ACTCCCACTC CCAACGCGCG CGGCTCCGGA GCGCA ATG GAC GCG GCG CTG CTC     233
                                       Met Asp Ala Ala Leu Leu
                                         1               5

CTC AGC CTG CTG GAG GCC AAC TGC AGC CTG GCA CTG GCC GAA GAG CTG    281
Leu Ser Leu Leu Glu Ala Asn Cys Ser Leu Ala Leu Ala Glu Glu Leu
          10                  15                  20

CTT TTG GAC GGC TGG GGA GAG CCC CCG GAC CCC GAA GGT CCC TAC TCC    329
```

-continued

```
Leu Leu Asp Gly Trp Gly Glu Pro Pro Asp Pro Glu Gly Pro Tyr Ser
        25                  30                  35

TAC TGC AAC ACG ACC TTG GAC CAG ATC GGG ACC TGC TGG CCC CAG AGC       377
Tyr Cys Asn Thr Thr Leu Asp Gln Ile Gly Thr Cys Trp Pro Gln Ser
        40                  45                  50

GCG CCT GGA GCC CTA GTG GAG AGA CCA TGC CCC GAA TAC TTC AAC GGC       425
Ala Pro Gly Ala Leu Val Glu Arg Pro Cys Pro Glu Tyr Phe Asn Gly
55                  60                  65                  70

ATC AAG TAC AAC ACG ACC CGG AAT GCC TAC AGA GAA TGC CTG GAG AAT       473
Ile Lys Tyr Asn Thr Thr Arg Asn Ala Tyr Arg Glu Cys Leu Glu Asn
            75                  80                  85

GGG ACC TGG GCC TCA AGG ATC AAC TAC TCA CAC TGT GAA CCC ATT TTG       521
Gly Thr Trp Ala Ser Arg Ile Asn Tyr Ser His Cys Glu Pro Ile Leu
                90                  95                 100

GAT GAC AAG CAG AGG AAG TAT GAC CTG CAT TAC CGA ATC GCC CTC ATC       569
Asp Asp Lys Gln Arg Lys Tyr Asp Leu His Tyr Arg Ile Ala Leu Ile
            105                 110                 115

ATC AAC TAC CTG GGC CAC TGT GTT TCC GTG GTG GCC CTG GTG GCT GCT       617
Ile Asn Tyr Leu Gly His Cys Val Ser Val Val Ala Leu Val Ala Ala
        120                 125                 130

TTC CTG CTT TTC CTA GTG CTG CGG AGT ATC CGC TGC CTG CGG AAT GTG       665
Phe Leu Leu Phe Leu Val Leu Arg Ser Ile Arg Cys Leu Arg Asn Val
135                 140                 145                 150

ATC CAC TGG AAC CTC ATC ACC ACC TTC ATC CTG AGA AAC ATC ACG TGG       713
Ile His Trp Asn Leu Ile Thr Thr Phe Ile Leu Arg Asn Ile Thr Trp
            155                 160                 165

TTC CTG CTG CAA CTC ATC GAC CAC GAA GTG CAT GAG GGC AAT GAG GTC       761
Phe Leu Leu Gln Leu Ile Asp His Glu Val His Glu Gly Asn Glu Val
        170                 175                 180

TGG TGC CGC TGC GTC ACC ACC ATA TTC AAC TAC TTT GTG GTC ACC AAC       809
Trp Cys Arg Cys Val Thr Thr Ile Phe Asn Tyr Phe Val Val Thr Asn
            185                 190                 195

TTC TTC TGG ATG TTT GTG GAA GGC TGC TAC CTG CAC ACG GCC ATC GTC       857
Phe Phe Trp Met Phe Val Glu Gly Cys Tyr Leu His Thr Ala Ile Val
        200                 205                 210

ATG ACG TAC TCC ACG GAG CAT CTG CGC AAG TGG CTC TTC CTC TTC ATT       905
Met Thr Tyr Ser Thr Glu His Leu Arg Lys Trp Leu Phe Leu Phe Ile
215                 220                 225                 230

GGA TGG TGC ATA CCC TGC CCT ATC ATT GTC GCC TGG GCA GTT GGC AAA       953
Gly Trp Cys Ile Pro Cys Pro Ile Ile Val Ala Trp Ala Val Gly Lys
            235                 240                 245

CTC TAC TAT GAG AAT GAG CAG TGC TGG TTT GGC AAG GAA CCT GGT GAC      1001
Leu Tyr Tyr Glu Asn Glu Gln Cys Trp Phe Gly Lys Glu Pro Gly Asp
        250                 255                 260

TTA GTG GAC TAC ATC TAC CAG GGC CCC ATC ATC CTC GTG CTC CTC ATC      1049
Leu Val Asp Tyr Ile Tyr Gln Gly Pro Ile Ile Leu Val Leu Leu Ile
            265                 270                 275

AAT TTT GTG TTT CTG TTC AAC ATC GTC AGG ATC CTG ATG ACA AAA CTG      1097
Asn Phe Val Phe Leu Phe Asn Ile Val Arg Ile Leu Met Thr Lys Leu
        280                 285                 290

CGA GCC TCC ACC ACA TCC GAG ACC ATC CAG TAC AGG AAG GCA GTG AAG      1145
Arg Ala Ser Thr Thr Ser Glu Thr Ile Gln Tyr Arg Lys Ala Val Lys
295                 300                 305                 310

GCC ACC CTG GTC CTC CTC CCC CTG TTG GGC ATC ACC TAC ATG CTC TTC      1193
Ala Thr Leu Val Leu Leu Pro Leu Leu Gly Ile Thr Tyr Met Leu Phe
            315                 320                 325

TTT GTC AAT CCT GGA GAG GAC GAC CTG TCA CAG ATT GTG TTC ATC TAC      1241
Phe Val Asn Pro Gly Glu Asp Asp Leu Ser Gln Ile Val Phe Ile Tyr
        330                 335                 340
```

-continued

```
TTC AAC TCT TTC CTG CAG TCC TTT CAG GGT TTC TTT GTG TCC GTT TTC    1289
Phe Asn Ser Phe Leu Gln Ser Phe Gln Gly Phe Phe Val Ser Val Phe
        345                 350                 355

TAC TGC TTC TTC AAT GGA GAG GTG CGC TCC GCC CTG AGA AAG CGG TGG    1337
Tyr Cys Phe Phe Asn Gly Glu Val Arg Ser Ala Leu Arg Lys Arg Trp
360                 365                 370

CAC CGT TGG CAG GAC CAC CAC GCC CTC CGA GTG CCT GTG GCC CGG GCC    1385
His Arg Trp Gln Asp His His Ala Leu Arg Val Pro Val Ala Arg Ala
375                 380                 385                 390

ATG TCC ATT CCC ACA TCG CCC ACC AGG ATC AGC TTC CAC AGC ATC AAG    1433
Met Ser Ile Pro Thr Ser Pro Thr Arg Ile Ser Phe His Ser Ile Lys
                395                 400                 405

CAG ACA GCT GCC GTG T GATCCCCTGT CACCCATCTG CCCAGCACTC             1479
Gln Thr Ala Ala Val
            410

CACCACCGAG GCGGCTTCCT CATTCTTCAC AGCCTTCCCT GGGTCCTCCT TGCTACACTG  1539

ACCCTTGGGT GCAGGAGAAG GGGGGGTGGA TGAACTCTCC TGCCGGAAGA AAGGAAAACT  1599

ATGAAATGGA GGCTCTGAAA GACCAGG                                     1626

(2) INFORMATION FOR SEQ ID NO: 4:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO: 4:

Met Asp Ala Ala Leu Leu Leu Ser Leu Leu Glu Ala Asn Cys Ser Leu
 1               5                  10                  15

Ala Leu Ala Glu Glu Leu Leu Asp Gly Trp Gly Glu Pro Pro Asp
            20                  25                  30

Pro Glu Gly Pro Tyr Ser Tyr Cys Asn Thr Thr Leu Asp Gln Ile Gly
        35                  40                  45

Thr Cys Trp Pro Gln Ser Ala Pro Gly Ala Leu Val Glu Arg Pro Cys
    50                  55                  60

Pro Glu Tyr Phe Asn Gly Ile Lys Tyr Asn Thr Thr Arg Asn Ala Tyr
65                  70                  75                  80

Arg Glu Cys Leu Glu Asn Gly Thr Trp Ala Ser Arg Ile Asn Tyr Ser
                85                  90                  95

His Cys Glu Pro Ile Leu Asp Asp Lys Gln Arg Lys Tyr Asp Leu His
            100                 105                 110

Tyr Arg Ile Ala Leu Ile Ile Asn Tyr Leu Gly His Cys Val Ser Val
        115                 120                 125

Val Ala Leu Val Ala Ala Phe Leu Leu Phe Leu Val Leu Arg Ser Ile
    130                 135                 140

Arg Cys Leu Arg Asn Val Ile His Trp Asn Leu Ile Thr Thr Phe Ile
145                 150                 155                 160

Leu Arg Asn Ile Thr Trp Phe Leu Leu Gln Leu Ile Asp His Glu Val
                165                 170                 175

His Glu Gly Asn Glu Val Trp Cys Arg Cys Val Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu His Leu Arg Lys
    210                 215                 220
```

```
Trp Leu Phe Leu Phe Ile Gly Trp Cys Ile Pro Cys Pro Ile Ile Val
225                 230                 235                 240

Ala Trp Ala Val Gly Lys Leu Tyr Tyr Glu Asn Glu Gln Cys Trp Phe
            245                 250                 255

Gly Lys Glu Pro Gly Asp Leu Val Asp Tyr Ile Tyr Gln Gly Pro Ile
            260                 265                 270

Ile Leu Val Leu Leu Ile Asn Phe Val Phe Leu Phe Asn Ile Val Arg
        275                 280                 285

Ile Leu Met Thr Lys Leu Arg Ala Ser Thr Thr Ser Glu Thr Ile Gln
        290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Val Phe Ile Tyr Phe Asn Ser Phe Leu Gln Ser Phe Gln Gly
                340                 345                 350

Phe Phe Val Ser Val Phe Tyr Cys Phe Phe Asn Gly Glu Val Arg Ser
                355                 360                 365

Ala Leu Arg Lys Arg Trp His Arg Trp Gln Asp His His Ala Leu Arg
        370                 375                 380

Val Pro Val Ala Arg Ala Met Ser Ile Pro Thr Ser Pro Thr Arg Ile
385                 390                 395                 400

Ser Phe His Ser Ile Lys Gln Thr Ala Ala Val
                405                 410

(2) INFORMATION FOR SEQ ID NO: 5

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 5

CCCGGATGCC TACAGAGAAT GCCTGGAGGA TGGGACCTGG GCCTCAAGGG          50

(2) INFORMATION FOR SEQ ID NO: 6

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO: 6

GATCAACTAC TCACAGTGTG AGCCCATTTT GGATGACAAG CAGAGGAAGT A        51

(2) INFORMATION FOR SEQ ID NO: 7:

(i) SEQUENCE CHARACTERISTICS:
        (A) LENGTH: 1468 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1233

(xi) SEQUENCE DESCRIPTION: SEQ ID NO: 7:

ATG GAC GCG GCA CTG CTC CAC AGC CTG CTG GAG GCC AAC TGC AGC CTG    48
```

```
              Met Asp Ala Ala Leu Leu His Ser Leu Leu Glu Ala Asn Cys Ser Leu
                1               5                  10                  15

GCG CTG GCT GAA GAG CTG CTC TTG GAC GGC TGG GGG CCA CCC CTG GAC              96
Ala Leu Ala Glu Glu Leu Leu Leu Asp Gly Trp Gly Pro Pro Leu Asp
                20                  25                  30

CCC GAG GGT CCC TAC TCC TAC TGC AAC ACG ACC TTG GAC CAG ATC GGA             144
Pro Glu Gly Pro Tyr Ser Tyr Cys Asn Thr Thr Leu Asp Gln Ile Gly
            35                  40                  45

ACG TGC TGG CCC CGC AGC GCT GCC GGA GCC CTC GTG GAG AGG CCG TGC             192
Thr Cys Trp Pro Arg Ser Ala Ala Gly Ala Leu Val Glu Arg Pro Cys
    50                  55                  60

CCC GAG TAC TTC AAC GGC GTC AAG TAC AAC ACG ACC CGG AAT GCC TAT             240
Pro Glu Tyr Phe Asn Gly Val Lys Tyr Asn Thr Thr Arg Asn Ala Tyr
65                  70                  75                  80

CGA GAA TGC TTG GAG AAT GGG ACG TGG GCC TCA AAG ATC AAC TAC TCA             288
Arg Glu Cys Leu Glu Asn Gly Thr Trp Ala Ser Lys Ile Asn Tyr Ser
                85                  90                  95

CAG TGT GAG CCC ATT TTG GAT GAC AAG CAG AGG AAG TAT GAC CTG CAC             336
Gln Cys Glu Pro Ile Leu Asp Asp Lys Gln Arg Lys Tyr Asp Leu His
            100                 105                 110

TAC CGC ATC GCC CTT GTC GTC AAC TAC CTG GGC CAC TGC GTA TCT GTG             384
Tyr Arg Ile Ala Leu Val Val Asn Tyr Leu Gly His Cys Val Ser Val
    115                 120                 125

GCA GCC CTG GTG GCC GCC TTC CTG CTT TTC CTG GCC CTG CGG AGC ATT             432
Ala Ala Leu Val Ala Ala Phe Leu Leu Phe Leu Ala Leu Arg Ser Ile
130                 135                 140

CGC TGT CTG CGG AAT GTG ATT CAC TGG AAC CTC ATC ACC ACC TTT ATC             480
Arg Cys Leu Arg Asn Val Ile His Trp Asn Leu Ile Thr Thr Phe Ile
145                 150                 155                 160

CTG CGA AAT GTC ATG TGG TTC CTG CTG CAG CTC GTT GAC CAT GAA GTG             528
Leu Arg Asn Val Met Trp Phe Leu Leu Gln Leu Val Asp His Glu Val
                165                 170                 175

CAC GAG AGC AAT GAG GTC TGG TGC CAC TGC ATC ACC ACC ATC TTC AAC             576
His Glu Ser Asn Glu Val Trp Cys His Cys Ile Thr Thr Ile Phe Asn
            180                 185                 190

TAC TTC GTG GTG ACC AAC TTC TTC TGG ATG TTT GTG GAA GGC TGC TAC             624
Tyr Phe Val Val Thr Asn Phe Phe Trp Met Phe Val Glu Gly Cys Tyr
    195                 200                 205

CTG CAC ACG GCC ATT GTC ATG ACC TAC TCC ACT GAG CGC CTG CGC AAG             672
Leu His Thr Ala Ile Val Met Thr Tyr Ser Thr Glu Arg Leu Arg Lys
    210                 215                 220

TGC CTC TTC CTC TTC ATC GGA TGG TGC ATC CCC TTC CCC ATC ATC GTC             720
Cys Leu Phe Leu Phe Ile Gly Trp Cys Ile Pro Phe Pro Ile Ile Val
225                 230                 235                 240

GCC TGG GCC ATC GGC AAG CTC TAC TAT GAG AAT GAA CAG TGC TGG TTT             768
Ala Trp Ala Ile Gly Lys Leu Tyr Tyr Glu Asn Glu Gln Cys Trp Phe
                245                 250                 255

GGC AAG GAG CCT GGC GAC CTG GTG GAC TAC ATC TAC CAA GGC CCC ATC             816
Gly Lys Glu Pro Gly Asp Leu Val Asp Tyr Ile Tyr Gln Gly Pro Ile
            260                 265                 270

ATT CTC GTG CTC CTG ATC AAT TTC GTA TTT CTG TTC AAC ATC GTC AGG             864
Ile Leu Val Leu Leu Ile Asn Phe Val Phe Leu Phe Asn Ile Val Arg
    275                 280                 285

ATC CTA ATG ACA AAG TTA CGC GCG TCC ACC ACA TCC GAG ACA ATC CAG             912
Ile Leu Met Thr Lys Leu Arg Ala Ser Thr Thr Ser Glu Thr Ile Gln
    290                 295                 300

TAC AGG AAG GCA GTG AAG GCC ACC CTG GTG CTC CTG CCC CTC CTG GGC             960
Tyr Arg Lys Ala Val Lys Ala Thr Leu Val Leu Leu Pro Leu Leu Gly
305                 310                 315                 320
```

-continued

| | | | | | | | | | | | | | | |
|---|---|---|---|---|---|---|---|---|---|---|---|---|---|---|
| ATC | ACC | TAC | ATG | CTC | TTC | TTC | GTC | AAT | CCC | GGG | GAG | GAC | GAC | CTG | TCA | 1008 |
| Ile | Thr | Tyr | Met | Leu | Phe | Phe | Val | Asn | Pro | Gly | Glu | Asp | Asp | Leu | Ser |
| | | | 325 | | | | | 330 | | | | | 335 | | |

| CAG | ATC | ATG | TTC | ATC | TAT | TTC | AAC | TCC | TTC | CTG | CAG | TCG | TTC | CAG | GGT | 1056 |
| Gln | Ile | Met | Phe | Ile | Tyr | Phe | Asn | Ser | Phe | Leu | Gln | Ser | Phe | Gln | Gly |
| | | | 340 | | | | | 345 | | | | | 350 | | |

| TTC | TTC | GTG | TCT | GTC | TTC | TAC | TGC | TTC | TTC | AAT | GGA | GAG | GTG | CGC | TCA | 1104 |
| Phe | Phe | Val | Ser | Val | Phe | Tyr | Cys | Phe | Phe | Asn | Gly | Glu | Val | Arg | Ser |
| | | | 355 | | | | | 360 | | | | | 365 | | |

| GCC | GTG | AGG | AAG | AGG | TGG | CAC | CGC | TGG | CAG | GAC | CAT | CAC | TCC | CTT | CGA | 1152 |
| Ala | Val | Arg | Lys | Arg | Trp | His | Arg | Trp | Gln | Asp | His | His | Ser | Leu | Arg |
| | | | 370 | | | | | 375 | | | | | 380 | | |

| GTC | CCC | ATG | GCC | CGG | GCC | ATG | TCC | ATC | CCT | ACA | TCA | CCC | ACA | CGG | ATC | 1200 |
| Val | Pro | Met | Ala | Arg | Ala | Met | Ser | Ile | Pro | Thr | Ser | Pro | Thr | Arg | Ile |
| 385 | | | | | 390 | | | | | 395 | | | | | 400 |

| AGC | TTC | CAC | AGC | ATC | AAG | CAG | ACG | GCC | GCT | GTG | TGACCCCTCG GTCGCCCACC | 1253 |
| Ser | Phe | His | Ser | Ile | Lys | Gln | Thr | Ala | Ala | Val |
| | | | | 405 | | | | | 410 | | |

TGCACAGCTC CCCTGTCCTC CTCCACCTTC TTCCTCTGGG TTCTCTGTGC TGGGCAGGCT    1313

CTCGTGGGGC AGGAGATGGG AGGGGAGAGA CCAGCTCTCC AGCCTGGCAG GAAAGAGGGG    1373

GTGCGGCAGC CAAGGGGGAC TGCAAGGGAC AGGGATGAGT GGGGGCCACC AGGCTCAGCG    1433

CAAGAGGAAG CAGAGGGAAT TCGATGGTGG AGCTC                               1468

(2) INFORMATION FOR SEQ ID NO: 8:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO: 8:

| Met | Asp | Ala | Ala | Leu | Leu | His | Ser | Leu | Leu | Glu | Ala | Asn | Cys | Ser | Leu |
|---|---|---|---|---|---|---|---|---|---|---|---|---|---|---|---|
| 1 | | | | 5 | | | | | 10 | | | | | 15 | |

| Ala | Leu | Ala | Glu | Glu | Leu | Leu | Leu | Asp | Gly | Trp | Gly | Pro | Pro | Leu | Asp |
| | | | 20 | | | | | 25 | | | | | 30 | | |

| Pro | Glu | Gly | Pro | Tyr | Ser | Tyr | Cys | Asn | Thr | Thr | Leu | Asp | Gln | Ile | Gly |
| | | 35 | | | | | 40 | | | | | 45 | | | |

| Thr | Cys | Trp | Pro | Arg | Ser | Ala | Ala | Gly | Ala | Leu | Val | Glu | Arg | Pro | Cys |
| | 50 | | | | | 55 | | | | | 60 | | | | |

| Pro | Glu | Tyr | Phe | Asn | Gly | Val | Lys | Tyr | Asn | Thr | Thr | Arg | Asn | Ala | Tyr |
| 65 | | | | | 70 | | | | | 75 | | | | | 80 |

| Arg | Glu | Cys | Leu | Glu | Asn | Gly | Thr | Trp | Ala | Ser | Lys | Ile | Asn | Tyr | Ser |
| | | | | 85 | | | | | 90 | | | | | 95 | |

| Gln | Cys | Glu | Pro | Ile | Leu | Asp | Asp | Lys | Gln | Arg | Lys | Tyr | Asp | Leu | His |
| | | | 100 | | | | | 105 | | | | | 110 | | |

| Tyr | Arg | Ile | Ala | Leu | Val | Val | Asn | Tyr | Leu | Gly | His | Cys | Val | Ser | Val |
| | | 115 | | | | | 120 | | | | | 125 | | | |

| Ala | Ala | Leu | Val | Ala | Ala | Phe | Leu | Leu | Phe | Leu | Ala | Leu | Arg | Ser | Ile |
| | 130 | | | | | 135 | | | | | 140 | | | | |

| Arg | Cys | Leu | Arg | Asn | Val | Ile | His | Trp | Asn | Leu | Ile | Thr | Thr | Phe | Ile |
| 145 | | | | | 150 | | | | | 155 | | | | | 160 |

| Leu | Arg | Asn | Val | Met | Trp | Phe | Leu | Leu | Gln | Leu | Val | Asp | His | Glu | Val |
| | | | | 165 | | | | | 170 | | | | | 175 | |

| His | Glu | Ser | Asn | Glu | Val | Trp | Cys | His | Cys | Ile | Thr | Thr | Ile | Phe | Asn |
| | | | 180 | | | | | 185 | | | | | 190 | | |

-continued

```
Tyr Phe Val Val Thr Asn Phe Phe Trp Met Phe Val Glu Gly Cys Tyr
            195                 200                 205

Leu His Thr Ala Ile Val Met Thr Tyr Ser Thr Glu Arg Leu Arg Lys
            210                 215                 220

Cys Leu Phe Leu Phe Ile Gly Trp Cys Ile Pro Phe Pro Ile Ile Val
225                 230                 235                 240

Ala Trp Ala Ile Gly Lys Leu Tyr Tyr Glu Asn Glu Gln Cys Trp Phe
                    245                 250                 255

Gly Lys Glu Pro Gly Asp Leu Val Asp Tyr Ile Tyr Gln Gly Pro Ile
                260                 265                 270

Ile Leu Val Leu Leu Ile Asn Phe Val Phe Leu Phe Asn Ile Val Arg
            275                 280                 285

Ile Leu Met Thr Lys Leu Arg Ala Ser Thr Thr Ser Glu Thr Ile Gln
            290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Met Phe Ile Tyr Phe Asn Ser Phe Leu Gln Ser Phe Gln Gly
                340                 345                 350

Phe Phe Val Ser Val Phe Tyr Cys Phe Phe Asn Gly Glu Val Arg Ser
                355                 360                 365

Ala Val Arg Lys Arg Trp His Arg Trp Gln Asp His His Ser Leu Arg
            370                 375                 380

Val Pro Met Ala Arg Ala Met Ser Ile Pro Thr Ser Pro Thr Arg Ile
385                 390                 395                 400

Ser Phe His Ser Ile Lys Gln Thr Ala Ala Val
                405                 410
```